(12) United States Patent
Guenther et al.

(10) Patent No.: US 10,138,477 B2
(45) Date of Patent: Nov. 27, 2018

(54) METHOD OF PRODUCING SECRETABLE ANTIBODIES BY EXPRESSION IN SACCHAROMYCES CEREVISIAE

(71) Applicant: Merck Patent GmbH, Darmstadt (DE)

(72) Inventors: Ralph Guenther, Griesheim (DE); Bjoern Hock, Maintal-Doernigheim (DE); Stefan Becker, Darmstadt (DE); Laura Rhiel, Darmstadt (DE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 14/758,856

(22) PCT Filed: Dec. 11, 2013

(86) PCT No.: PCT/EP2013/003748
§ 371 (c)(1),
(2) Date: Jul. 1, 2015

(87) PCT Pub. No.: WO2014/106527
PCT Pub. Date: Jul. 10, 2014

(65) Prior Publication Data
US 2015/0337292 A1 Nov. 26, 2015

(30) Foreign Application Priority Data
Jan. 3, 2013 (EP) .................................... 13000016

(51) Int. Cl.
*C12N 15/10* (2006.01)
*C07K 16/00* (2006.01)

(52) U.S. Cl.
CPC ........ *C12N 15/1037* (2013.01); *C07K 16/005* (2013.01); *C07K 2317/14* (2013.01); *C07K 2317/569* (2013.01); *C07K 2317/624* (2013.01)

(58) Field of Classification Search
CPC .............. C07K 16/005; C07K 2317/14; C07K 2317/569; C07K 2317/624; C12N 15/1037
See application file for complete search history.

(56) References Cited

U.S. PATENT DOCUMENTS

| 7,166,423 B1 | 1/2007 | Miltenyi et al. | |
|---|---|---|---|
| 8,067,339 B2 | 11/2011 | Prinz et al. | |
| 2006/0034845 A1* | 2/2006 | Silence | C07K 16/241 424/145.1 |
| 2009/0148866 A1* | 6/2009 | Datwyler | C07K 16/40 435/7.4 |
| 2010/0009866 A1* | 1/2010 | Prinz | C07K 16/2887 506/9 |
| 2013/0040897 A1* | 2/2013 | Aebi | C12N 9/1051 514/20.9 |

FOREIGN PATENT DOCUMENTS

| WO | 02/04602 A1 | 1/2002 |
|---|---|---|
| WO | 2007042289 A2 | 4/2007 |
| WO | 2010005863 A1 | 1/2010 |

OTHER PUBLICATIONS

Rao et al., Enhanced secretion and low temperature stabilization of a hyperthermostable and Ca2+-independent alpha-amylase of Geobacillus thermoleovorans by surfactants; Letters in Applied Microbiology, vol. 36, pp. 191-196, 2002.*
International Search Report from PCT Application No. PCT/EP2013/003748 dated Jan. 27, 2014.
Rakestraw, J.A. et al. "Secretion-and-capture cell-surface display for selection of target-binding proteins" Protein Engineering, Design & Selection, [2011], vol. 24, No. 6, pp. 525-530.
Ito, Junji et al. "Regulation of the Display Ratio of Enzymes on the Saccharomyces cerevisiae Cell Surface by the Immunoglobulin G and Cellulosomal Enzyme Binding Domains" Applied and Environmental Microbiology [2009], pp. 4149-4154.
Shibasaki, Seiji et al. "Construction of a novel synergistic system for production and recovery of secreted recombinant proteins by the cell surface engineering" Appl Microbiol Biotechnol [2007], vol. 75, pp. 821-828.
Fukuda, Nobuo et al. "High-efficiency recovery of target cells using improved yeast display system for detection of protein-protein interactions" [2007], vol. 76, pp. 151-158.
Mazor, Y. et al., "Selection of full-length IgGs by tandem display on filamentous phage particles and *Escherichia coli* fluorescence-activated cell sorting screening", FEBS Journal, vol. 277, 2010, pp. 2291-2303.
Nakamura, Y. et al., "Development of novel whole-cell immunoadsorbents by yeast surface display of the IgG-binding domain", Appl Microbial Biotechnol, vol. 57, 2001, pp. 500-505.
Ito, J. et al, "Regulation of the Display Ratio of Enzymes on the Saccharomyces cerevisiae Cell Surface by the Immunoglobulin G and Cellulosomal Enzyme Binding Domains", Applied and Environmental Microbiology, vol. 75, No. 12, Jun. 2009, pp. 4149-4154.
Samuelsson, E. et al., "Enhanced in Vitro Refolding of Insulin-like Growth Factor I Using a Solubilizing Fusion Partner", Biochemistry, vol. 33, 1994, pp. 4207-4211.
Samuelsson, E. et al., "Chaperone-Like Effect during in Vitro Refolding of Insulin-Like Growth Factor I Using a Solubilizing Fusion Partner", Ann. N. Y. Acad. Sci., vol. 782, 1996, pp. 486-494.
Robinson, A. et al., "Protein Disulfide Isomerase Overexpression Increases Secretion of Foreign Proteins in *Saccharomyces cerevisiae*", Bio/Technology, vol. 12, Apr. 1994, pp. 381-384.

(Continued)

*Primary Examiner* — Addison D Ault
(74) *Attorney, Agent, or Firm* — Womble Bond Dickinson (US) LLP

(57) ABSTRACT

The invention relates to a method for the production and non-covalent surface display of antibodies and derived fragments as well as molecule libraries based thereon on the surface of *S. cerevisiae* cells. The non-covalent manner of the surface display renders possible the selection of specific variants by means of high throughput screening and the subsequent switchable secretion of the selected binding molecule into the culture supernatant for biochemical characterization.

9 Claims, 19 Drawing Sheets

(56) References Cited

OTHER PUBLICATIONS

Hiniker, A. et al., "Disulfide relays between and within proteins: the Ero1p structure", Trends in Biochemical Sciences, vol. 29, No. 10, Oct. 2004, pp. 516-519.
Gulich, S. et al., "Protein engineering of an IgG-binding domain allows milder elution conditions during affinity chromatography", Journal Biotechnology, vol. 76, 2000, pp. 233-244.
Schekman, R., "The secretory pathway in yeast", TIBS, Jul. 1982, pp. 243-246.
Arnold, K. et al., "The dielectric properties of aqueous solutions of poly(ethylene glycol) and their influence on membrane structure", Biochimica et Biophysica Acta, vol. 815, 1985, pp. 515-518.
Kuhl, T. et al., "Direct Measurement of Plyethylene Glycol Induced Depletion Attraction between Lipid Bilayers", Langmuir, vol. 12, 1996, pp. 3003-3014.
Boni, L.T. et al., "Lipid-Plyethylene Glycol Interactions: I. Induction of Fusion between Liposomes", The Journal of Membrane Biology, vol. 62, 1981, pp. 65-70.
Kramer, W. et al., "Kinetic Studies for the Optimization of Recombinant Protein Formation", Annals New York Academy of Sciences, vol. 782, 1996, pp. 323-333.
Sanden, A. et al., "Limiting Factors in *Escherichia coli* Fed-Batch Production of Recombinant Proteins", Biotechnol. Bioeng., vol. 81, 2003, pp. 158-166.
Berthelemy, P. et al., "Comprehensive Analysis of the Factors Contributing to the Stability and Solubility of Autonomous Human VH Domains", The Journal of Biological Chemistry, vol. 283, No. 6, Feb. 8, 2008, pp. 3639-3654.
Ueda, M. et al., "Genetic immobilization of proteins on the yeast cell surface", Biotechnology Advances, vol. 18, 2000, pp. 121-140.
Saerens, D. et al., "Single-domain antibodies as building blocks for novel therapeutics", Current Opinion in Pharmacology, vol. 8, 2008, pp. 600-608.
Yamane-Ohnuki, N. et al., "Production of therapeutic antibodies with controlled fucosylation", mAbs, vol. 1, Issue 3, 2009, pp. 230-236.
Deisenhofer, J., "Crystallographic Refinement and Atomic Models of a Human Fc Fragment and Its Complex with Fragment B of Protein A from *Staphylococcus aureus* at 2.9- and 2.8-A Resolution", Biochemistry, vol. 20, No. 9, Apr. 28, 1981, pp. 2361-2370.
Vajdos, F. et al., "Comprehensive Functional Maps of the Antigen-binding Site of an Anti-ErbB2 Antibody Obtained with shotgun Scanning Mutagenesis", The Journal of Molecular Biology, vol. 320, 2002, pp. 415-428.
Hashimoto, Y. et al., "Effects of signal sequences on the secretion of hen lysozyme by yeast: construction of four secretion cassette vectors", Protein Engineering, vol. 11, No. 2, 1998, pp. 75-77.
Sazinsky, S. et al., "Aglycosylated Immunoglobulin G1 Variants productively engage activating Fc receptors", PNAS, vol. 105, No. 51, Dec. 23, 2008, pp. 20167-20172.
Ewert, S. et al., "Biophysical Properties of Camelid VHH Domains Compared to Those of Human VH3 Domains", Biochemistry, vol. 41, 2002, pp. 3628-3636.
Ewert, S. et al., "Biophysical Properties of Human Antibody Variable Domains", The Journal of Molecular Biology, vol. 325, 2003, pp. 531-553.
De Genst, E. et al., "Molecular basis for the preferential cleft recognition by dromedary heavy-chain antibodies", PNAS, vol. 103, No. 12, Mar. 21, 2006, pp. 4586-4591.
Neuberger, M. et al., "Somatic hypermutation at AT pairs: polymerase error versus dUTP incorporation", Nature Reviews: Immunology, vol. 5, Feb. 2005, pp. 171-178.
Bostrom, J. et al., "Variants of the Antibody Herceptin that Interact with HER2 and VEGF at the Antigen Binding Site", Science, vol. 323, Mar. 20, 2009, pp. 1610-1614.
Baeuerle, P. et al., "Bispecific T-Cell Engaging Antibodies for Cancer Therapy", Cancer Res, vol. 69, No. 12, Jun. 15, 2009, pp. 4941-4944.
Mack, M. et al., "A small bispecific antibody construct expressed as a functional single-chain molecule with high tumor cell cytotoxcity", Proc. Natl. Acad. Sci., vol. 92, Jul. 1995, pp. 7021-7025.
Brennan, F. et al., "Safety and immunotoxicity assessment of immunomodulatory monoclonal antibodies", mAbs, vol. 2, No. 3, 2010, pp. 233-255.
Delano, W. et al., "Convergent Solutions to Binding at a Protein-Protein Interface", Science, vol. 287, Feb. 18, 2000, pp. 1279-1283.
Li, S. et al., "Structural basis for inhibition of the epidermal growth factor receptor by cetuximab", Cancer Cell, vol. 7, Apr. 2005, pp. 301-311.
Loisel, S. et al., "Relevance, advantages and limitations of animal models used in the development of monoclonal antibodies for cancer treatment", Critical Reviews in Oncology/Hematology, vol. 62, 2007, pp. 34-42.
Muyldermans, S. et al., "Recognition of antigens by single-domain antibody fragments: the superfluous luxury of paired domains", Trends in Biochemical Sciences, vol. 26, No. 4, Apr. 2001, pp. 230-235.
Shusta, E. et al., "Yeast Polypeptide Fusion Surface Display Levels Predict Thermal Stability and Soluble Secretion Efficiency", The Journal of Molecular Biology, vol. 292, 1999, pp. 949-956.
Kieke, M. et al., "Selection of functional T cell receptor mutants from a yeast surface-display library", Proc. Natl. Acad. Sci., vol. 96, May 1999, pp. 5651-5656.
"Methocel Cellulose Ethers: Technical Handbook", Dow, 2002, 3 pages.
Harlow, E. et al., "Antibodies: A Laboratory Manual", 1988, 3 pages.
"Polyethylenglykole", MAK, 1995, 1 page.
"Detailed Contents", Murphy, 10 pages.
Knippers, R., "Inhaltsverzeichnis", Molekulare Genetik, 2006, 11 pages.
Schmiedl, A.D.S., "Rekombinante Antikorper and Phagen-Display", Molekulare Biotechnologie, 2004, 32 pages.
Harmsen, M. et al., "Properties, production, and applications of camelid single-domain antibody fragments", Appl Microbiol Biotechnol, vol. 77, 2007, pp. 13-22.
Muyldermans, S. et al., "Sequence and structure of VH domain from naturally occurring camel heavy chain immunoglobulins lacking light chains", Protein Engineering, vol. 7, No. 9, 1994, pp. 1129-1135.
Desmyter, A. et al., "Antigen Scificity and High Affinity Binding Provided by One Single Loop of a Camel Single-Domain Antibody", The Journal of Biological Chemistry, vol. 276, No. 28, Jul. 13, 2001, pp. 26285-26290.
Chothia, C. et al., "Domain Association in Immunoglobulin Molecules: The Packing of Variable Domains", Journal of Molecular Biology, vol. 186, 1985, pp. 651-663.
Desmyter, A. et al., "Crystal structure of a camel single-domain VH antibody fragment in complex with lysozyme", Nature Structural Biology, vol. 3, No. 9, Sep. 1996, pp. 803-811.
Braden, B. et al., "Three-dimensional Structures of the Free and the Antigen-complexed Fab from Monoclonal Anti-lysozyme Antibody D44.1", Journal of Molecular Biology, vol. 243, 1994, pp. 767-781.
Van Der Linden, R.H.J. et al., "Comparison of Physical chemical properties of llama VHH antibody fragments and mouse monoclonal antibodies", Biochimica et Biophysica Acta, vol. 1431, 1999, pp. 37-46.
Cortez-Retamozo, V. et al., "Efficient Tumor Targeting by Single-Domain Antibody Fragments of Camels", Int. J. Cancer, vol. 98, 2002, pp. 456-462.
Foster, T., "Immune Evasion by Staphylococci", Nature, vol. 3, Dec. 2005, pp. 948-958.
Moks, T. et al., "Staphylococcal protein A consists of five IgG-binding domains", Eur. J. Biochem, vol. 156, 1986, pp. 637-643.
Jansson, B. et al., "All individual domains of staphylococcal protein A show Fab binding", FEMS Immunology and Medical Microbiology, vol. 20, 1998, pp. 69-78.
Uhlen, M. et al., "Complete Sequence of the Staphylococcal Gene Encoding Protein A: A Gene Evolved Through Multiple Duplications", The Journal of Biological Chemistry, vol. 259, No. 4, Feb. 10, 1984, pp. 1695-1702.

(56) References Cited

OTHER PUBLICATIONS

Ackerstrom, B. et al., "A Physicochemical Study of Protein G, a Molecule with Unique Immunoglobulin G-binding Properties", The Journal of Biological Chemistry, vol. 261, No. 22, Aug. 5, 1986, pp. 10240-10247.
Nilsson, B. et al., "A synthetic IgG-binding domain based on staphylococcal protein A", Protein Engineering, vol. 1, No. 2, 1987, pp. 107-113.
Ljungberg, U. et al, "The Interaction between different domains of Staphylococcal Protein A and Human Polyclonal IgG, IgA, IgM and F(ab')2: Seperation of Affinity From Specificity", Molecular Immunology, vol. 30, No. 14, 1993, pp. 1279-1285.
Tashiro, M. et al., "High-resolution Solution NMR Structure of the Z Domain of Staphylococcal Protein A", J. Mol. Biol., vol. 272, 1997, pp. 573-590.
Jendeberg, L. et al., "The Mechanism of Binding Staphylococcal Protein A to Immunoglobin G Does Not Involve Helix Unwinding", Biochemistry, vol. 35, 1996, pp. 22-31.
Nilsson, J. et al., "Compeittive elution of protein A fusion proteins allows specific recovery under mild conditions", Eur. J. Biochem., vol. 224, 1994, pp. 103-108.
Kuypers, D. et al., "Monoclonal antibodies in renal transplantation: old and new", Nephrol Dial Transplant, vol. 19, 2004, pp. 297-300.
Renders, L. et al., "Engineered CD3 antibodies for immunosuppression", Clin. Exp. Immunol, vol. 133, 2003, pp. 307-309.
Hansel, T. et al., "The safety and side effects of monoclonal antibodies", Nature Reviews: Drug Discovery, vol. 9, Apr. 2010, pp. 325-338.
Riechmann, L. et al., "Reshaping human antibodies for therapy", Nature, vol. 332, Mar. 24, 1988, pp. 323-327.
Lonberg, N., "Human antibodies from transgenic animals", Nature Biotechnology, vol. 23, No. 9, Sep. 2005, pp. 1117-1125.
Lonberg, N., "Fully human antibodies from transgenic mouse and phage display platforms", Current Opinion in Immunology, vol. 20, 2008, pp. 450-459.
Hoogenboom, H. et al., "Selecting and screening recombinant antibody libraries", Nature Biotechnology, vol. 23, No. 9, Sep. 2005, pp. 1105-1116.
Jung, Y. et al., "Generation of human monoclonal antibodies against Propionibacterium acnes by applying the phage display method to human peripheral blood mononuclear cells immunized in vitro", Cytotechnology, vol. 57, 2008, pp. 167-175.
Kuroda, D. et al., "Systematic calssification of CDR-L3 in antibodies: Implications of the light chain subtypes and the VL-VH interface", Proteins, vol. 75, 2009, pp. 139-146.
Al-Lazikani, B. et al., "Standard Confirmations for the Canonical Structures of Immunoglobulins", J. Mol. Biol., vol. 273, 1997, pp. 927-948.
Arnold, F. et al., "Optimizing Industrial Enzymes by Directed Evolution", Advances in Biochemical Engineering/Biotechonology, vol. 58, 1997, pp. 1-14.
Dougherty, M. et al., "Directed evolution: new parts and optimized function", Curr. Opin. Biotechnol., vol. 20, No. 4, Aug. 2009, pp. 486-491.
Kaur, J. et al., "Directed Evolution: An Approach to Engineer Enzymes", Critical Reviews in Biotechnology, vol. 26, 2006, pp. 165-199.
Stemmer, W., "Rapid evolution of a protein in vitro by DNA shuffling", Nature, vol. 370, Aug. 4, 1994, pp. 389-391.
Blagodatski, A. et al., "Technologies of directed protein evolution in vivo", Cell. Mol. Life Sci., vol. 68, 2011, pp. 1207-1214.
Hanes, J. et al., "In vitro selection and evolution of functional proteins by using ribosome display", Proc. Natl. Acad. Sci., vol. 94, May 1997, pp. 4937-4942.
Smith, G., "Filamentous Fusion Phage: Novel Expression Vectors That Display Cloned Antigens on the Virion Surface", Science, vol. 228, Jun. 4, 1985, pp. 1315-1317.
Jespers, L. et al., "Guiding the Selection of Human Antibodies from Phage Display Repertoires to a Single Epitope of an Antigen", Nature: Bio/Technology, vol. 12, Sep. 1994, pp. 899-903.

Boder, E. et al., "Yeast surface display for screening combinatorial polypeptide libraries", Nature Biotechnology, vol. 15, Jul. 1997, pp. 553-557.
Van Der Vaart, J. et al., "Comparison of Cell Wall Proteins of *Saccharomyces cerevisiae* as Anchors for Cell Surface Expression of Terologous Proteins", Applied and Environmental Microbiology, vol. 63, No. 2, Feb. 1997, pp. 615-620.
Sato, N. et al., "Long anchor using Flo1 protein enhances reactivity of cell surface-displayed glucoamylase to polymer substrates", Appl Microbiol Biotechnol., vol. 60, 2002, pp. 469-474.
Feldhaus, M. et al., "Flow-cytometric isolation of human antibodies from a nonimmune *Saccharomyces cerevisiae* surface display library", Nature biotechnology, vol. 21, Feb. 2003, pp. 163-170.
Beucken, T. et al., "Affinity maturation of Fab antibody fragments by fluorescent-activated cell sorting of yeast-displayed libraries", FEBS Letters, vol. 546, 2003, pp. 288-294.
Kondo, A. et al., "Yeast ell-surface display-applicaiton of molecular display", Appl. Microbiol. Biotechnol., vol. 64, 2004, pp. 28-40.
Huang, G. et al., "Posttranslational Modificationa Required for Cell Surface Localization and Function of the Fungal Adhesin Aga1p", Eukaryotic Cell, vol. 2, No. 5, Oct. 2003, pp. 1099-1114.
Pepper, L. et al., "A decade of yeast surface display technology: Where are we now?", Comb. Chem. High. Throughput Screen, vol. 11, No. 2, Feb. 2008, pp. 127-134.
Skerra, A. et al., "Assembly of a Functional Immunoglobulin Fv Fragment in *Escherichia coli*", Science, vol. 240, May 20, 1988, pp. 1038-1041.
Jost, C. et al., "Mammalian Expression and Secretion of Functional Single-chain Fv Molecules", The Journal of Biological Chemistry, vol. 269, No. 42, Oct. 21, 1994, pp. 26267-26273.
Goffeau, A. et al., "Life with 6000 Genes", Science, vol. 274, Oct. 25, 1996, 6 pages.
Mortimer, R. et al., "Genetic and Physical Maps of *Saccharomyces cervisiae*, Edition 11", Yeast, vol. 8, 1992, pp. 817-902.
Jeong, K. et al., "Recombinant antibodies: Engineering and production in yeast and bacterial hosts", Biotechnology Journal, vol. 6, 2011, pp. 16-27.
Strausberg, R. et al., "Overiew of Protein Expression in *Saccharomyces cerevisiae*", Current Protocols in Protein Science, Unit 5, 1995, 7 pages.
Muller, S. et al., "Comparison of Expression Systems in the Yeasts *Saccharomyces cerevisiae*, Hansenula polymorpha, Klyveromyces lactis, Schizosaccharomyces pombe and Yarrowia lipolytica. Cloning of Two Novel Promoters from Yarrowia lipolytica", Yeast, vol. 14, 1998, pp. 1267-1283.
Freyre, F. et al., "Very high expression of an anti-carcinoembryonic antigen single chain Fv antibody fragment in the yeast Pichia pastoris", Journal of Biotechnology, vol. 76, 2000, pp. 157-163.
Kretzschmar, T. et al., "High-level expression in insect cells and purification and secreted monomeric single-chain Fv antibodies", Journal of Immunological Methods, vol. 195, 1996, pp. 93-101.
Sanchez, L. et al., "High cytoplasmic expression in *E. coli*, purification, and in vitro refolding of a single chain Fv antibody fragment against the hepatitis B surface antigen", Journal of Biotechnology, vol. 72, 1999, pp. 13-20.
Horwitz, A. et al, "Secretion of functional antibody and Fab fragment from yeast cells", Proc. Natl. Acad. Sci., vol. 85, Nov. 1988, pp. 8678-8682.
Rakestraw, J. et al., "Directed Evolution of a Secretory Leader for the Improved Expression of Heterologous Proteins and Full-Length Antibodies in *Saccharomyces cerevisiae*", Biotechnology and Bioengineering, vol. 103, 2009, pp. 1192-1201.
Machamer, C. et al., "Heavy Chain Binding Protein Recognizes Incompletely Disulfide-bonded Forms of Vesicular Stomatitis Virus G Protein", The Journal of Biological Chemistry, vol. 265, No. 12, Apr. 25, 1990, pp. 6879-6883.
Nguyen, T. et al., "Binding protein BiP is required for translocation of secretory proteins into the endoplasmic reticulum in *Saccharomyces cerevisiae*", Proc. Natl. Acad. Sci., vol. 88, Feb. 1991, pp. 1565-1569.
Xu, P. et al., "Decreased secretion and unfolded protein response up-regulation are correlated with intracellular retention for single-

(56) References Cited

OTHER PUBLICATIONS chain antibody variants produced in yeast", Biotechnology and Bioengineering, vol. 104, No. 1, Sep. 1, 2009, pp. 20-29.
Idiris, A. et al., "Engineering of protein secretion in yeast: strategies and impact on protein production", Appl Microbiol Biotechnol, vol. 86, 2010, pp. 403-417.
Mattanovich, D. et al., "Stress in recombinant protein producing yeasts", Journal of Biotechnology, vol. 113, 2004, pp. 121-135.
Shusta, E. et al., "Increasing the secretory capacity of Saccharomyces cerevisiae for production of single-chain antibody fragments", Nature Biotechnology, vol. 16, Aug. 1998, pp. 773-777.
Cereghino, G. et al., "Applications of yeast in biotechnology: protein production and genetic analysis", Current Opinion in Biotechnology, vol. 10, 1999, pp. 422-427.
Suga, M. et al., "High-efficiency electroporation by freezing intact yeast cells with addition of calcium", Cur. Genet., vol. 43, 2003, pp. 206-211.
Benatuil, L. et al., "An improved yeast transformation method for the generation of very large human antibody libraries", Protein Engineering, Design & Selection, 2010, pp. 1-5.
Orr-Weaver, T. et al., "Yeast transformation: A model system for the study of recombination", Proc. Natl. Acad. Sci., vol. 78, No. 10, Oct. 1981, pp. 6354-6358.
Orr-Weaver, T. et al., "Yeast Recombination: The Association between double-strand gap repair and crossing-over", Proc. Natl. Acad. Sci., vol. 80, Jul. 1983, pp. 4417-4421.
Ma, H. et al., "Plasmid construction by homologous recombination in yeast", Gene, vol. 58, 1987, pp. 201-216.
Chao, G. et al., "Isolating and engineering human antibodies using yeast surface display", Nature Protocols, vol. 1, No. 2, 2006, pp. 755-769.
Rakestraw, J. A. et al., "Secretion-and-capture cell-surface display for selection of target-binding proteins", Protein Engineering, Design & Selection, 2011, pp. 1-6.
Laemmli, U. K., "Cleavage of Structural Proteins during the Assembly of the Head of Bacteriophage T4", Nature, vol. 227, Aug. 15, 1970, pp. 680-685.
Meyer, T. et al., "Use of coomassie brilliant blue R250 for the electrophoresis of microgram quantities of parotid saliva proteins on acrylamide-gel strips", Biochim. Biophys. Acta., vol. 107, 1965, pp. 144-145.
Gultekin, H. et al., "The Use of Polyvinylidenedifluoride Membranes as a General Blotting Matrix", Analytical Biochemistry, vol. 172, 1988, pp. 320-329.
Renart, J. et al., "Transfer of proteins from gels to diazobenzyloxymethylpaper and detection with antisera: A method for studying antibody specificity and antigen structure", Proc. Natl. Acad. Sci., vol. 76, No. 7, pp. 3116-3120.
Mullis, K. et al., "Specific Enzymatic Amplification of DNA In Vitro: The Polymerase Chain Reaction", Cold Spring Harb Symp Quant Biol, vol. 51, 1986, pp. 263-273.
Saiki, R. et al., "Primer-Directed Enzymatic Amplification of DNA with a Thermostable DNA Polymerase", Science, vol. 239, Jan. 29, 1988, pp. 487-491.
Saiki, R. et al., "Enzymatic Amplification of Beta-Globin Genomic Sequences and Restriction Site Analysis for Diagnosis of Sickle Cell Anemia", Science, vol. 230, Dec. 20, 1985, pp. 1350-1354.
Sanger, F. et al., "DNA sequencing with chain-terminating inhibitors", Proc. Natl. Acad. Sci., vol. 74, No. 12, Dec. 1977, pp. 5463-5467.
Murray, V., "Imrpoved double-stranded DNA sequencing using the linear polymerase chain reaction", vol. 17, No. 21, 1989, 1 page.
McCafferty, J. et al., "Phage antibodies: filamentous phage displaying antibody variable domains", Nature, vol. 348, Dec. 6, 1990, pp. 552-554.
Wittrup, D., "Disulfide bond formation and eukaryotic secretory productivity", Current Opinion in Biotechnology, vol. 6, 1995, pp. 203-208.

Boeke, J. et al., "5-Fluoroorotic Acid as a Selective Agent in Yeast Molecular Genetics", Methods in Enzymology, vol. 154, 1987, pp. 164-175.
Veit, B. et al., "Copy Number and Partition of the Saccharomyces cerevisiae 2(mu)m Plasmid Controlled by Transcription Regulators", Molecular and Cellular Biology, vol. 8, No. 11, Nov. 1988, pp. 4949-4957.
Rao, J. et al., "Enhanced secretion and low temperature stabilization of a hyperthermostable and Ca2+-independent (alpha)-amylase of Geobacillus thermoleovorans by surfactants", Letters in Applied Microbiology, vol. 36, 2003, pp. 191-196.
Romanos, M. et al., "Foreign Gene Expression in Yeast: a Review", Yeast, vol. 8, 1992, pp. 423-488.
Kuroda, K. et al., "Efficient Antibody Production upon Suppression of O Mannosylation in the Yeast Ogataea minuta", Applied and Environmental microbiology, vol. 74, No. 2, Jan. 2008, pp. 446-453.
Kronvall, G. et al, "Differences in Anti-Protein A Activity Among IgG Subgroups", The Journal of Immunology, vol. 103, No. 4, Oct. 1969, pp. 828-833.
Jendeberg, L. et al., "Kinetic Analysis of the Interaction Between Protein A Domain Variants and Human Fc Using Plasmon Resonance Detection", Journal of Molecular Recognition, vol. 8, 1995, pp. 270-278.
Boyle, M. et al., "Interaction of Bacterial Fc Receptors with Goat Immunoglobulins", Molecular Immunology, vol. 22, No. 9, 1985, pp. 1115-1121.
Heitzmann, H. et al., "Use of the Avidin-Biotin Complex for Specific Staining of Biological Membranes in Electron Microscopy", Proc. Nat. Acad. Sci. vol. 71, No. 9, Sep. 1974, pp. 3537-3541.
Fukuda, N. et al., "High-efficiency recovery of target cells using improved yeast display system for detection of protein-protein interactions", Appl Microbiol Biotechnol., vol. 76, 2007, pp. 151-158.
Wang, M. et al., "AID upmutants isolated using a high-throughput screen highlight the immunity/cancer balance limiting DNA deaminase activity", Nature Sturctural & Molecular Biology, vol. 16, No. 7, Jul. 2009, pp. 769-777.
Cedergren, L. et al., "Mutational analysis of the interaction between staphylococcal protein A and human IgG1", Protein Engineering, vol. 6, No. 4, 1993, pp. 441-448.
Eliasson, M. et al., "Differential IgG-binding characteristics of staphylococcal protein A, streptococcal protein G, and a chimeric protein AG", The Journal of Immunology, vol. 142, 1989, pp. 575-581.
Langone, J. et al., "Studies on the Interaction between protein A and Immunoglobulin G", The Journal of Immunology, vol. 121, No. 1, Jul. 1978, pp. 327-332.
Langone, J. et al., "Studies on the Interaction Between Protein A and Immunoglobulin G: II. composition and Activity of Complexes Formed Between Protein A. and IgG", The Journal of Immunology, vol. 121, No. 1, 1978, pp. 333-338.
Sjoquist, J. et al., "Protein A Isolated from Staphylococcus aureus after Digestion with Lysostaphin", Eur. J. Biochem., vol. 29, 1972, pp. 572-578.
Mazor, Y. et al, "Isolation of engineered, full-length antibodies from libraries expressed in Escherichia coli", Nature Biotechnology, vol. 25, No. 5, May 2007, pp. 563-565.
Mazor, Y. et al, "E-clonal antibodies: selection of full-length IgG antibodies using bacterial perplasmic display", Nature Protocols, vol. 3, No. 11, 2008, pp. 1766-1777.
Ojala, K. et al., "Improved Display of Synthetic IgG-Binding Domains on the Baculovirus Surface", Technology in Cancer Research Treatement, vol. 3, No. 1, Feb. 2004, pp. 77-84.
Swinney, D. et al., "How were new medicines discovered?", Nature Reviews: Drug Discovery, vol. 10, Jul. 2011, pp. 507-519.
Venter, J. et al., "The Sequence of the Human Genome", The Human Genome, Science, vol. 291, Feb. 16, 2001, 49 pages.
Futreal, P. et al., "BRCA1 Mutations in Primary Breast and Ovarian Carcinomas", Science, vol. 266, Oct. 7, 1994, pp. 120-122.
Miki, Y. et al., "A Strong Candidate for the Breast and Ovarian Cancer Susceptibility Gene BRCA1", Science, New Series, vol. 266, No. 5182, Oct. 7, 1994, pp. 66-71.

(56) References Cited

OTHER PUBLICATIONS

Munos B., "Lessons from 60 years of pharmaceutical innovation", Nature Reviews: Drug Discovery, vol. 8, Dec. 2009, pp. 959-968.
Dimasi, J. et al., "The price of innovation: new estimates of drug development costs", Journal of Health Economics 22, 2003, pp. 151-185.
Scannell, J. et al., "Diagnosing the decline in pharmaceutical R&D efficiency", Nature Reviews: Drug Discovery, vol. 11, Mar. 2012, pp. 191-200.
"Research and Development in the Pharmaceutical Industry", A CBO Study, Oct. 2006, 65 pages.
Beckman, R. et al., "Antibody Constructs in Cancer Therapy, Protein Engineering Strategies to Improve Exposure in Solid Tumors", American Cancer Society, Dec. 11, 2006, pp. 170-178.
Porro, D. et al., "Recombinant Protein Production in Yeasts", Molecular Biotechnology, vol. 31, 2005, pp. 245-259.
Sudbery, P., "The expression of recombinant proteins in yeasts", Current Opinion in Biotechnology, vol. 7, 1996, pp. 517-524.
Benson, J. et al., "Validating cancer drug targets", Nature, vol. 441, May 25, 2006, pp. 451-456.
Klapper, L. et al., "Biochemical and Clinical Impolications of the ErbB/HER Signlaing Network of Growth Factor Receptors", Advances in Cancer Research, 2000, pp. 25-79.
Huang, S. et al., "Epidermal growth factor receptor inhibition in cancer therapy: biology, rationale and preliminary clinical results" Investtigational New Drugs, vol. 17, Feb. 1999, pp. 259-269.
Huang, S. et al., "Epidermal Growth Factor Receptor Blockade with C225 Modulates Proliferation Apoptosis, and Radiosensitivity in Squamous Cell Carcinomas of the Head and Neck", Cancer Research, vol. 59, Apr. 15, 1999, pp. 1935-1940.
Sato, J. et al., "Biological Effects in Vitro of Monoclonal Antibodies to Human Epidermal Growth Factor Receptors", Molecular Biology Medicine, vol. 1, 1983, pp. 511-529.
Salomon, D. et al., "Epidermal growth factor-related peptides and their receptors in human malignancies", Critical Reviews on Oncology/Hematology, vol. 19, 1995, pp. 183-232.
Baselga, J., "The EGFR as a target for anticancer therapy-focus on cetuximab", European Journal of Cancer, vol. 37, 2001, pp. S16-S22.
Imai, K. et al., "Comparing antibody and small-molecule therapies for cancer", Nature, vol. 6, Sep. 2006, pp. 714-727.
Thurber, G. "Factors determining antibody distribution in tumors", Trends in Pharmacological Sciences, vol. 29, No. 2, 2007, pp. 57-61.
Roopenian, D. et al., "FcRn: the neonatal Fc receptor comes of age", Nature Reviews: Immunology, vol. 7, Sep. 2007, pp. 715-725.
Carter, P., "Potent antibody therapeutics by design", Nature Reviews: Immunology, vol. 6, May 2006, pp. 343-357.
Goldberg, R., "Hot Drugs: Cancer", Nature, May 2005, pp. S10-S110.
Baselga, J., "Targeting Tyrosine Kinases in Cancer: The Second Wave", Science, vol. 312, May 26, 2006, 5 pages.
Huang, S. et al., "Dual-Agent Molecular Targeting of the Epidermal Growth Factor Receptor (EGFR): Combining Anti-EGFR Antibody with Tyrosine Kinase Inhibitor", Cancer Research, vol. 64, Aug. 1, 2004, pp. 5355-5362.
Iannello, A. et al., "Role of antibody-dependent cell-mediated cytotoxicity in the efficacy of therapeutic anti-cancer monoclonal antibodies", Cancer and Metastasis Reviews, vol. 24, 2005, pp. 487-499.
Nakamura, A. et al., "Fc Receptor Targeting in the Treatment of Allergy, Autoimmune Diseases and Cancer", Multichain Immune Recognition Receptor Signaling: From Spatiotemporal Organization to Human Disease, 2008, pp. 220-233.

Yalow, R. et al., "Assay of Plasma Insulin in Human Subjects by Immunological Methods", Radiobiology: Nature, vol. 184, No. 4699, Nov. 21, 1959, pp. 1648-1649.
Weeman, B.K. et al., "Immunoassay using antigen-enzyme conjugates", FEBS Letters, vol. 15, No. 3, Jun. 1971, pp. 232-236.
Orden, D., "Enzyme-linked immunosorbent assay (ELISA) Quantitative assay of immunoglobulin G", Immunochemistry, vol. 8, 1971, pp. 871-874.
Filpula, D., "Antibody engineering and modification technologies", Science Direct, Biomolecular Engineering, vol. 24, 2007, pp. 201-215.
Nimmerjahn, F. et al., "Fc receptors as regulators of immune responses" Nature, vol. 8, Jan. 2008, pp. 34-47.
Idusogie, E. et al., "Mappling of the C1q Binding Site on Rituxan, a Chimeric Antibody with a Human IgG1 Fc", The Journal of Immunology, vol. 164, 2000, pp. 4178-4184.
Natsume, A. et al., "Improving effector functions of antibodies for cancer treatment: Enhancing ADCC and CDC", Drug Design Development and Therapy, 2009, pp. 7-16.
Brambell, F. W., "The Transmission of Immunity from Mother to young and the Catabolism of Immunoglobulins", The Lancet, Nov. 19, 1966, pp. 1087-1093.
Kohler, G. et al., "Continuous cultures of fused cells secreting antibody of predefined specificity", Nature, vol. 256, Aug. 7, 1975, pp. 495-497.
Yuan, F. et al., "Does Hybridoma Technology Still have a place in Transfusion Medicine?", Transfusion Medicine Reviews, vol. 16, No. 3, Jul. 2002, pp. 230-238.
Worn, A. et al., "Stability Engineering of Antibody Single-chain Fv Fragments", Journal of Molecular Biology, vol. 305, 2001, pp. 989-1010.
Chames, P. et al., "Therapeutic antibodies: successes, limitations and homes for the future", British Journal of Pharmacology, vol. 157, 2009, pp. 220-233.
Holliger, P. et al., "Engineered antibody fragments and the rise of single domains", Nature Biotecnology, vol. 23, No. 9, Sep. 2005, pp. 1126-1136.
Bird, R. et al., "Single-Chain Antigen-Binding Proteins", Science, vol. 242, pp. 423-426.
Konermann, R., "Alternative antibody formats", Current Opinion in Molecular Therapeutics, vol. 12, No. 2, 2010, pp. 176-183.
Wesolowski, J. et al., "Single Domain antibodies: promising experimental and therapeutic tools in infection and immunity", Med Microbiol Immunol, vol. 198, 2009, pp. 157-174.
Holliger, P. et al., "Diabodies': Small bivalent and bispecific antibody fragments", Proc. Natl. Acad. Sci., vol. 90, Jul. 1993, pp. 6444-6448.
Todorovska, A. et al., "Design and application of diabodies, triabodies and tetrabodies for cancer targeting", Journal of Immunological Methods, vol. 248, 2001, pp. 47-66.
Hamers-Casterman, C. et al., "Naturally occurring antibodies devoid of light chains", Nature, vol. 363, Jun. 3, 1993, pp. 446-448.
Muyldermans, S., "Single Domain camel antibodies: current status", Reviews in Molecular Biotechnology, vol. 74, 2001, pp. 277-302.
Genst, E. et al., "Antibody repertoire development in camelids", Developmental and Comparative Immunology, vol. 30, 2006, pp. 187-198.
Simmons, D. et al., "Dimerisation strategies for shark IgNAR single domain antibody fragments", Journal of Immunological Methods, vol. 315, 2006, pp. 171-184.
Wu, T. et al., "Length Distribution of CDRH3 in Antibodies", Proteins: Structure, Function and Genetics, vol. 16, 1993, pp. 1-7.

\* cited by examiner

Display of the
Fc binding domain

• Display of the
  Fc binding domain
• Soluble secretion
  of VHH-Fc

• No display of the Fc
  binding domain
• Soluble secretion into
  the culture supernatant M: Protein marker
1: Negative control
2: SD
3: SG, 6 h
4: SG, 16 h
5: SG, 24 h
6: SG, 30 h
7: SG, 48 h M: Protein marker
1: Negative control
2: APO-E clone 1
3: APO-E clone 2
4: APO-E clone 3
5: APO-E clone 4
6: APO-E clone 5
7: APO-E clone 6

FIG. 12
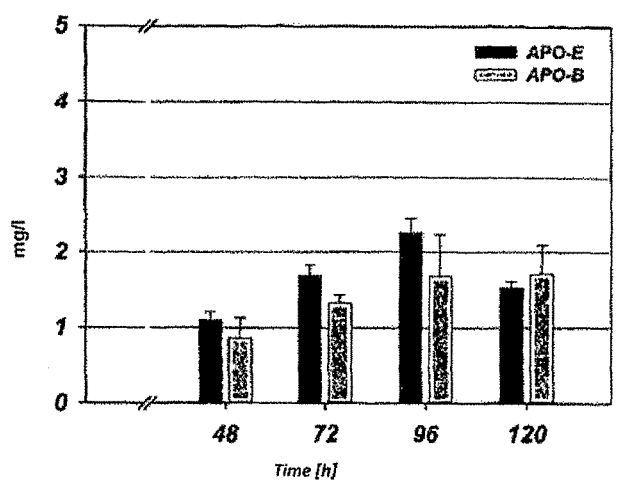
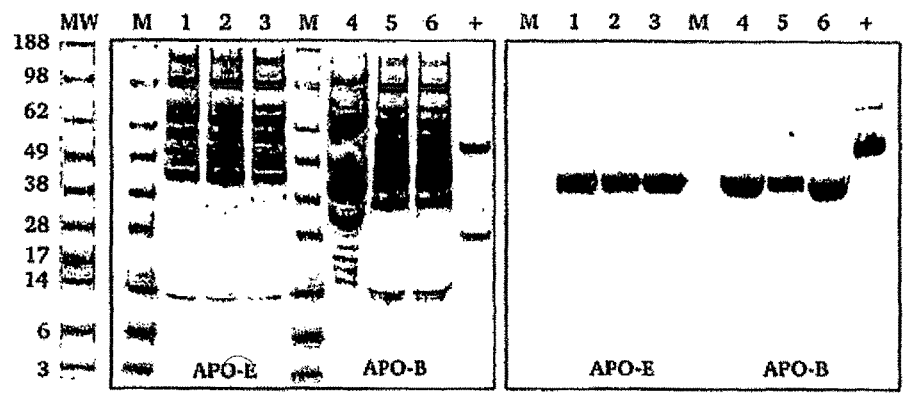
FIG. 13A
FIG. 13B

FIG. 14A
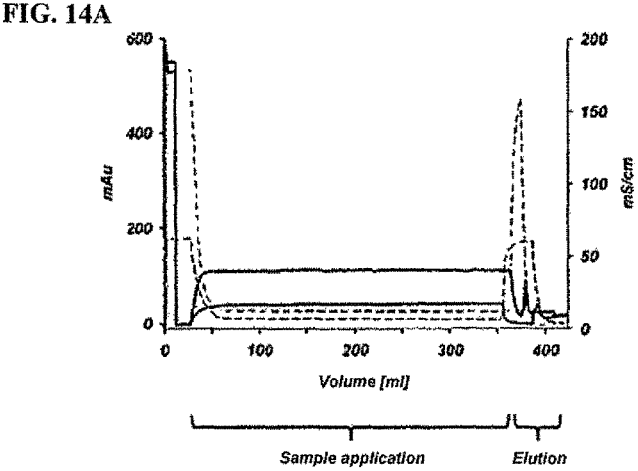
FIG. 14B
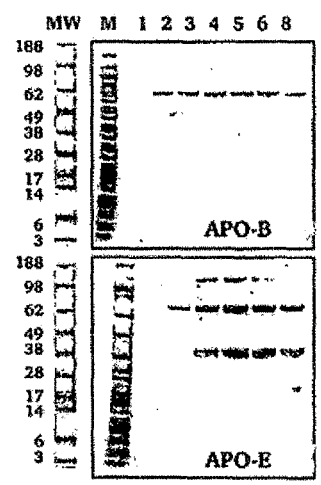
FIG. 14C
FIG. 15
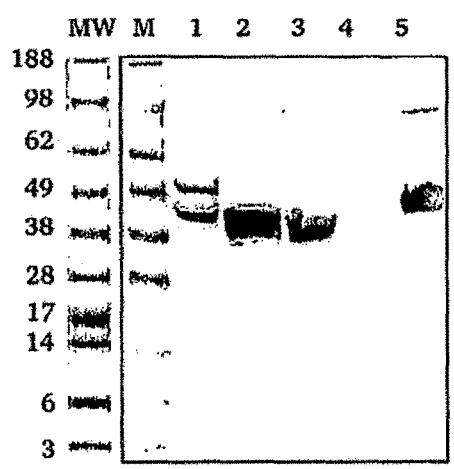
M: Protein marker
1: Lysate
2: Supernatant before dialysis
3: Supernatant after dialysis
4: Breakthrough
5: Positive control

| | Mean rel. fluorescence | % cells (M1) |
|---|---|---|
| Aga2p | 11.5 | 0.7 % |
| Aga2p-Z | 370.7 | 66.8 % |
| Aga2p-ZZ | 636.3 | 65.7 % |

| | Mean rel. fluorescence | % cells (M1) |
|---|---|---|
| Aga2p | 7.8 | 0.5 % |
| Aga2p-Z | 253.0 | 64.0 % |
| Aga2p-ZZ | 445.1 | 68.0% |

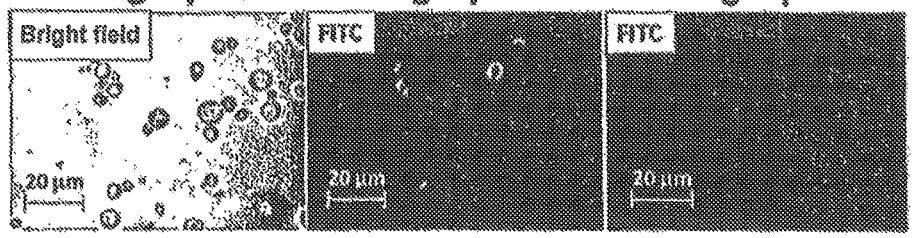
FIG. 22A Aga2p-ZZ  FIG. 22B Aga2p-ZZ  FIG. 22C Aga2p
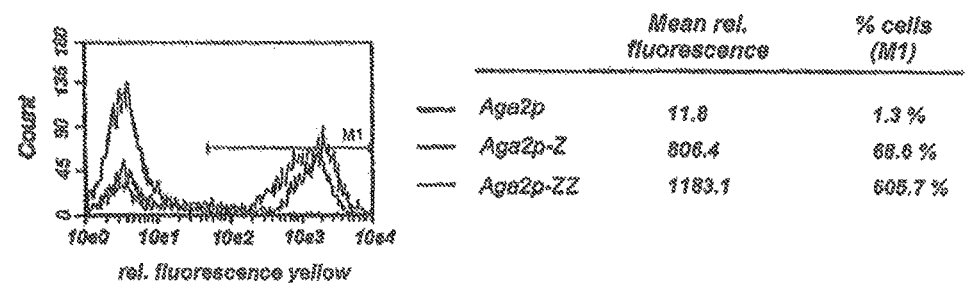
FIG. 23
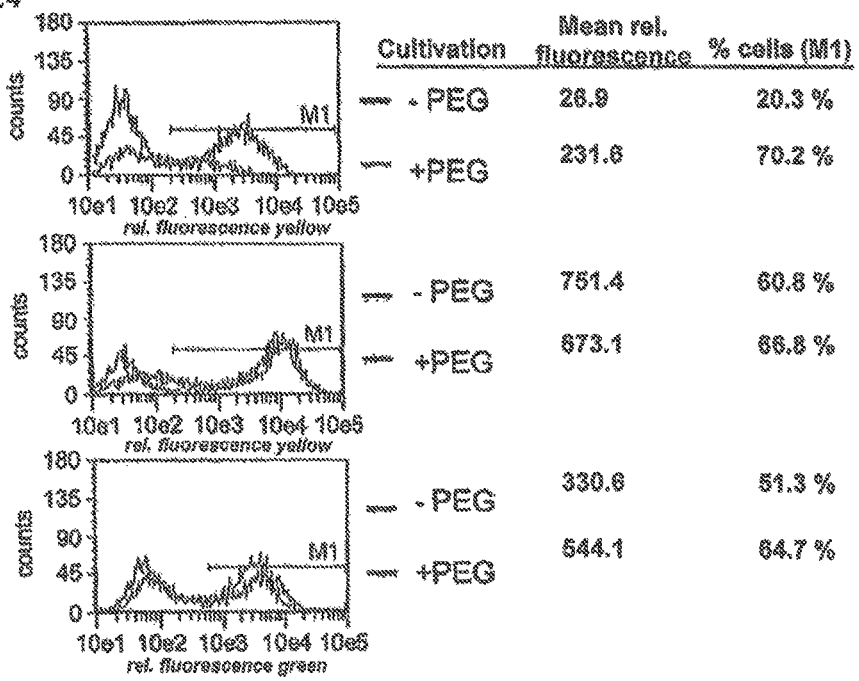
FIG. 24

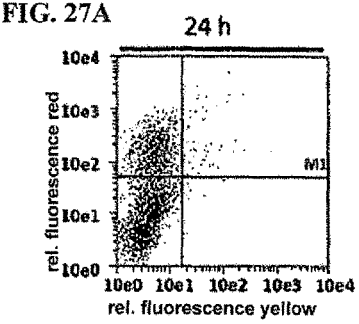
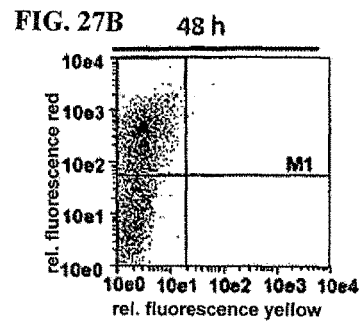
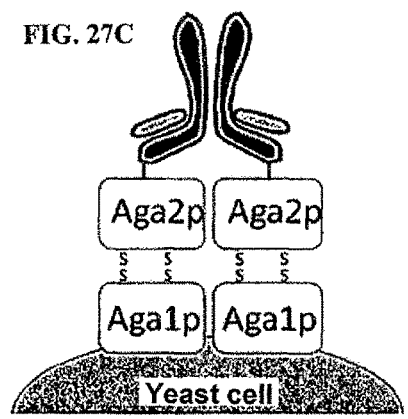
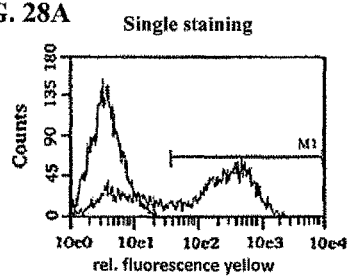
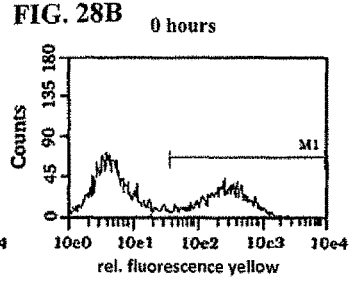
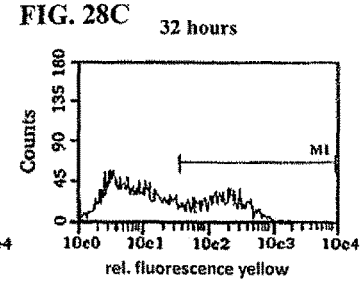

M: Protein marker
1: VHH-Fc, pGal1
2: VHH-Fc, pGAPDH
3: VHH-Fc, pGal1
4: VHH-Fc, pGAPDH
5: VHH-Fc, pGal1
6: VHH-Fc, pGAPDH

METHOD OF PRODUCING SECRETABLE ANTIBODIES BY EXPRESSION IN SACCHAROMYCES CEREVISIAE

SUBJECT MATTER OF THE INVENTION

The invention relates to a method for the production and non-covalent surface display of antibodies and derived fragments as well as molecule libraries based thereon on the surface of S. cerevisiae cells. The non-covalent manner of the surface display renders possible the selection of specific variants by means of high throughput screening and the subsequent switchable secretion of the selected binding molecule into the culture supernatant for biochemical characterisation.

The invention also relates to methods for displaying antibodies or antibody libraries on the surface of yeast cells and screening of these libraries for immunoglobulins having particular desired properties.

BACKGROUND OF THE INVENTION

The discovery of monoclonal antibodies has evolved from hybridoma technology, with the aid of which antibodies having a particular specificity and affinity can be produced in a specific manner. Combinatorial libraries developed therefrom, including screening and selection methods, have developed into standard tools for modifying the binding properties of proteins in general.

The most widespread technique for generating and screening antibody libraries was and in some cases still is the "phage display" method, in which the particular protein of interest can be expressed as a fusion polypeptide on a bacteriophage shell protein and selected by binding to immobilised or soluble biotinylated ligands. A phage which has been constructed in this manner can be regarded as a compact genetic unit which has combined in itself both the phenotypic and the genotypic properties. Phage display has been used very successfully on antibodies, antibody fragments, enzymes, DNA-binding proteins etc. Antibodies which have desired binding properties are selected by binding to an immobilised antigen in a process called "panning". Phages which contain non-specific antibodies are washed out and the bound phages are detached and amplified in E. coli. This set-up has been employed to generate a large number of antigen-specific antibodies. Nonetheless, phage display technology has some fundamental deficiencies and difficulties which limit its use, in particular in the production of eukaryotic proteins. Thus, for example, antibodies of very high affinity can be isolated and further processed by "panning" only with difficulty. In addition, posttranslational modifications, such as e.g. glycosylation, which can influence the specificity and affinity of the antibody, are not possible with phage display methods.

An alternative is the use of lower eukaryotic systems, such as yeast. The structural similarity between B cell-displaying antibodies and yeast cell-displaying antibodies deliver a closer analogy to in vivo "affinity maturation" than in the case of filamentous phages. Since in particular eukaryotic cells, such as yeast, are capable of producing glycosylated proteins, whereas filamentous phages cannot do this, monoclonal antibodies from eukaryotic host cells should have properties which resemble human or mammalian antibodies more so than antibodies from phages. Moreover, cloning, expression and modification of antibodies in yeast in particular has proved to be effective and simple in terms of method and practicality. U.S. Pat. No. 6,699,658 describes, for example, a yeast cell surface display method with the aid of which screening and production of combinatorial antibody libraries has become possible. The said "yeast surface display" technology is based on the transfection of yeast cells with vectors which express an immunoglobulin fused to a yeast cell wall protein, employing mutagenesis in order to generate a diversity of immunoglobulin mutants and in order then to select these cells according to the desired phenotypic properties. This technology was established in 1997 by Boder and Wittrup. They succeeded for the first time in displaying scFv fragments of a combinatorial library functionally on the surface of yeast cells and in screening them by flow cytometry, and in isolating scFv fragments having an increased affinity for the antigen. This was rendered possible by the stable coupling of geno- and phenotype, since the scFv fragment was displayed as a fusion protein having a cell wall protein intrinsic to the yeast. Presumably the most important achievement arrived at by using yeast-based display technology is the direct applicability of fluorescence-activated cell sorting (FACS), which is decisive in the efficient screening of large variant libraries. A stable genotype-phenotype coupling is achieved by fusion of a heterologous protein with proteins of the outer cell wall of S. cerevisiae. The exposure of the protein thereby achieved is the prerequisite for interaction with antigens.

However, the yeast surface display just described, as developed by Wittrup and Boder, has in particular some practical disadvantages. One disadvantage is, for example, that the various proteins expressed cannot be obtained or can be only obtained unsatisfactorily with the same yeast cell. Furthermore, by the method of Wittrup the desired immunoglobulin is bound covalently to the cell wall protein and must be isolated by additional method steps.

WO 2010/005863 describes a corresponding yeast surface display system based on yeast cells of the genus Pichia pastoris, in which the immunoglobulin is bound non-covalently to the ZZ domain of protein A, wherein the fusion protein comprising the cell wall protein agglutinin or its subunits and the ZZ domain and the immunoglobulin is only expressed and secreted simultaneously in the yeast cell, in order to be displayed on the cell surface, when corresponding various promoters for expression of said proteins are switched on or off in the correct chronological order.

SUMMARY OF THE INVENTION

The invention relates to the development of a method for non-covalent surface display of antibodies and derived fragments as well as molecule libraries based thereon on the surface of cells of the yeast species S. cerevisiae. The non-covalent manner of the surface display is intended to render possible the selection of specific variants by means of high throughput screening and the subsequent switchable secretion of the selected binding molecule into the culture supernatant for biochemical characterisation.

The focal point is successful combination of selection and production with the time-saving omission of subclonings and reformatting steps, such as is necessary in the known comparable methods, such as e.g. surface display of proteins on phages. This combination results in a simplification and acceleration of subsequent processes in the active ingredient discovery of antibodies. By the use, known per se, of an Fc binding domain, preferably the ZZ domain from Staphylococcus aureus protein A, as the mediator of surface display, antibodies, biologically active antibody fragments and antibody domains, such as, for example, VHH-Fc fusion proteins (consisting of two protein chains) can be successfully displayed on yeast cells.

Surprisingly, by using the yeast *S. cerevisiae* as the host organism the correct folding, secretion and stability of the protein is already selected during the surface display, since as a eukaryote this yeast has mechanisms of quality control during protein synthesis. By the method presented here it is possible to display VHH-Fc fusion proteins and more complex proteins, such as whole antibodies, on the surface of yeast cells in their final format specific for their use, and in this way to be able to use methods of protein engineering. Thereafter, the selected clone can be used directly for production of the protein.

The invention thus provides a method for producing a diversity of IgG molecules, such as antibodies, biologically active antibody fragments or antibody domains having particular properties, by expression, secretion and presentation thereof on the surface of yeast cells, wherein the method according to the invention comprises the following steps:

(a) providing host cells of the yeast species *Saccharomyces cervisiae* which have been transfected with a first and a second nucleic acid molecule in the form of suitable plasmids, wherein the first nucleic acid molecule codes for a fusion protein which substantially comprises a cell surface anchor protein, an Fc binding domain and a regulatable promoter which controls the expression of the fusion protein as a function of the cultivation conditions, and the second nucleic acid molecule codes for said population of antibodies, said antibody fragments or antibody domains in the form of their light and heavy chains and is under the control of a permanently active promoter, (b) expressing the fusion proteins with simultaneous co-expression of the diversity of antibodies, antibody fragments or antibody domains in the yeast cells in the presence of polyethylene glycol (PEG) having a molecular weight of >5,000 in the cultivation medium, wherein said IgG molecules and also the fusion protein are secreted from the yeast cell in soluble form, (c) displaying on the surface of the yeast cells the diversity of antibodies, antibody fragments or antibody domains which are bound in non-covalent form to the Fc binding domain of the expressed fusion protein anchored to the cell surface, (d) selecting and isolating, with the aid of detection markers, which are bound to the fusion protein or the Ig molecule or contained in it, yeast cells according to desired different phenotypic or binding properties of the diversity of antibodies, biologically active antibody fragments or antibody domains bound to the Fc binding domain, (e) expressing the diversity of antibodies, biologically active antibody fragments or the antibody domains in the particular selected yeast cell population under cultivation conditions which allow no or no substantial further expression of the fusion protein, and (f) isolating the diversity of antibodies having the selected phenotypic or binding properties from the culture medium.

In contrast to this, in the method according to WO 2010/0058863 the expression of the fusion protein, which is identical per se, and of the immunoglobulin in *Pichia pastoris* does not proceed simultaneously: rather, the system works effectively to some degree only if the expression of the cell surface "capture" molecule is induced and operated by activation of the promoter responsible, without a noticeable expression of the light and heavy chains of the immunoglobulin taking place simultaneously. This is achieved only in a second step, after the expression of the capture molecule has ceased due to inhibition via the regulatable promoter.

Surprisingly, this is not necessary in the method according to the invention. While the promoter for the Fc binding domain is initially activated, the expression of the Ig molecule can already take place simultaneously. When Fc binding domain has been sufficiently expressed and secreted in the yeast cell, in order to be finally bound to the cell surface and with simultaneous co-expression and co-secretion of Ig, after the promoter for the Fc binding domain has been switched off the expression of the Ig molecules continues to take place and these are non-covalently bound to free Fc binding domains after their secretion. This is all the more surprising since in WO 2010/0058863 in principle the same or a very similar cell wall surface protein, as the anchor protein, and the same Fc binding domain (ZZ domain) are employed. The difference in the method according to the invention thus appears to lie in the different yeast species (*S. cerevisiae* compared with *P. pastoris*) and in the use of higher molecular weight polyethylene glycol. It has been found that the use of PEG having a molecular weight of >5,000, in particular >6,000, in particular >7,000 and preferably >8,000 leads to a significant increase in the Ig molecules to be encountered on the cell surface, which presumably is accompanied by an increased secretion by PEG. Surprisingly, if PEG is omitted or PEG having a lower molecular weight (<5,000, in particular <7,000, in particular <8,000) is employed an insufficient number of bound Ig molecules is observed on the cell surface, which perhaps also explains the difference from the method of WO 2010/005863. Generally, the secretion and surface display of in particular whole Ig molecules on *S. cerevisiae* has hitherto proved to be complicated.

In contrast to the method from WO 2010/005863, in the present method according to the invention only the expression of a protein, namely the fusion protein of the cell wall protein and the Fc binding domain, has to be regulated, preferably by the GAL1 promoter, whereas the IgG molecule, for example the VHH-Fc fusion protein, is expressed permanently, that is to say constitutively, regardless of the expression of the other protein which the Fc binding domain comprises.

According to the invention agglutinin, in particular α-agglutinin, is employed as the cell wall anchor protein. This binds with its subunit aga1p directly to the cell wall. The fusion protein according to the invention which is expressed in the yeast cell and binds to aga1p via disulphide bridges comprises the second subunit of agglutinin, aga2p, which is bound C-terminally to the ZZ domain from protein A.

The invention thus also provides a corresponding method in which the cell surface anchor protein is α-agglutinin or alpha-agglutinin and the fusion protein comprises aga2p and an Fc binding domain, preferably the ZZ domain of protein A from *Staphylococcus aureus*.

The invention thus provides in particular a method in which the expression (and secretion) of the fusion protein of the ZZ domain and aga2p is regulated by the GAL1 promoter.

The invention also provides in particular a method in which the expression (and secretion) of the antibodies, antibody fragments or antibody domains is under the control of the GAPDH promoter, wherein the expression takes place constitutively for expression of the fusion protein of the ZZ domain and aga2p subunit.

The invention furthermore provides a corresponding method in which in the expression/secretion PEG having a molecular weight >5,000, in particular >7,000-8,000, preferably PEG8000 is employed in the expression medium.

Finally, the invention provides a corresponding method for production of an antibody library for generation and selection of whole antibodies, Fab fragments or other biologically active antibody domains having selected phenotypic or binding properties.

DETAILED DESCRIPTION OF THE INVENTION

In general, the immunoglobulins which are employed in the method according to the invention are IgG, IgA, IgE or IgM molecules, but preferably IgG molecules, which include IgG1, IgG2, IgG3 and IgG4.

The term "transfecting", "transfection", "transforming" or "transformation" is used synonymously and according to the invention means the introduction of heterologous nucleic acid (DNA/RNA) into a eukaryotic cell, in particular yeast cells.

According to the invention, antibody fragments are understood as meaning functional parts of preferably monoclonal antibodies, such as Fc, Fab, Fab', Fv, F(ab')2, scFv. According to the invention, corresponding biological active fragments are to be understood as meaning those parts of antibodies which are capable of binding to an antigen, such as Fab, Fab', Fv, F(ab')2, and scFv.

According to the invention, an Fc binding domain is understood as meaning a molecule or part of a molecule, preferably a protein or polypeptide, which is capable of binding covalently or non-covalently to an Fc part of an antibody or regions thereof. According to the invention, the Fc binding domain preferably binds non-covalently to the Fc part of an antibody or immunoglo The method presented in this application for non-covalent surface display on yeast cells has been successfully used for surface display of VHH-Fc proteins and IgG molecules. The stability of the non-covalent interaction between the ZZ domains and Fc part guaranteed a sufficiently stable genotype-phenotype coupling and in this way rendered possible the use of the method in the concentration of target cells within various mixtures. Future uses of the method lie e.g. in the screening of libraries of IgG molecules or diverse Fc fusion proteins for identification of proteins having desired properties in the field of protein engineering. The use of a library which is known to contain variants which meet the desired functional demands is of advantage here. Since even tiny differences in the affinities of VHH domains can be portrayed within the method during the surface display, this method is particularly suitable for affinity maturation of antibodies with subsequent soluble production and biophysical characterisation.

For simplification of the method, the use of alternative anchor proteins for surface display of the ZZ domain can be tried out, since as a result the use is no longer limited to the use of the yeast strain EBY100. Many cell wall proteins from *S. cerevisiae* are suitable in principle for surface display of heterologous proteins. Numerous examples are described for this in the literature[93,99]. The use of a different anchor protein renders possible an independent choice of the expression strain, since a strain with chromosomal integration of the Aga1 expression cassette, such as EBY100, no longer necessarily has to be used. This additionally opens up the possibility of generating and using an expression strain suitable for specific demands of the heterologous protein.

The plasmid constructions according to the invention are shown in FIGS. 36 to 39. These generally provide only examples or preferred example of plasmids and plasmid constructions and can be exchanged for others or variants thereof at any time by the person skilled in the art, as long as the corresponding DNA sequences essential to the invention are employed and initiate the desired functions.

Furthermore, it may prove advantageous to integrate the ZZ domain into the yeast genome in a stable manner in order to render possible a more flexible choice of markers for the soluble secretion and an easier generation of molecule libraries. To increase the secretion efficiency a further strain manipulation is advisable, since overexpression solely of the oxidoreductase PDI has not led to the desired protein yields. Overexpression of further ER-located proteins involved in the secretion, such as e.g. Ero1p, is possibly necessary in order to achieve the desired protein yields.

*Staphylococcus aureus* Protein A

On the surface of bacteria there are to be found, inter alia, proteins which can bind to immunoglobulins with a high affinity[61]. They differ in their specificity with respect to the host species and the immunoglobulin classes which they can bind. The bacteria are predominantly pathogenic representatives of the genera *Staphylococcus* and *Streptococcus*. The biological function of the surface proteins comprises masking of the bacterial cell with proteins intrinsic to the host, in order to evade the host's immune system[62]. One of the best known immunoglobulin-binding bacterial surface proteins is *Staphylococcus aureus* protein A, called SpA. It is used in biotechnology for affinity purification of IgG molecules and Fc fusion proteins and is composed of five domains, which all contribute towards the IgG binding and also individually still have IgG binding properties. The binding of IgG molecules takes place chiefly via the Fc part. Binding of SpA to Fab fragments has furthermore been demonstrated[64]. The domain structure of SpA is shown in FIG. 1. In addition to the five domains of high sequence homology (E, D, A, B and E), there are also two further domains (X and M) which mediate the anchoring of SpA in the bacterial cell wall, and an N-terminal signal peptide (SP), which navigates SpA to the cell wall. The binding of SpA to Fc parts is pH-dependent[61]. The strongest binding exists at a pH of 8[66]. As already mentioned, domains E, D, A, B and E can also individually mediate the binding to Fc parts and Fab fragments. Advantages in particular with respect to biotechnological use of these domains emerge as a result. Due to the smaller size compared with SpA, recombinant production of the individual domains is simplified compared with SpA. An artificial domain is derived from domain B and was generated in 1987 by Nilsson and colleagues by an amino acid substitution at position 29[67]. It is called the Z domain and displays an increased chemical stability. In addition a loss in the binding of the Z domain to Fab fragments was achieved by the amino acid substitution mentioned. As a result the Z domain binds the IgG molecules exclusively via the Fc part[68]. Like domain B, the Z domain also takes up a structure of three α-helices[69, 70]. By using a duplicated Z sequence (ZZ domain), a stronger binding of the ZZ domain compared with the Z domain is achieved for Fc parts. The ZZ domains is a divalent molecule by which means the Fc binding is intensified compared with the monovalent Z domain due to an avidity effect[71].

Surface Display on Yeast Cells

The exposure of protein and peptide libraries on the surface of yeast cells is used as a technique for directed evolution of proteins and is called "yeast surface display" in the literature. This technology was established in 1997 by Boder and Wittrup[92]. They succeeded for the first time in displaying scFv fragments of a combinatorial library functionally on the surface of yeast cells and in screening them by flow cytometry, and in isolating scFv fragments having an increased affinity for the antigen[92]. This was rendered possible by the stable coupling of geno- and phenotype, since the scFv fragment was displayed as a fusion protein with a cell wall protein intrinsic to the yeast. Presumably the most important achievement arrived at by using yeast-based display technology is the direct applicability of fluorescence-activated cell sorting (FACS), which is decisive in the efficient screening of large variant libraries. A stable genotype-phenotype coupling is achieved by fusion of a heterologous protein with proteins of the outer cell wall of S. cerevisiae. The exposure of the protein thereby achieved is the prerequisite for interaction with antigens. Many different cell wall proteins are in principle capable of exposing heterologous proteins and peptides as fusion partners, e.g. α-agglutinin and α-agglutinin, Cwp1p and Flo1p[93,94]. Among all these proteins, the α-agglutinin system has particularly become established. This system is currently used in the selection of antibodies from naïve, immunised and synthetic antibody libraries. In 2003 Feldhaus and colleagues demonstrated the selection of scFv variants of high affinity from a non-immunised human variant library displayed on the surface of Saccharomyces cerevisia[95]. It was also possible for affinity maturation of antibody fragments to be successfully demonstrated by surface display of Fab fragments on yeast cells[96]. The system established in 1997 by Boder and Wittrup for surface display on yeast cells by means of α-agglutinin is explained in more detail in the following section.

a-Agglutinin System

Agglutinins are paired type-specific adhesion proteins of the outer cell wall of S. cerevisiae and mediate cell-cell adhesion between haploid yeast cells of complementary paired type during fusion of these cells to the dipolide zygote. This process is called mating in the literature. Yeast cells with the paired type a express α-agglutinin and yeast cells with the paired type α express α-agglutinin[97]. The cell wall protein α-agglutinin is built up from the subunits Aga1p and Aga2p. The subunit Aga1p has a GPI anchor signal and mediates the fixing of the proteins in the extracellular matrix of the cell wall by covalent binding of β-glucan[98]. The subunit Aga2p is likewise secreted by the cell and is bonded to Aga1p via two disulphide bridges. For exposure of heterologous proteins using the α-agglutinin system, the protein to be displayed is as a rule cloned into a corresponding expression vector as a C-terminal fusion with the subunit Aga2p. The recombinant construct translated after the induction of the gene expression and displayed on the surface is shown in diagram form in FIG. 2. AGA1 (Aga1p) is expressed by a chromosomally integrated galactose-inducible expression cassette. By the association of Aga1p and Aga2p the heterologous protein is exposed covalently on the surface of the yeast cell and can be detected by flow cytometry with the aid of its binding properties or by means of affinity epitopes (FIG. 2). For the expression, secretion and surface display of diverse proteins, during the present work the "pYD1 Yeast Display Vector Kit" (Invitrogen) was commercially obtainable.

Saccharomyces cerevisiae as an Expression System

Recombinant proteins have already been successfully produced in various host organisms. These include prokaryotic expression systems, such as E. coli[100], and also eukaryotic expression systems, such as mammalian cells[101]. Saccharomyces cerevisiae is likewise suitable for expression of heterologous proteins, also because it is the best-characterised eukaryotic host organism which has been used in particular since genome sequencing in 1996 as a model organism for investigation of eukaryotic cell functions. As a single-cell organism it is less complex than other eukaryotic systems and its cultivation in a defined medium is possible, as a result of which good control of the growth conditions and a significant reduction in cultivation costs is possible[104]. The comparatively short life cycle with a generation time of approx. 90 minutes is a further reason for the preferred use of the yeast S. cerevisiae[102]. As a single-cell organism the yeast combines both the advantages of microbiological expression systems due to the simple cultivation and the use of industrial fermentation methods, and the advantages of eukaryotic expression systems due to the presence of eukaryotic expression and secretion pathways in the cell. Furthermore, a large selection of yeast vectors is available, which renders possible genetic manipulation[105]. Compared with other yeasts, such as e.g. Pichia pastoris, S. cerevisiae is often attributed a lower secretion efficiency, for which reason it is often not favoured industrially as a host organism for the production of heterologous proteins[106]. The importance of the yeast S. cerevisiae as a host organism for the expression of heterologous antibody molecules is shown in the following section.

Antibody Expression in Saccharomyces Cerevisiae

For a biochemical and biophysical characterisation e.g. by means of immunoprecipitation, ELISA or biolayer interferometry, it is necessary to produce the recombinant proteins in a sufficient quantity. A large number of production systems which achieve a sufficient yield of a soluble antibody or antibody fragment already currently exists. These expression systems are e.g. mammalian cells, the fission yeast Pichia pastoris, insect cells or E. coli[107-109]. The expression of antibodies in S. cerevisiae has for a long time proved to be less suitable, since the yields were often too low for further uses. For IgG molecules yields of only 50 µg/l were achieved[110]. By an evolutive approach Rakestraw and colleagues succeeded in 2009 in significantly increasing the secretion of scFv fragments and IgG molecules from S. cerevisiae. By screening a variant library for the signal peptide MFα1p, mutants which increased the secretion of scFv fragments from S. cerevisiae 16-fold compared with the wild-type sequence were identified[111]. Using the same approach in combination with manipulation of the yeast strain it was even possible to increase the secretion of a functional IgG molecule 180-fold[111]. This finding demonstrates the relevance of the signal peptide used for the secretion of heterologous proteins in yeast cells. This circumstance is of particular importance in industrial processes in which a sufficient secretion is important for simplification of subsequent process steps[10]. The choice of the suitable yeast strain is also decisive. By genetic manipulation of expression strains it is possible to increase the secretion output of a strain for expression of heterologous antibody molecules. In this connection proteins which are associated with the secretion path of the yeast are important. These are e.g. enzymes such as the oxidoreductase PDI (protein disulphide isomerase), which is involved in the reduction and oxidation of disulphide bridges, and HSP70 chaperones, such as BiP (binding immunoglobulin protein), which is involved in the folding of secretory proteins[112]. It is presumed that BiP binds immature protein in the endoplasmic reticulum (ER) and in this way prevents the formation of aggregates. By mutant analyses it was possible to show that a depletion of BiP leads to aggregation of the immature protein and to this remaining in the ER[113]. From this there then follows in general the induction of the UPR (unfolded protein response)[114] and the proteolytic degradation of the protein by means of ERAD (ER associated protein degradation)[115], the blockade of protein synthesis and the activation of chaperone-coding genes[116]. The conclusion can be drawn that the mechanism of quality control in the ER is one of the most critical bottlenecks during soluble secretion of heterologous proteins in yeast cells[117]. By overexpression of folding assistants such as PDI and BiP, it was possible to show that it was possible to increase the secretion of an scFv fragment in *S. cerevisiae* ten-fold[106, 118]. Nevertheless, it is pointed out in the literature that whether a protein to be secreted benefits from overexpression of PDI and BiP depends greatly on the properties of the specific protein, and that there are proteins which do not benefit from overexpression of PDI and BiP[106, 119]. As a eukaryote yeast is particularly suitable for production of heterologous human proteins, since the processing and secretion follows the eukaryotic mechanisms of protein expression. These mechanisms include posttranslational processings, such as folding, glycosylation and phosphorylation[115]. The expression, folding in the ER and secretion of the protein are subject to a strict quality control, which has the effect that correctly folded and functional protein can be isolated from yeast expression cultures.

Surface Display of the Fc Binding Domain

The aim of the present work was to establish and try out a method for non-covalent surface display of Fc fusion proteins and IgG molecules on yeast cells. In contrast to covalent surface display[92] on yeast cells, in the method presented here the protein to be displayed is anchored on the cell surface via its Fc part of the Fc binding ZZ domain. For this purpose the ZZ domain is anchored covalently on the cell surface as the Aga2p fusion protein. By regulation of the expression of the ZZ domain there is the possibility of switching selectively between surface display and soluble secretion. Since the interaction between the ZZ domain and the Fc part is reversible and pH-dependent[67], the system must meet the demand of a stable genotype-phenotype coupling, which is the prerequisite for successful use of the system as a method for selection. The protein A (SpA) from *S. aureus* binds with a high affinity to Fc parts of diverse IgG molecules. SpA consists of five domains (A, B, C, D and E), which can also individually bind Fc parts[63]. The folding of domain B is an example for all SpA domains. It consists of two antiparallel α-helices and a slightly twisted third α-helix. As co-crystallisation experiments have shown, helix 3, however, is not directly involved in the Fc binding[64]. The Fc binding domain used in the present work was the Z domain which is derived from domain B and is known also to bind Fc parts of human antibody molecules with a high affinity[149]. The Z domain was generated by Nilsson and colleagues in 1987 by an artificial amino acid substitution in domain B, glycine to alanine at position 29, and shows an improved stability compared with domain B[67]. In addition, the ZZ domain, which is a duplicated Z sequence, was used in the present work. According to the literature, it is attributed a significantly increased affinity for Fc parts compared with the Z domain[144, 150]. In the present work it was possible to display both the Z and the ZZ domain covalently on yeast cells by fusion with the cell wall protein Aga2p. Correct folding of the two domains was detected in FACS by binding an IgG molecule (cetuximab) and subsequent addition of fluorescence-marked antigen (b-hsEGFR) and SA-PE. As expected, the results showed a higher affinity of the ZZ than of the Z domain for Fc parts, since more intense fluorescence marking of the ZZ-displaying cells was possible under the same conditions. This finding can be explained by an avidity effect, since the ZZ domain is a divalent molecule, whereas the Z domain is monovalent[67]. Two potential binding sites for SpA are present in the Fc part, in each case one per heavy chain. This is also the reason why the stoichiometric binding ratio of SpA to IgG is in the ratio of 1:2[63]. Protein A has a five-domain structure which, however, is functionally divalent[151-153]. The simultaneous binding of the four SpA domains of high affinity for Fc explains the increase in the apparent affinity in the combination of several individual SpA domains[68, 144]. It is assumed that the ZZ domain reaches both binding sites on the Fc part, which would also explain the finding of stronger binding of the ZZ domain to Fc compared with the Z domain[144, 150]. Nevertheless, there are indications that a prerequisite of the simultaneous binding of the two binding sites on the Fc part would be a destruction of the α-helical structure of the domain, as a result of which Fc binding would no longer be possible[70]. It is therefore rather assumed that one Z domain of the divalent construct mediates the binding to Fc, while the Z domain not involved in the binding mediates an avidity effect by a weak interaction with the bound Z domain or the second binding site and leads to a reduced $K_{off}$[71, 144] since by the dissociation of one Z domain binding of the other Z domain is rendered possible. This also explains the fact that the Z and ZZ domain have similar affinity constants for binding Fc[144]. In the present work a stronger fluorescence signal by marking with an IgG molecule was measured for the divalent ZZ domain compared with the monovalent Z domain. This finding is presumably not caused by capture of a larger number of IgG molecules on the cell, since a ZZ domain, like a Z domain also, binds only one IgG molecule. In both cases a ratio of 1:1 consequently exists. For this reason it is presumed that solely the stronger binding of the ZZ domain to Fc led to an increase in the fluorescence intensity. In connection with the subject of the work presented here, it has already been demonstrated that the Z domain can be employed for immobilising antibodies on *E. coli* cells[154, 155] and viruses[156, 157]. ZZ-displaying yeast cells have also already served as an immunoadsorbent for detection of antibodies from serum samples[158]. Furthermore, it has been possible to display the ZZ domain as an α-agglutinin fusion on the surface of yeast cells and to mark them with fluorescence by co-cultivation with cells which secreted Fc-EGFP[159].

Surface Display of VHH-Fc Fusion Proteins

It was also additionally possible to mark the ZZ-displaying cells further with an endogenously secreted VHH-Fc fusion protein for marking by the external addition of an IgG molecule (cetuximab). The capacity of the method for non-covalent surface display of VHH-Fc fusion proteins was thereby demonstrated. For this purpose VHH-Fc and ZZ were co-expressed in a cell. By binding the Fc part to the ZZ domain the solubly secreted VHH-Fc fusion protein was captured on the cell and marking was effected via the addition of antigen. In this case significantly lower fluorescence intensities compared with marking with cetuximab were detected in FACS, which indicates a more inefficient marking of the ZZ domain with endogenously secreted VHH-Fc. This finding also indicates that the ZZ domains displayed on the cell surface were not saturated with VHH-Fc and that ZZ domains which were still free were present. One reason could be a more inefficient secretion of the VHH-Fc protein in contrast to the ZZ domain or an imbalance in the secretion of the two proteins. The expression of the two genes (ZZ and VHH-Fc) was regulated by the Gal1 promoter. A similarly high expression level could therefore be expected for the two genes. However, limiting steps in the expression of foreign genes in *S. cerevisiae* are known.

Reference may be made here by way of example to the fact that using the same promoter genes intrinsic to the yeast are expressed to a greater extent than foreign genes[141]. The reason for this circumstance is the effect of codon usage on translational elongation. In spite of the redundancy of the genetic code, certain codons are preferred during translation, since not all tRNAs and aminoacyl-RNAs are present in the same manner. In addition, codon usage differs markedly between various organisms[141]. In the present work the sequence of the VHH-Fc fusion was not optimised with respect to the codon usage of S. cerevisiae, and accordingly represents a possible problem during translation. Why the VHH-Fc secretion was reduced could thereby be explained. A further reason for the different secretion of the two proteins may be presumed to be posttranslational. Compared with the VHH-Fc fusion protein the ZZ domain is a small protein which is effectively functionally folded and secreted without disulphide bridges. Due to its good secretion and folding properties, the ZZ domain is often produced as a fusion with proteins which show poor secretion[160, 161]. Folding of the VHH-Fc fustian protein, on the other hand, requires the correct formation of at least three disulphide bridges which are located in the hinge region. The importance of correct disulphide bridging for successful soluble secretion of the VHH-Fc fusion protein is explained in the following section. For this purpose, the secretion output of the PDI (protein disulphide isomerase)-overexpressing yeast strain (APO-E) was compared with the strain EBY100, which does not overexpress PDI.

Secretion of VHH-Fc Fusion Proteins

To improve the secretion of VHH-Fc fusion proteins, two yeast strains were produced. By genetic manipulation, the constitutive overexpression of the ER-located oxidoreductase PDI was achieved in these strains (APO-E and APO-B) in comparison with the yeast strains from which they originated (EBY100 and BJ5464). For the strain APO-E a protein concentration which was twice as high compared with the starting strain EBY100 was measured in the supernatant of VHH-Fc expression cultures. This finding substantiates already published results that PDI overexpression has an advantageous effect on soluble secretion of the protein[162]. PDI is known to catalyse the oxidation and reduction of disulphide bridges during folding of proteins in the ER of the yeast cell. This is a decisive step in the secretion path of the cell, since the correct formation of disulphide bridges is critical for the structural stability of proteins, such as e.g. of the VHH-Fc fusion protein used here. The intracellular quality control mechanism ensures that only correctly folded proteins are secreted. Incorrectly folded proteins expose e.g. hydrophobic amino acid regions and thereby lead to induction of the UPR (unfolded protein response). These proteins are then bound by further ER-located chaperones, such as e.g. BiP, which subsequently leads not to secretion but amongst other things to the degradation of the proteins by means of ERAD (ER-associated degradation)[115]. In the present work correct folding of the VHH-Fc proteins was presumably facilitated by the overexpression of PDI, as a result of which it was possible for a larger amount of protein to be secreted, since a higher content of correctly folded protein was present in the intracellular region. However, significantly greater and more efficient increases in secretion by overexpression of PDI have been shown from the literature[111]. Rakestraw and colleagues showed e.g. a 180-fold increase in the secretion of a whole IgG molecule by using a PDI-overexpressing yeast strain and the secretory sequence app8[111]. This secretion efficiency were not achieved in the present work even in combination with the secretory sequence app8. The improved secretion by the overexpression of PDI is presumably dependent upon the particular protein secreted[117] and it would be appropriate to clarify whether the overexpression of other chaperones could lead to a further increase in VHH-Fc secretion. It is furthermore known that PDI acquires de novo disulphide bridges from the likewise ER-located enzyme Ero1p, which it then uses directly for oxidation of disulphide bridges in the substrate protein[163]. Seen in this way Ero1p is responsible for recycling of PDI, in that it converts the PDI from the reduced into the oxidised state. For this reason it would presumably be advantageous to overexpress Ero1p to the same extent as PDI. By a balanced expression level of Ero1p and PDI reduced PDI molecules can be oxidised again more quickly in order to oxidise new disulphide bridges in the substrate protein.

Optimisation of the Surface Display and Secretion of VHH-Fc Fusion Proteins

In addition to the overexpression of PDI further factors also showed an influence on improving soluble secretion of VHH-Fc fusion proteins and surface display thereof. The influence of the expression conditions on surface display and secretion and the influence of the gene dose on secretion is therefore discussed in the following. At the start of the experimental work commercially obtainable synthetic minimal media (Clontech) were used for the cultivation and surface display. These media had a slightly acid pH (pH 5.8) and were in a non-buffered form. During the cultivation of yeast cells in synthetic minimal medium a further acidification was observed, which was presumably caused by metabolism products excreted by the yeast. Analogously to this, a pH of approx. 3 was measured in overnight cultures (data not shown). The use of these media proved to be disadvantageous against the background of the pH-dependent ZZ:Fc interaction, since by lowering the pH the binding of the ZZ domain to the Fc part becomes weaker[164]. Using these media it was not possible to detect surface display of the VHH-Fc since according to the literature the interaction of the Z domain and Fc part no longer exists after pH 3.3[67]. By subsequent use of buffered minimal medium (pH 7.0) the pH was stabilised over a sufficiently long cultivation period and the development of the binding between the ZZ domain and VHH-Fc was rendered possible. In this case it was possible to mark the VHH-Fc fusion protein on the cell via the interaction with the antigen and as a result to detect it in FACS. However, an only slightly increased fluorescence intensity compared with the negative control was measured. Furthermore, the fluorescence intensities were 40 times lower than in the case of marking of ZZ-displaying cells with externally added IgG. As already mentioned, this indicates a less efficient expression of the VHH-Fc fusion or secretion of the VHH-Fc fusion protein. This assumption is supported by the circumstance that the ZZ domain was displayed on the cell surface at the same time with a significantly higher efficiency and many ZZ domains were thus unoccupied, since it was possible for the ZZ domain to be marked to a significantly greater extent on the cell surface with a protein A-specific detection antibody. A significant intensification of the fluorescence signal for the surface display of the VHH-Fc fusion protein was achieved only by the addition of 11% (w/v) PEG8000 to the culture medium. The fluorescence signal for the ZZ domain, however, was of constant intensity with and without PEG addition. It can be concluded from this that PEG8000 had a positive influence on the secretion of the VHH-Fc fusion protein. This assumption was confirmed by further experiments which are discussed in the following. Analysis of the supernatant of VHH-Fc expression cultures with and without PEG8000 showed that the VHH-Fc fusion protein was secreted very much more efficiently by the addition of PEG8000, since significantly higher protein concentrations were detected in the culture medium. Secretion of the VHH-Fc fusion protein into the culture medium requires an intracellular transport of the protein via the cell membrane. The conventional secretory path of proteins in S. cerevisiae leads co- and/or posttranslationally into the endoplasmic reticulum, from there into the Golgi apparatus and starting from this to the cell membrane via transport vesicles[165]. Extracellular secretion then takes place by means of exocytosis through the fusion of the transport vesicle with the cell membrane and the discharge of the vesicle contents into the culture supernatant. It is possible that PEG8000 facilitates the vesicle fusion with the cell membrane and in this way improves secretion of the VHH-Fc fusion protein. It has already been shown that PEG to an increase in membrane permeability and modifies the fluidity properties of membrane components[166]. This can take place from the direct interaction of PEG with the lipid double layer and the resulting destabilisation thereof. For this reason PEG is also routinely used for cell fusion during hybridoma production and is generally called a "fusogen"[167]. However, the influence of PEG can also have an indirect nature, in that it influences the polar properties of the surrounding aqueous medium and as a result leads to a reduction in membrane stability. This effect can be explained by a dehydration of the polar head groups of the lipid double layer by the highly hydrophilic PEG in the surrounding medium[168]. The precise mechanism of the VHH-Fc secretion improved by PEG can only be speculated on here. Interestingly the secretion efficiency depended greatly on the molecular weight of the PEG used. A significantly larger amount of protein was detected In the culture medium with high molecular weight PEG8000 than with PEG1500. The molecular weight of the PEG used presumably correlates directly with the possible interaction of PEG with the cell membrane. Uma Maheswar Rao and Satyanarayana likewise illustrate the influence of the molecular weight of PEG on the secretion. They showed an improved secretion of α-amylase from Geobacillus thermoleovorans in the presence of PEG8000 compared with PEGs of lower molecular weights[140]. The more intense fluorescence signal for surface-displayed VHH-Fc fusion proteins in the presence of PEG8000 can additionally also be explained further by a reduced dissociation of the Fc part of the ZZ domain due to the increased viscosity of the medium, in addition to the increased secretion already described and the higher occupation rate of the ZZ domains on the cell surface thereby caused. In this case the diffusion of dissociated VHH-Fc fusion proteins is reduced due to the high viscosity of the medium and the association of ZZ and Fc is facilitated. The cell densities achieved during cultivation in medium containing PEG8000 indicate that PEG did not have a significant influence on the growth properties of the culture, although a reduced entry of oxygen due to the high viscosity of the medium was calculated. Nevertheless, comparably high cell densities during cultivation were achieved with and without PEG (data not shown). The VHH-Fc gene dose within the yeast cell depends inter alia on the number of copies of the plasmid. An increased synthesis rate of the VHH-Fc fusion protein due to an increase in the number of plasmid copies was expected. Since in the results discussed so far CEN6/ARS4-based plasmids which are distinguished by a low number of copies in the cell were used, it was presumed that the use of a 2 micron-based plasmid could lead to an increased secretion of the VHH-Fc fusion protein. These plasmids are distinguished by a number of copies in the cell which is up to 100 times higher[139]. For this purpose VHH-Fc expression cultures for soluble secretion which differ with respect to their number of plasmid copies were prepared. Interestingly, against all expectations a lower protein secretion of the 2 micron-based plasmid was measured and the expression of the VHH-Fc gene sequence of the CEN6/ARS4-based plasmid resulted in a more efficient secretion of the protein into the culture supernatant. Furthermore, it was to be observed that by using the 2 micron plasmid an increased intracellular concentration of the non-processed VHH-Fc fusion protein was present compared with the CEN6/ARS4 plasmid. Since the pre-pro signal peptide app8 used has a molecular weight of 8.7 kD, a distinction was to be made between the intracellular forms (processed and non-processed) of the VHH-Fc fusion protein in western blot analyses. The mature VHH-Fc fusion protein was readily distinguishable from the non-processed form by its lower molecular weight after removal of the signal peptide, and both protein forms were to be detected immunologically in the cell lysate. The non-processed protein form was detected only when the 2 micron plasmid was used. This finding indicates a less efficient removal of the signal peptide by the intracellular proteases. It is possible that an increased transcript level and the resulting larger amounts of protein limited correct processing of the protein. Two intracellular proteases are responsible for the removal of the pre-pro signal peptide. The first 19 amino acids of the pre-region are cleaved by an ER-located signal peptidase. After passage of the protein in the ER and transport thereof to the Golgi apparatus, the protease Kex2p is responsible in late Golgi compartments for removal of the pro-region[141]. The pro-region comprises a further 64 amino acids. It can be presumed that the protease Kex2p was the limiting step in the processing of the protein, since it removes the significantly larger pro-region of the signal peptide. It can be said generally that the overexpression and secretion of heterologous proteins always represents a stress situation for the yeast cell[117]. The high number of copies presumably led to an increased transcript level and thus to a stress response by the yeast cell. Secretion could thereby be impeded, since by the accumulation of intermediates and incorrectly folded proteins the UPR mechanism could be induced as a consequence of stress. This would lead to proteolytic degradation of the protein instead of secretion. There is furthermore the possibility of limitation of energy and resources for protein syntheses which are to be observed at high transcript levels above all in E. coli[169, 170]. Furthermore, however, the translocation of the protein, as mentioned, the processing of the signal peptide and the folding of the protein in the ER can also have a limiting effect on secretion. Although it has not been possible to clarify completely the finding of reduced secretion by an increase in the gene dose, the CEN6/ARS4-based plasmid was used for further secretion.

Functionality of VHH-Fc Fusion Proteins Produced by Yeast

The functionality of the VHH-Fc fusion protein was investigated both on the cell during the surface display and solubly in the culture supernatant. For successful use of the non-covalent method for selection and for characterisation of VHH-Fc fusion proteins it was necessary for the protein to be in a functional form both on the cell and in the culture supernatant. The functionality is in general determined by correct glycosylation and folding of the protein. The functionality of the surface-displayed protein was detected via the binding of the specific antigen. Over a period of 72 hours it was possible for the VHH-Fc fusion protein on the cell to be marked by binding to the antigen hsEGFR and to be successfully detected in FACS. Compared with the SpA domains A to E, Z and ZZ domains bind IgG molecules only via the Fc part[64]. For domains A to E, on the other hand, IgG molecules have a further possible binding site located in the Fab fragment. This binding takes place mostly via hydrophilic amino acid residues of the Fab fragment. It was likewise shown that protein A binds framework regions of VHH domains[171]. By the interaction of SpA or domains thereof with the Fab fragment of an antibody or the VHH domain, a binding competing with the antigen could occur, as a result of which the antigen binding could be impaired. Using the ZZ domain for surface display ensures that the binding of VHH-Fc fusion proteins and IgG molecules takes place exclusively via the Fc part and binding to the antigen is thus not impeded. By binding of the Fc part a favourable alignment and exposure of the surface-displayed proteins is moreover possible. The yeast cell has a cell wall approx. 200 nm thick outside the plasma membrane, which is densely populated with cell wall proteins intrinsic to the yeast[172]. By using the Aga1p-Aga2p protein complex for surface anchoring of the ZZ domain this is exposed sufficiently far into the extracellular environment in order to render binding to e.g. VHH-Fc fusion proteins possible. Furthermore, by the binding of the Fc part, as mentioned, the two VHH domains of the homodimeric VHH-Fc fusion protein are displayed at a further distance from the cell and are exposed such that unimpeded interaction with the antigen is possible. It is known that short anchor proteins, such as e.g. shortened forms of the protein Flo1p, do not reach sufficiently into the extracellular environment of the cell and for this reason surface-displayed proteins cannot be detected in the desired manner since interaction with the antigen or with detection antibodies is sterically hindered by the cell wall[94]. On the other hand, using a lengthened Flo1p form renders detection possible. In view of the further investigation of the functionality of the VHH-Fc fusion protein within the non-covalent system, expression cultures for soluble secretion of the VHH-Fc fusion protein into the culture supernatant were prepared. The functionality was evaluated via determination of the kinetic constants of the biomolecular interaction of the protein and the antigen hsEGFR. For this purpose the protein from the culture supernatant was purified by means of protein A affinity chromatography and used for the binding analysis by means of biolayer interferometry. The kinetic constants of the binding to hsEGFR were known from measurements performed beforehand with the VHH-Fc fusion protein from an HEK293 expression culture (data not shown). Comparable measurement values which lay in a $K_D$ range of from 9 nM to 90 nM were achieved both for the protein produced by the yeast and for that produced by HEK293. Since in contrast to yeast expression an N-terminal Fc fustian of the VHH domain (C terminus of the Fc part on the N terminus of the VHH domain) was used for the HEK293 expression, the different $K_D$ values can be explained by the nature of the Fc fusion. The antigen binding of the VHH domain takes place via the N-terminal regions of the domain. The three CDRs which form the paratope, and in this way mediate binding to the antigen, are located there[173]. In the gene sequence used for the HEK293 expression the 5' region of the VHH gene was fused with the sequence for the Fc part. It is possible that a reduction in the affinity for the antigen was thereby caused, which manifested itself by a lower $K_D$ value in the biolayer interferometry measurement. It was presumed that the C-terminal fusion of the VHH domain with the Fc part (N terminus of the Fc part on the C terminus of the VHH domain) did not lead to an impairment of the binding of the antigen, since a higher $K_D$ value was measured for the antigen binding compared with the N-terminal Fc fusion. This finding is plausible since in naturally occurring heavy chain antibodies the VHH domain is also bound to the Fc part via its C terminus via the hinge region. Since the antigen binding, as mentioned, is mediated via the N terminus of the VHH domain and the CDRs located there, these are not impaired and are freely accessible for the interaction with the antigen by Fc fusion. Reference may be made here by way of example to the VHH-Fc fusion ART621 (Arana Therapeutic Ltd.) which is currently undergoing clinical trials for treatment of psoriasis[174]. It was furthermore possible to establish in western blot analyses that the dimerisation of the VHH-Fc fusion protein was successful. Dimerisation is rendered possible by correct folding of the heavy chains of the Fc part and the formation of disulphide bridges. This was presumably facilitated by the mutagenesis of the N-glycosylation site of the Fc part at the start of the present work. For this purpose the codon for the amino acid asparagine (N) at position 297 was substituted for the codon for the amino acid glutamine (Q) and in this way the hypermannosylation[175] known for S. cerevisiae during the N-glycosylation of proteins was prevented. The high number of mannose residues could otherwise sterically hinder the Fc dimerisation, as a result of which hydrophobic contact areas between the chains in the ER could become exposed. This would induce a stress response by the cell and result in an impairment of secretion of the protein. It was furthermore possible to demonstrate the functionality of the Fc part during the biolayer interferometry, since it was possible for protein A sensors to be successfully loaded with the VHH-Fc fusion protein. Under natural conditions human IgG molecules are glycosylated at position 297. It was observed that human glycosylation of this position contributes towards stabilising of the CH2 domain and therefore has a positive effect on dimerisation of the Fc part of IgG molecules[176].

Surface Display of IgG Molecules

The diverse use of the method established in this work was also demonstrated by the successful surface display of whole IgG molecules. This makes clear that it was possible for various antibody formats to be displayed successfully. Nevertheless, non-covalent surface display of IgG molecules was more complex in configuration compared with VHH-Fc fusion proteins since in contrast to surface display of VHH-Fc fusion proteins the yeast cells were transformed with three instead of with only two plasmids. In addition to the plasmid for expression of the Aga2p-ZZ fusion, two further plasmids were required for soluble secretion of the light and heavy antibody chain. For surface display of the whole antibody, the yeast cell consequently had to render possible the stable obtaining of all three plasmids during the cultivation. For this purpose selection of the Aga1p-ZZ plasmid (pYD-ZZ) took place via a G418 resistance marker and G418-containing medium in order to use the auxotrophic marker of the EBY100 strain for selection of the plasmids for the heavy and light antibody chain. Successful capture of the antibody by the ZZ domain was demonstrated by marking and detection of the Fc part on the cell. It was possible to detect the functionality of the IgG molecule via binding of the specific antigen. Nevertheless, it was not possible to detect reliably whether the light chain was also displayed in addition to the heavy chain, since at this point in time no suitable specific detection antibody for the light chain was available. It is possible that the heavy antibody chains also mediate binding to the antigen without assembling of the light chains, since the majority of the binding takes place by the heavy chains of the IgG molecule[177].

Nevertheless it is to be assumed that the assembling of the light and heavy IgG chain was successful, since otherwise the surface display would presumably be reduced by a poorer secretion of the antibody. Since the assembling of the light and heavy chain takes place via hydrophobic interaction, in addition to the disulphide bridge between CH1 and CL, the hydrophobic amino acid residues of the heavy chain would be exposed in the ER and would induce the mechanism of UPR. Interestingly it was possible to demonstrate surface display of a whole IgG molecule on yeast cells only using the non-covalent method with the ZZ domain. This finding emerged by a further experiment in which the heavy IgG chain was displayed covalently on the surface as Aga2p fusion, whereas the light chain was secreted solubly. In this experiment it was possible to detect the heavy chain on the cell surface via marking of the Fc part. Moreover, however, detection of the antigen binding was unsuccessful. For soluble secretion of the light chain the secretory sequence app8 selected by Rakestraw and colleagues[111] was used, while the heavy chain was expressed as fusion with AGA2. The choice of the signal peptide is known to have a great influence on the secretion of heterologous proteins from *S. cerevisiae* since the signal peptide determines whether a protein is secreted, has an intended site in the cell or becomes a constituent of the cell membrane. Hashimoto and colleagues were able to show that using different signal peptides results in a significant difference in the secretion yield[178]. The signal peptide app8 used for secretion of the light chain had been selected specifically for efficient secretion of proteins by an evolutive approach based on the MFα1pp signal peptide. This signal peptide is an 83 amino acid pre-pro sequence which, in contrast to other signal peptides, is processed both by a signal peptide for translocation into the ER and by the membrane-located protease Kex2p in the Golgi apparatus. The heavy chain, on the other hand, was secreted as a fusion with the protein Aga2p, which is bound to the cell wall protein Aga1p via two disulphide bridges. Processing of the mature fusion protein is presumably effected here only via the ER-located signal peptidase. The different processing mechanisms of the light and heavy chain could have made the assembling of the two chains difficult such that it was not possible to detect antigen binding. In the case of the non-covalent surface display discussed above for the antibody, both the heavy and the light chain were expressed with the secretory sequence app8. In this case both antibody chains were subject to the same processing mechanism, which presumably rendered possible a functional assembling and the binding to the antigen. Rakestraw and colleagues showed in 2009 the surface display of a whole antibody on yeast cells using the SECANT™ display technoloy[126]. For surface display, the heavy chain was expressed as a fusion with the biotin acceptor peptide for this. The biotinylation of the biotin acceptor peptide was carried out by the co-expressed biotin ligase BirA. After chemical biotinylation of the cell surface and incubation with avidin, presentation of the biotinylated antibody secreted takes place via the avidin-biotin interaction on the cell. In this set-up both antibody chains were expressed with the same secretory sequence (app8). They showed the secretion of a whole IgG molecule from *S. cerevisiae* and the non-covalent surface display of the IgG molecule via the biotin-avidin interaction. A further example for the surface display of whole IgG molecules on yeast cells was shown by Sazinsky and colleagues in 2008. They displayed a fluorescein-specific IgG molecule via binding to chemically conjugated fluroescein on the cell surface[179]. This type of surface display, however, in contrast to non-covalent surface display via the ZZ domain, has the disadvantage that IgG molecules are captured on the surface via the binding to their antigen. Consequently only proteins of known and sufficient affinity can be displayed. Furthermore, an individually conjugated cell surface must be generated for each selection. In contrast to the two systems of surface display mentioned, in the present work IgG molecules are displayed without further modifications, rather structures of the IgG molecule intrinsic to the protein are used for surface display in the method. It is thereby guaranteed that the antigen binding Fab fragments of the antibody are freely exposed. In addition the non-covalent method renders possible the direct use of the selected clone for soluble secretion without further subclonings. Nevertheless, the binding used for the surface display (ZZ:Fc interaction) is less stable than the binding between avidin and biotin.

Genotype-Phenotype Coupling

Successful use of non-covalent surface display for selection of variants with modified properties can only be achieved if a stable link exists between the displayed protein variant on the cell and the intracellular genetic information for this variant. If this link does not exist identification of variants during the selection is not possible. Compared with covalent surface display on yeast cells[92] this aspect requires particular consideration in the system presented here since the surface display is pH-dependent and reversible. It has been shown that acidification of the culture medium leads to a poorer binding between the ZZ domain and Fc part and that this binding is no longer formed below pH 3.3. There is furthermore the possibility that protein variants are bound to an "incorrect" cell by dissociation and association of the binding of the ZZ domain and Fc part and the selection of falsely positive clones may occur in this way. Investigation of the stability of the ZZ:Fc interaction was therefore a central constituent of the present work. This interaction was investigated experimentally in two different mixing experiments. In the first mixing experiment cells which displayed the ZZ domain (target cells) were concentrated via binding of IgG molecules from a high excess of control cells. For this the target cells are diluted in a large population of control cells and concentrated from initially 0.001% or 0.0001% to 100% or, respectively, 90% within three selection rounds. The target cells were marked by sequential binding of cetuximab and the fluorescence-marked antigen (b-hsEGFR). The high rate of concentration of 100% or 90% shows the stable interaction between the ZZ domain and IgG molecule. The successful use of the usual selection methods, such as MACS and FACS, was furthermore demonstrated. The high expression rate of the ZZ domain without doubt had a positive influence on the marking and selection of the target cells. Since the expression of the ZZ domain was regulated by the potent Gal1 promoter, after induction in galactose-containing medium a large number of ZZ domains were displayed on the cell surface. A high concentration of cetuximab and hsEGFR was furthermore used for marking the cells in order to render possible a complete saturation of the ZZ domains on the target cells. As a result it was possible for the target cells to be intensely fluorescence-marked and in FACS to be clearly distinguished from the control cells, which showed a significantly lower rel. fluorescence intensity. Even by dissociation of IgG molecules from the cell surface and distribution of these within the cell mixture, it was not possible for control cells to be marked with available free IgG molecules since these displayed no ZZ domains. In this case only a weak non-specific interaction with the cell surface was to be expected, which did not lead to selection of falsely positive control cells. In the second mixing experiment both target and control cells displayed the ZZ domain. The target cells additionally secreted the hsEGFR-specific VHH-Fc fusion protein, whereas the control cells additionally secreted a non-EGFR-specific VHH-Fc fusion protein. The two VHH-Fc fusion proteins should be displayed only on the particular cell population. The target cells were marked via binding of the VHH-Fc fusion protein displayed to the fluorescence-marked antigen (b-hsEGFR) and SA-PE. Determination of the rate of surface display of the two VHH-Fc fusion proteins was rendered possible by the marking of the particular Fc part and allowed a control of the expression of the VHH-Fc fusion proteins. This avoided expression differences leading to a falsification of the selection conditions. Initial dilutions of 0.001% and 0.0001% were prepared. It was possible to concentrate the target cells within the mixtures to 40% and 80% respectively by three successive selection rounds. In this mixing experiment, in contrast to the first mixing experiment, lower concentration rates of the target cells were achieved. In addition, a greater concentration of the target cells was achieved from the initially higher dilution (0.0001%) than from the initially lower dilution (0.001%). This finding is nonsensical and can presumably be explained by errors during the preparation of the mixtures or during the sorting, since at the higher dilution there was a significantly greater demand on the sorting since fewer target cells were initially present. This mixing experiment showed that the majority of the VHH-Fc proteins secreted were captured on their own cell and did not arrive at an adjacent cell by dissociation and diffusion and become bound there. Since, however, a certain content of the VHH-Fc fusion protein nevertheless dissociated from its own ZZ domain due to the kinetic properties of the ZZ:Fc interaction, diffusion of the dissociated VHH-Fc fusion proteins was minimised by a static culture and the increased viscosity due to the addition of 11% (w/v) PEG8000 to the medium. Since the VHH-Fc fusion proteins of the target and control cells had an identical sequence of the Fc part, it was presumed that the VHH-Fc fusion proteins on the control cells dissociated from the ZZ domain in the same manner as the VHH-Fc fusion proteins of the target cells. There is the possibility that a certain portion of the hsEGFR-specific VHH-Fc fusion proteins (target cells) are captured by unoccupied ZZ domains on neighbouring cells. These can be located both on target and on control cells. The content of incorrectly captured VHH-Fc fusion proteins is probably very low, however, because of the high-affinity binding between the ZZ domain and Fc part. Moreover, incorrectly captured VHH-Fc fusion proteins would be distributed within the entire mixture and become highly diluted. By the fluorescence marking with the antigen these signals would then lie below the detection limit in FACS and fall in the region of the fluorescence intensity of the negative control. As a result a selection of falsely positive cells can be ruled out. To increase the complexity of the mixing experiments, target and control cells were first mixed and the surface display of the entire cell mixture was then induced. For this reason it can be presumed that during cultivation for induction of the surface display stable binding existed between the ZZ domain and VHH-Fc fusion protein This procedure represents in detail the procedure for screening molecule libraries. The method of non-covalent surface display on yeast cells consequently appears to be particularly suitable as a selection method.

Switchable Surface Display

A substantial advantage of the non-covalent method compared with the covalent system for surface display on yeast cells is that the non-covalent method opens up the possibility of switching selectively between the modes of surface display and soluble secretion. This switchable function was achieved by using different promoters for expression of the ZZ domain and of the VHH-Fc fusion. For this purpose the expression of the ZZ domain was regulated by the galactose-inducible and glucose-repressible Gal1 promoter, whereas expression of the VHH-Fc fusion took place constitutively by means of the GAPDH promoter. For surface display of the VHH-Fc fusion protein double transformants were cultivated in galactose-containing SG medium. In this case the ZZ domain was displayed on the cell surface as an Aga2p fusion via interaction with Aga1p and it was possible for the VHH-Fc fusion protein to be captured on the cell. This was detected successfully in FACS by marking and detection of the ZZ domain with a specific detection antibody and by the antigen binding of the VHH domain. For soluble secretion of the VHH-Fc fusion protein into the culture supernatant the cells were transferred into glucose-containing SD medium. Repression of the Gal1 promoter and thereby repression of the expression of the ZZ domain took place due to the glucose-containing medium[141]. As a result it was no longer possible for the VHH-Fc fusion protein to be captured on the cell surface and it was secreted into the culture medium. Nevertheless, it was observed that the remaining ZZ domains which were already displayed on the cell before the change of medium were also still displayed after the transfer into SD medium (data not shown). For this purpose the cells were subjected to another passage and a new culture was inoculated with a very low cell density. The cells which still displayed the ZZ domains were greatly diluted by the passage. The cells of the following generations no longer showed surface display due to the repressed expression of the ZZ domain. Using the SECANT™ display technology established by Rakestraw and colleagues it is already possible to switch selectively between surface display and soluble production. In contrast to surface display via the ZZ domain, this method is not limited to the presence of an Fc part of the protein to be displayed. Rather, the surface display is rendered possible via the in vivo biotinylation of the protein and the chemical conjugation of the cell surface with biotin and avidin. For soluble production the chemical conjugation of the cell is merely omitted. However, this system requires the modification of the protein, which is not necessary in the case of surface display with the ZZ domain. Against the background of surface display of IgG molecules, surface display of the antibody in the final format is accordingly possible with the non-covalent method presented in this work. As a result structurally related impairments of the antibody properties by artificial modifications of the protein can be ruled out.

The domain structure of protein A (SpA) is shown as (A). This is built up from five IgG binding domains (E, D, A, B, E), a signal sequence (SP) and two domains (X and M) for anchoring SpA in the bacterial cell wall. (B) shows the artificial Z domain derived from domain B and obtained by recombinant DNA technology. The ZZ domain is produced by duplication of the Z sequence. (Modified according to Boström, T., Nilvebrant, J., Honer, S. 2012[61])

Figure 1:
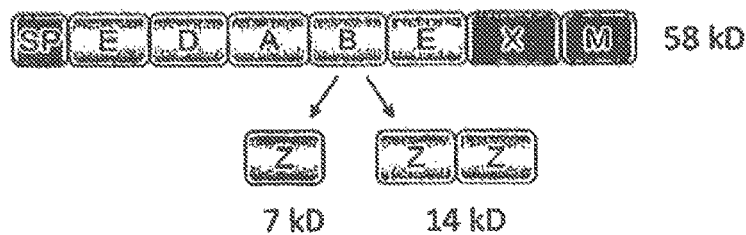
FIG. 1: Diagram of S. aureus SpA and SpA-derived domains.
Figure 2:
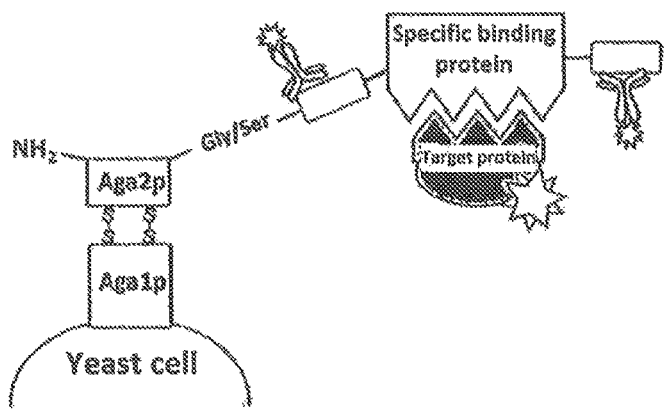

FIG. 2: Surface display on yeast cells according to Boder and Wittrup.

Figure 3A:
Figure 3B:
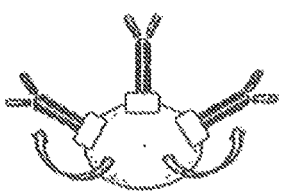
Figure 3C:
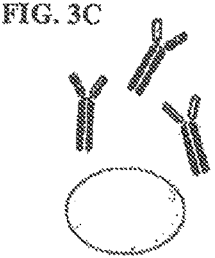

FIG. 3A, FIG. 3B and FIG. 3C: Are diagrams of the method for non-covalent surface display on yeast cells and soluble production.

FIG. 3A: In this diagram, the Fc binding domain anchored covalently on the cell is shown in green. FIG. 3B: In this diagram, the solubly secreted VHH-Fc fusion protein is captured on the cell surface by the Fc binding domain. FIG. 3C: In this diagram, by repression of the expression of the Fc binding domain, the VHH-Fc fusion protein is secreted solubly into the culture medium and no longer captured on the cell surface.

Figure 4:
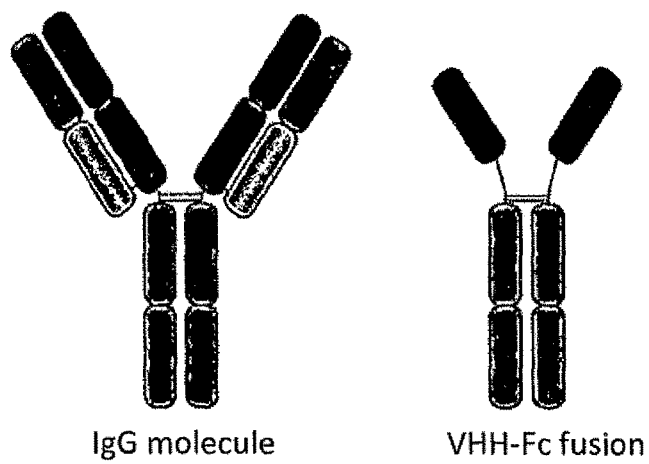

FIG. 4: Diagram of the comparison between the IgG molecule and VHH-Fc fusion protein.

Diagram of the structure comparison between a whole IgG molecule (left) and VHH-Fc fusion protein (right). Both proteins are homodimers, an IgG molecule being built up from two identical light and two identical heavy antibody chains, whereas the VHH-Fc fusion protein is built up only from two identical chains.

Figure 5:
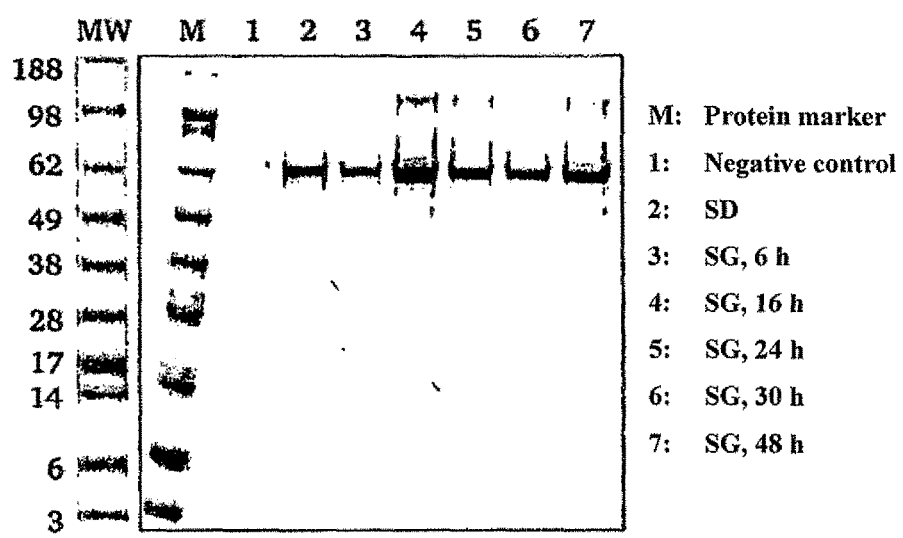

FIG. 5: Western blot analysis of the episomal PDI expression in yeast cells.

Western blot analysis of $2 \times 10^7$ EBY100 URA$^-$ cells (pESC-URA-pGAPDH-PDI transformants). Detection was carried out via a PDI-specific primary antibody from the mouse and a mouse-specific secondary antibody from the goat (POD conjugate). Lane 1 shows the intracellular PDI content in EBY100 URA$^-$ (negative control). Lanes 2 to 7 show the intracellular PDI content by additional overexpression of the episomally coded PDI sequence regulated b the GAPDH promoter at various points in time (see legend).

Figure 6:
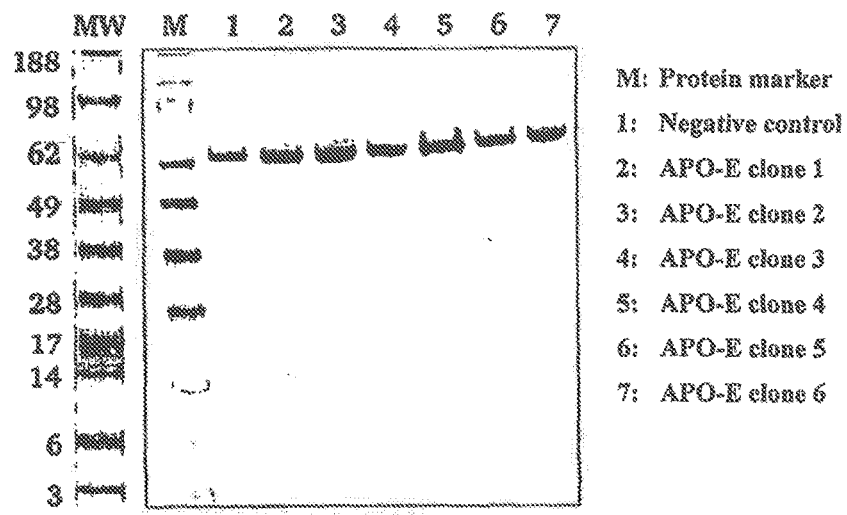

FIG. 6: Western blot analysis of the chromosomal PDI expression in yeast cells.

Western blot analysis under reducing conditions of cell lysates ($2 \times 10^7$ cells) of EBY100 (lane 1) and APO-E (lane 2-4) cultures which were cultivated in galactose-containing SD medium for four days. Detection was carried out via a PDI-specific primary antibody from the mouse and a mouse-specific secondary antibody from the goat (POD conjugate).

Figure 7:
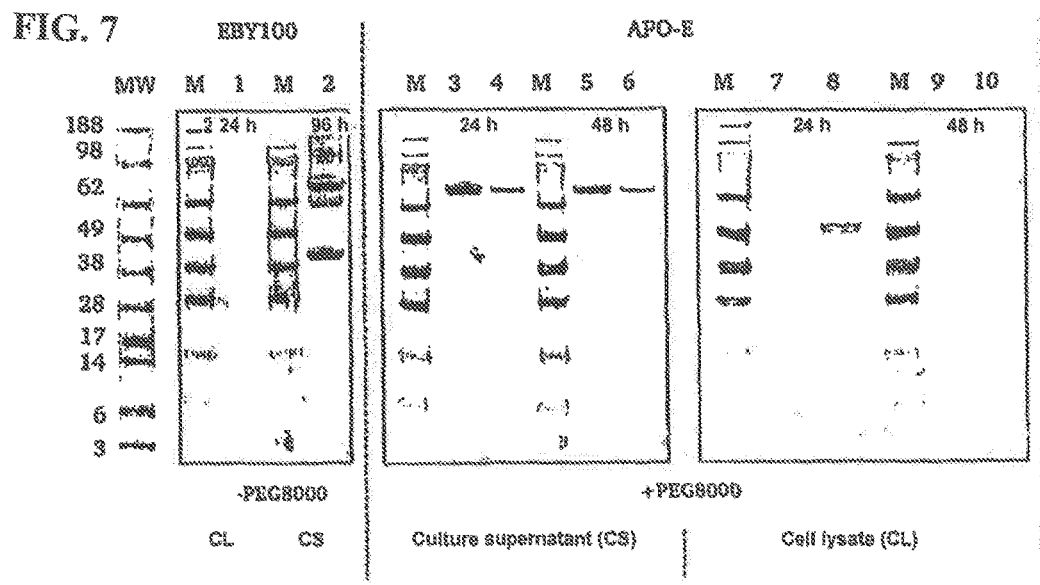

FIG. 7: Analysis of the soluble VHH-Fc secretion.

Western blot analysis of culture supernatants and cell lysates from EBY100 and APO-E cultures with different expression conditions. (A) is an analysis of cell lysate ($1 \times 10^7$ cells, lane 1) and culture supernatant ($5 \times 10^7$ cells, lane 2) of a VHH-Fc (CEN6/ARS4) expression after 96 hours without addition of PEG8000. (B) is an analysis of culture supernatants of VHH-Fc expressions with addition of PEG8000 after 24 hours and 48 hours. The expression plasmid used was an ARS4/CEN6 plasmid (lane 3) and a 2 micron plasmid (lane 4 and 6). (C) shows the cell lysates correlating with (B). Detection was carried out via an Fc-specific primary antibody (rabbit) and a POD-conjugated rabbit-specific secondary antibody (goat). CL: cell lysate, CS: culture supernatant.

Figure 8:
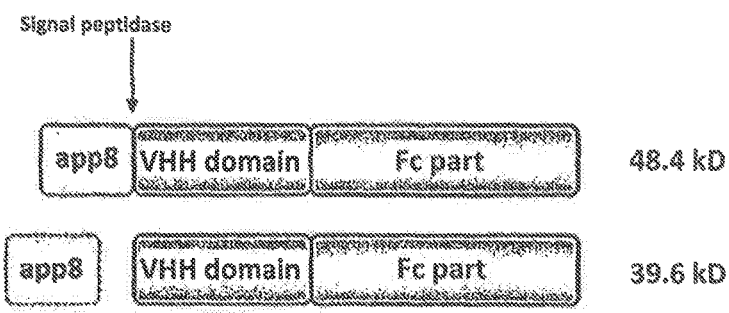

FIG. 8: Processing of the VHH-Fc fusion protein.

Diagram of the intracellular states of the VHH-Fc fusion protein. The non-processed protein (A) is present intracellularly as the larger form (48.4 kD), since the signal peptide app8 (8.7 kD) was not split off, whereas the mature protein (B) had a molecular weight of 39.6 kD. The arrow marks the recognition site of the intracellular signal peptidase.

Figure 9:
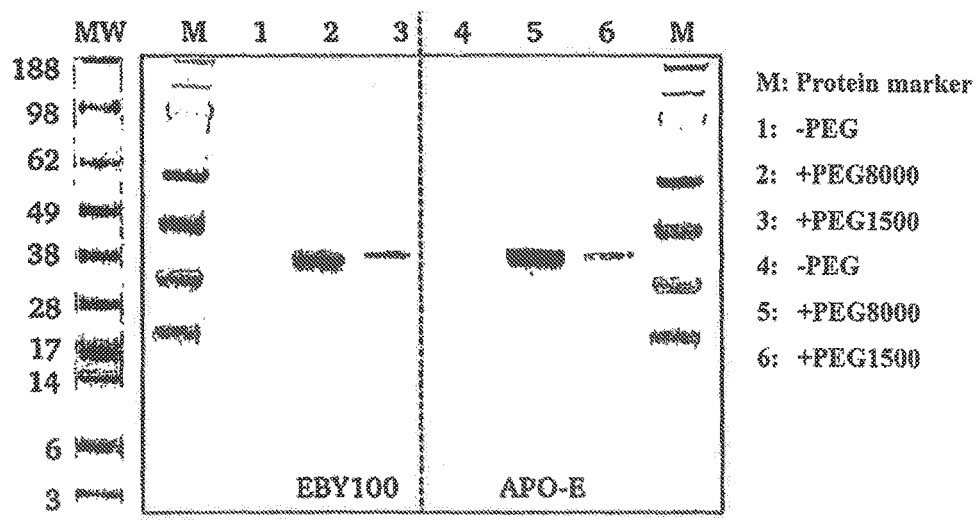

FIG. 9: Influence of polyethylene glycol on the secretion of VHH-Fc fusion proteins.

VHH-Fc secretion after 48 hours. Western blot analysis of EBY100 and APO-E culture supernatants for analysis of the influence of polyethylene glycol (PEG) on the amounts of protein detectable in the culture supernatant. Expression media of different composition. Lane 1 and 4: no PEG addition, lane 2 and 5: 11% (w/v) PEG8000, lane 3 and 6: 11% (w/v) PEG1500.

Figure 10:
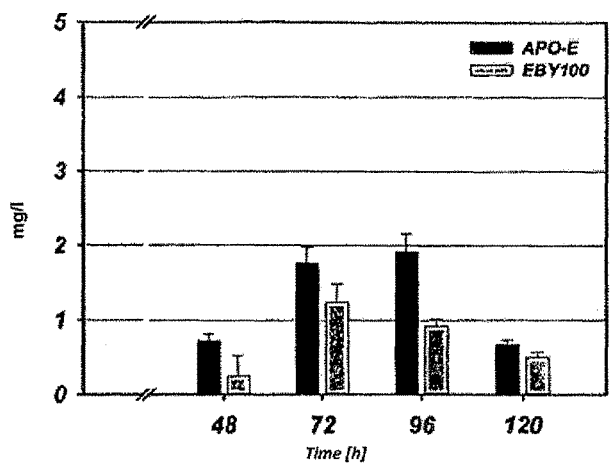

FIG. 10: VHH-Fc secretion yields from APO-E and EBY100 expression cultures.

Biolayer interferometry measurement for determination of the concentration of the VHH-Fc fusion protein in the supernatant of EBY100 and APO-E expression cultures over a period of 120 hours. Error bars represent three independent measurements.

Figure 11A:
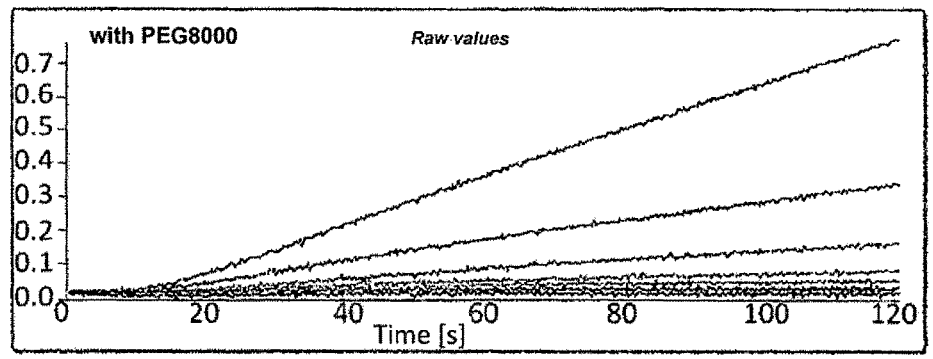
Figure 11B:
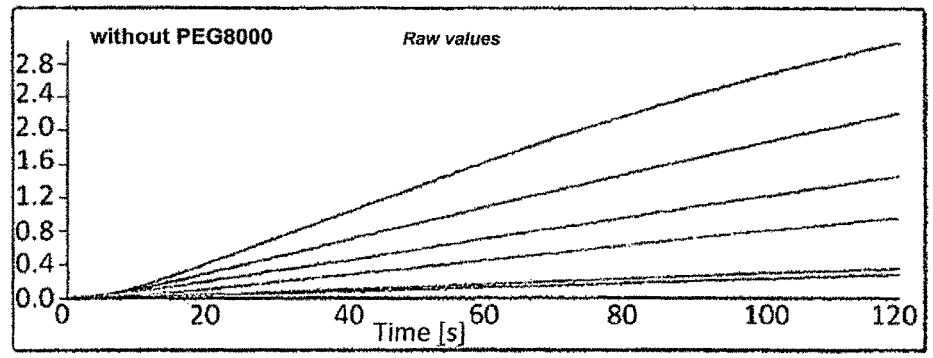

FIG. 11A and FIG. 11B: Examples of biolayer interferometry measurement profiles with and without addition of PEG.

Examples of biolayer interferometry measurement profiles of the loading of protein A biosensors with IgG molecules using soluble protein in SD medium+11% (w/v) PEG8000 are shown in FIG. 11A and in PBS (without PEG8000) are shown in FIG. 11B. The coloured curves represent various IgG concentrations used for loading the protein A biosensors. In the descending sequence 25, 10, 5, 2, 1, 0.5, 0.1, 0 mg/l.

FIG. 12: VHH-Fc secretion yields from APO-E and APO-B expression cultures.

Biolayer interferometry determination of the concentration of the VHH-Fc fusion protein in the supernatant of APO-E and APO-B expression cultures over a period of 120 hours by means of protein A biosensors. The error bars represent three independent clones.

FIG. 13A and FIG. 13B: LDS-PAGE and western blot analysis of culture supernatants from APO-E and APO-B VHH-Fc expression cultures.

FIG. 13A is LDS-PAGE under reducing conditions of VHH-Fc fusion proteins (culture supernatants) from three independent expression cultures, Coomassie-stained. 2 μg of the antibody cetuximab were used as a control (+). FIG. 13B is a Western blot analysis of the samples from (A). Detection via an Fc-specific primary antibody (rabbit) and a rabbit-specific POD-conjugated secondary antibody (goat). 1 μg of cetuximab was used as a control (+).

FIG. 14A, FIG. 14B and FIG. 14C: Purification of VHH-Fc fusion proteins by means of protein A affinity chromatography.

FIG. 14A is a chromatogram of the affinity chromatography purification by means of a protein A HiTrap column of VHH-Fc from APO-E (red) and APO-B (black) 200 ml expression cultures after dialysis against PBS. The 1 ml fractions of the elution peak from (A) were combined and rebuffered in PBS by means of PD-10 columns. Continuous lines represent the absorption (mAu), broken lines represent the conductivity (mS/cm). FIG. 14B and FIG. 14C show the elution fractions of the PD-10 column (500 μl each) which were analysed by means of LDS-PAGE (non-reduced).

FIG. 15: Analytical procedure for the purification of the VHH-Fc fusion protein.

Western blot analysis (reduced) of expression and purification of the VHH-Fc protein from the supernatant of a 200 ml APO-E culture. HEK293-produced VHH-Fc fusion protein was used as a positive control. Samples of the fusion proteins were analysed at various points in time of the purification process (see legend).

Figure 16A:
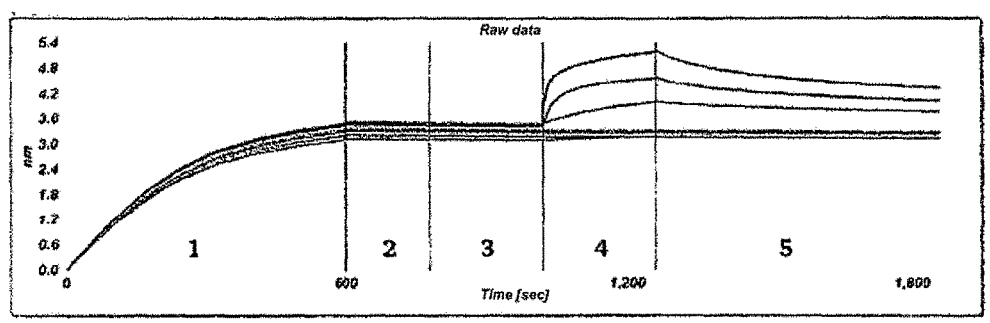
Figure 16B:
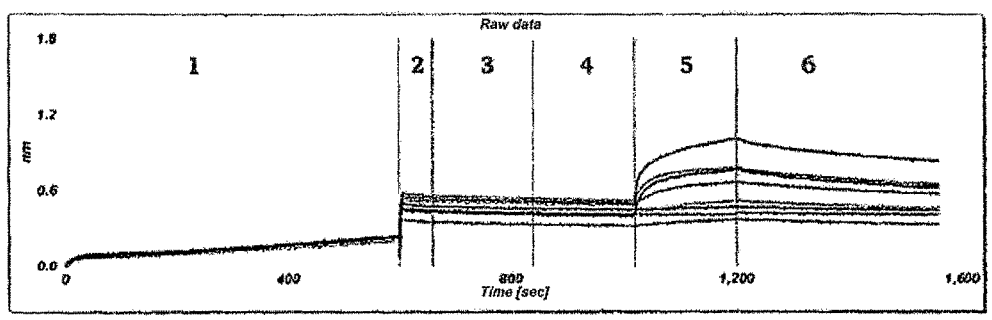

FIGS. 16A and 16B: Analysis of the interaction of VHH-Fc and hsEGFR—biolayer interferometry measurement profile (raw data).

Raw data of the biolayer interferometry measurement profile of purified VHH-Fc fusion protein (FIG. 16A) and VHH-Fc from the supernatant (FIG. 16B) on hsEGFR. The measurement profiles of eight protein A biosensors are shown. (1) Loading of the protein A biosensors with VHH-Fc for 600 s. (A 2 to 3): washing step, (B 2 to 4): washing step, (A 4 to B 5) association, (A 5, B 6): dissociation.

Figure 17A:
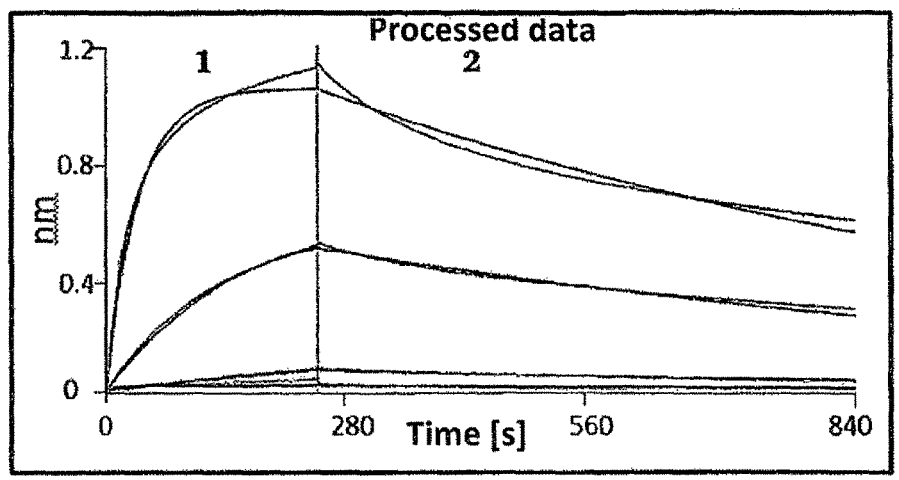
Figure 17B:
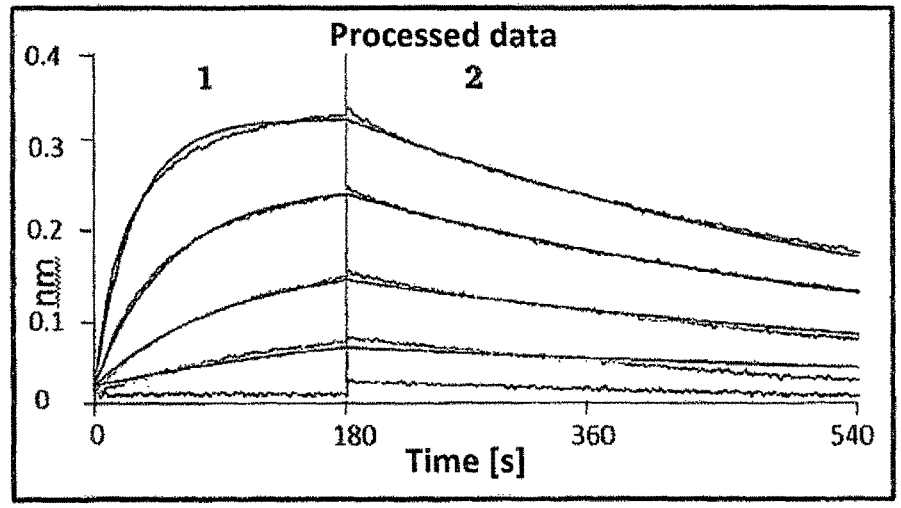

FIG. 17A and FIG. 17B: Binding analysis of VHH-Fc and hsEGFR (processed data).

Kinetic characterisation of the biomolecular interaction of VHH-Fc and hsEGFR. The processed sensorgrams are shown. Association (1) and dissociation (2) of hsEGFR on the VHH-Fc fusion protein immobilised on the sensor surface. Purified VHH-Fc protein in PBS (FIG. 17A) and VHH-Fc in the culture supernatant (FIG. 17B). Negative controls: (FIG. 17A) mmEGFR, (FIG. 17B) hs-cMet. Protein concentrations are plotted individually. Coloured curves show the experimentally determined data, red curves show the statistical fitting of these data.

Figure 18:
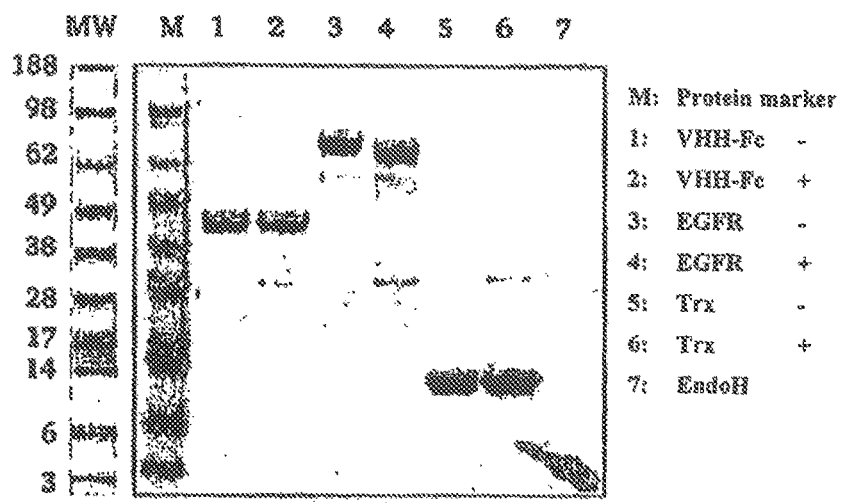

FIG. 18: VHH-Fc glycosylation analysis.

LDS-PAGE of the yeast-secreted VHH-Fc protein with (+) and without (−) EndoH. In each case 2 µg of the following proteins were treated with EndoH under the same conditions as controls: hsEGFR (from CHO) and thioredoxin (from *E. coli*).

Figure 19:
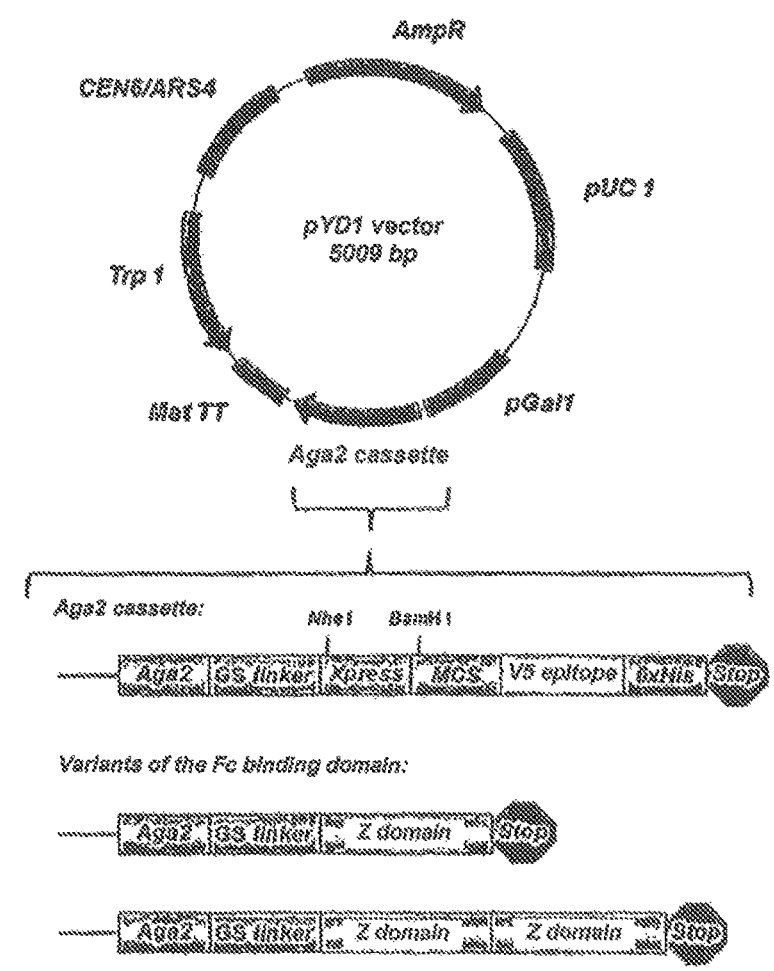

FIG. 19: Cloning plan for surface display of the Fc binding domains.

Diagram of vector pYD1 for the surface display of the Fc binding domain (Z and ZZ domain) as the Aga2p fusion protein. (A) shows the individual components of the Aga2p cassette. Cloning of the Z domain was carried out via the restriction cleavage sites NheI and BamHI shown in (A). (B) shows the construct Aga2p-Z domain. (C) shows the construct Aga2p-ZZ domain.

Figure 20:
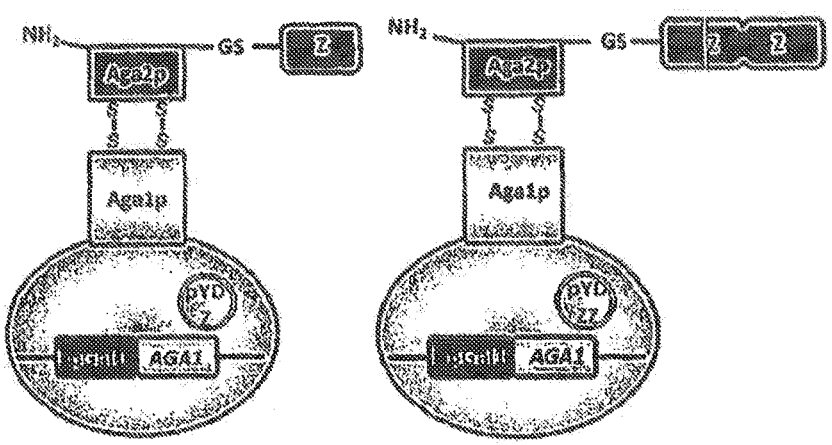

FIG. 20: Aga2p-mediated surface display of the Z and ZZ domain.

Surface display of the monovalent Z domain (A) and the divalent ZZ domain (B) in each case as an Aga2p fusion. Aga1p is coded chromosomally and the AGA1 expression is regulated by the galactose-inducible Gal1 promoter (pGal1). The Aga2p fusions are coded episomally (pYD-Z and pYD-ZZ). Their expression is likewise regulated by the Gal1 promoter. Z domains and ZZ domains are bound to the C terminus of the subunit Aga2p via a glycine-serine linker (Gly/Ser).

Figure 21A:
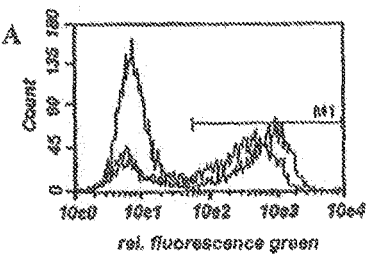
Figure 21B:
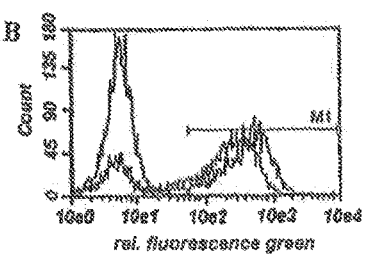

FIG. 21A and FIG. 21B: Flow cytometry and surface display of the Z and ZZ domain on EBY100 cells.

Flow cytometry analyses of EBY100 cells which display Aga2p, Aga2p-Z and Aga2p-ZZ on their surface. Fluorescence marking was carried out by means of protein A-specific FITC-conjugated detection antibodies from the goat after 24 hours of expression (FIG. 21A) and 72 hours of expression (FIG. 21B). The average rel. fluorescence intensity of the constructs and the percentage content of cells within the marker region M1 is additionally given.

FIG. 22A, FIG. 22B and FIG. 22C: Transmitted light and fluorescence microscopy photographs of ZZ-displaying cells Transmitted light (FIG. 22A) and fluorescence microscopy photograph (FIG. 22B) of Aga2p-ZZ-displaying EBY100 cells and Aga2p-displaying EBY100 cells (FIG. 22C) shown. Detection was carried out in (FIG. 22B) and (FIG. 22C) with a protein A-specific FITC-conjugated antibody from the goat.

FIG. 23: IgG binding by the Z and ZZ domain and flow cytometry.

Flow cytometry analysis of Z and ZZ domains-displaying EBY100 cells (pYD-Z and pYD-ZZ transformants) after 24 hours of expression. Marking was carried out with the antibody cetuximab (1 µM), b-hsEGFR (1 µM) and SA-PE. The average rel. fluorescence and the percentage content of cells within the marker region M1 is additionally shown. Negative control: Aga2p (pYD1 transformants).

FIG. 24: Surface display of VHH-Fc fusion proteins.

The surface display was mediated by the ZZ domain anchored covalently on the cell surface. The cells were marked in (A) and (B) with b-hsEGFR/SA-PE. The result of the FACS analysis without (−PEG) and with addition of PEG8000 (+PEG) after 24 hours is shown in (A), after 72 hours in (B). Marking was carried out by means of b-hsEGFR and SA-PE. (C) shows the detection of the ZZ domain of both cultures after 24 hours by the marking with a protein A-specific FITC-conjugated antibody from the goat.

Figure 25:
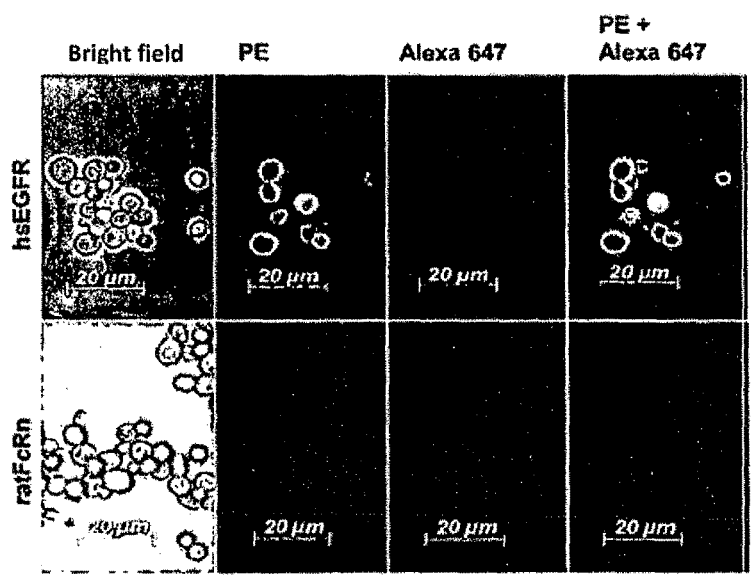

FIG. 25: Transmitted light and fluorescence microscopy analysis of VHH-Fc-displaying cells.

Fluorescence microscopy photographs of EBY100 cells which, mediated by the ZZ domain, displayed the VHH-Fc fusion protein on their surface. The cells were marked on the one hand with b-hsEGFR/SA-PE (row: hsEGFR) and on the other hand with b-rFcRn (*Rattus norvegicus*)/SA-PE (row: ratFcRn) (column: PE). A further marking with an Fc-specific antibody was additionally carried out (column: Alexa 647). The overlapping of the two fluorescence signals is shown in the column PE+Alexa 647.

FIG. 26A, FIG. 26B, FIG. 26C, and FIG. 26D: Non-covalent surface display of IgG molecules.

Two-colour marking and flow cytometry after (FIG. 26A) 24 and (FIG. 26B) 48 hours. The yellow fluorescence (rel. fluorescence yellow) shows the signal for phycoerythrin and therefore the binding of b-hsEGFR; the red fluorescence (rel. fluorescence red) shows the signal for AlexaFluor 647™ (Fc signal). 24 hours: 36.4% of the cells within the marker region M1, 48 hours: 43.4% of the cells within the marker region M1. (FIG. 26C) Control: cells from (A) marked with SA-PE. 0.2% of the cells within the marker region M1. (FIG. 26D) shows in a highly simplified form the surface display of the IgG molecule by the ZZ domain (green) covalently anchored via Aga2p (pale blue) and Aga1p (dark blue). The grey arrow indicates the soluble secretion of the light and heavy IgG chain.

FIG. 27A, FIG. 27B and FIG. 27C: Covalent surface display of IgG molecules.

Two-colour marking of IgG-displaying EBY100 cells after (FIG. 27A) 24 hours and (FIG. 27B) 72 hours. The yellow fluorescence (rel. fluorescence yellow) shows the signal for SA-PE and therefore the binding of the biotinylated antigen (b-hsEGFR); the red fluorescence (rel. fluorescence red) shows the signal for AlexaFluor™ 647 (Fc-specific antibody). (FIG. 27C) shows in a highly simplified form the theoretically assumed surface display of the IgG molecule as a covalent Aga2p fusion in the case of a successful assembling of the light and heavy IgG chain.

FIG. 28A, FIG. 28B and FIG. 28C: FACS analysis of the stability of the VHH-Fc:ZZ interaction.

FACS histograms of VHH-Fc-displaying EBY100 cells. (FIG. 28A) Surface display of marked VHH-Fc (red) and surface display of non-marked VHH-Fc (black). (FIG. 28B) Initial 1:1 mixture at time $T_0$. (FIG. 28C) 1:1 mixture after 32 hours. Detection of the VHH-Fc fusion protein via b-hsEGFR and SA-PE.

Figure 29:
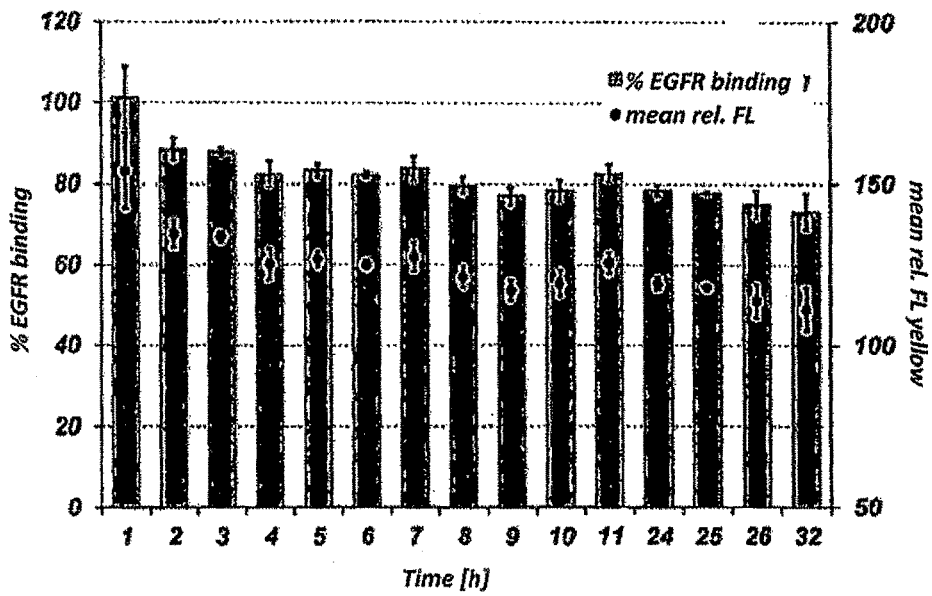

FIG. 29: VHH-Fc:ZZ interaction over a period of 32 hours.

Figure 26A:
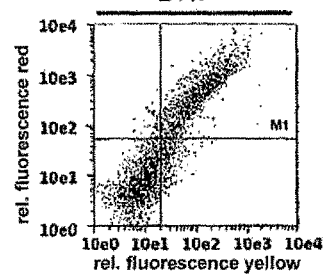
Figure 26B:
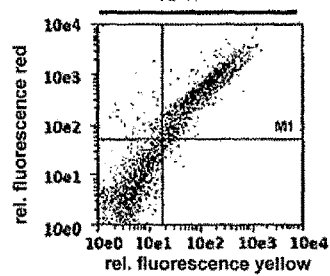
Figure 26C:
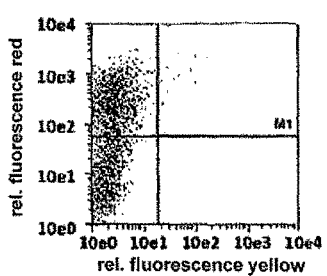
Figure 26D:
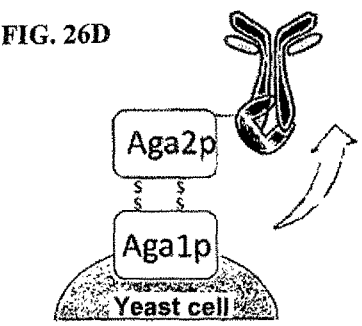

Graphical presentation of the average relative fluorescence of the M1 population after various points in time (■) and the resulting percentage binding content between the ZZ domain and VHH-Fc ( ) compared with the initial measurement (FIG. 26B).

Figure 30:
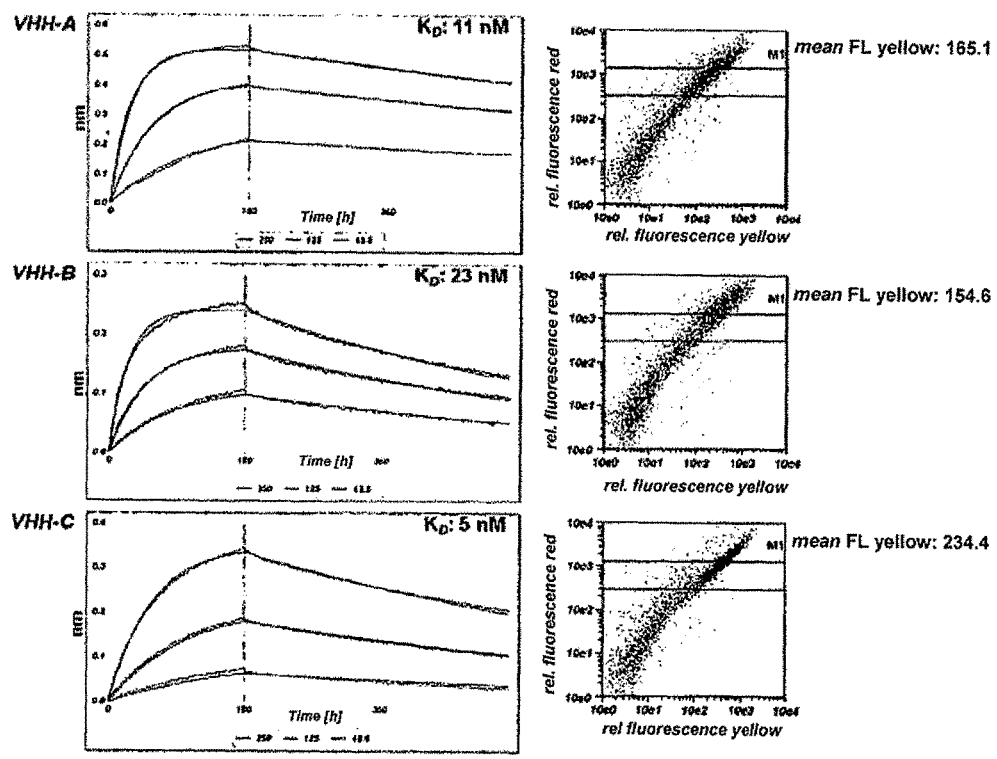

FIG. 30: Octet and FACS analyses of the binding of var. VHH-Fc fusion proteins and hsEGFR.

The biomolecular interactions of the three VHH domains (VHH-A, VHH-B, VHH-C) with the antigen (hsEGFR) were analysed by means of biolayer interferometry and FACS. Mean fl. yellow (rel. fluorescence yellow) reproduces the average relative fluorescence intensity of the cells located in M1 of the FACS measurement (FACS). The processed measurement values of association and dissociation of the interaction of the VHH domains with soluble antigen (250 nM, 125 nM and 62.5 nM hsEGFR) are shown in the biolayer interferometry column.

Figure 31:
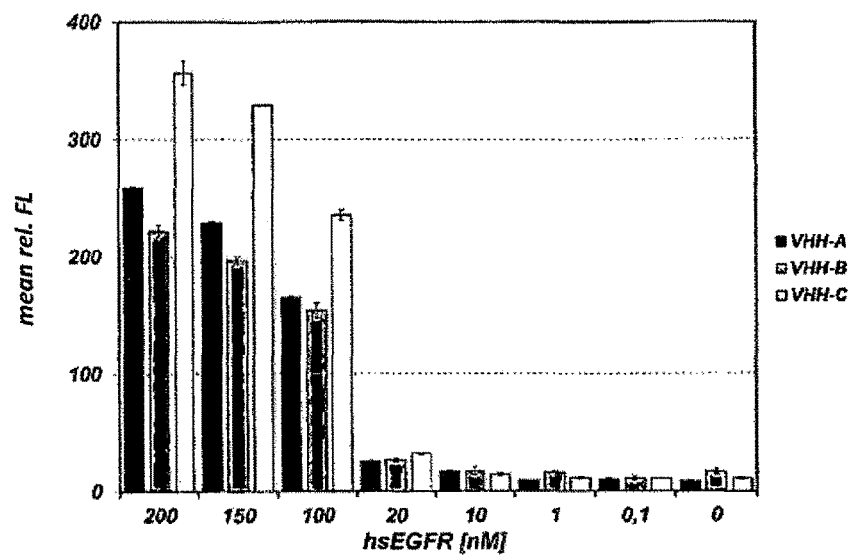
Figure 32A:
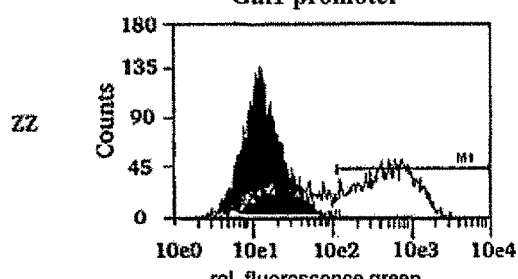
Figure 32B:
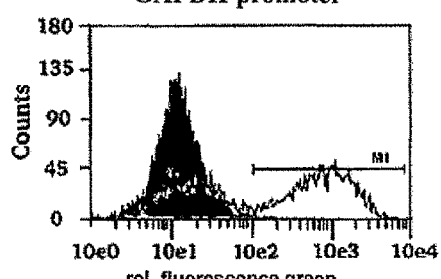
Figure 32C:
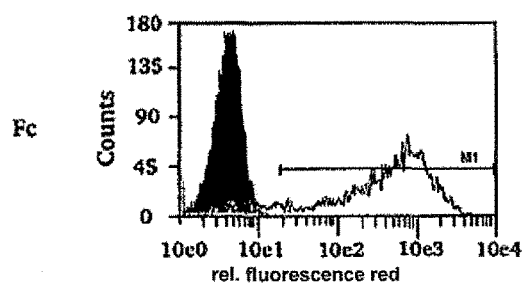
Figure 32D:
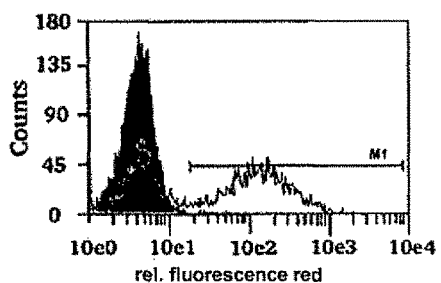

FIG. 31: Graphical presentation of the FACS analysis of the binding of various VHH-Fc fusion proteins (A, B, C) to the antigen hsEGFR.

Average rel. fluorescence signals for the binding of hsEGFR of three VHH domains (VHH-A, VHH-B, VHH-C) which were displayed as an Fc fusion on EBY100 cells via the interaction with the ZZ domain. In each case the same numbers of cells were marked with various hsEGFR concentrations (200 nM to 0 nM) and SA-PE and analysed by flow cytometry. After standardisation of the signal of the surface display the fluorescence signals were plotted against the concentrations. Error bars represent three independent measurements.

FIG. 32A, FIG. 32B, FIG. 32C and FIG. 32D: FACS analysis of switchable surface display.

FACS histograms for investigation of the switchable secretion of VHH-Fc fusion proteins. (FIG. 32A) and (FIG. 32C) pYD-pGal-app8-VHH1-Fc/pYD-ZZ. (FIG. 32B) and (FIG. 32D) pYD-pGAPDH-app8-VHH1-Fc/pYD-ZZ. Detection of the ZZ domain was carried out via a protein A-specific antibody from the goat (FITC conjugate). Detection of the VHH-Fc fusion protein via an Fc-specific F(ab')$_2$ fragment (AlexaFluor™ 647 conjugate). Grey: cultivation in glucose-containing medium, red: cultivation in galactose-containing medium.

Figure 33:
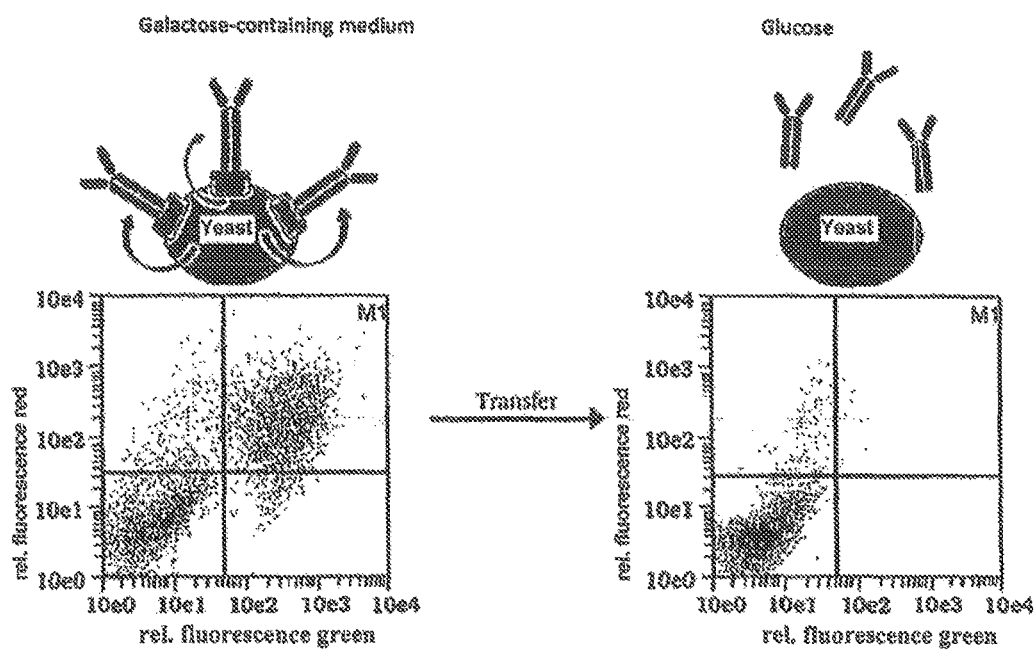

FIG. 33: Selective changing between surface display and soluble production.

Two-colour marking and flow cytometry of EBY100. The cultivation of cells in galactose-containing medium (+PEG8000) is shown in (A). The rel. fluorescence green shows the surface display of the ZZ domain. The rel. fluorescence red shows the surface display of the VHH-Fc fusion proteins displayed non-covalently. By the transfer of the cells into glucose-containing medium (+PEG8000) (B) the ZZ domain and VHH-Fc fusion protein are no longer detectable on the cell surface (cf. M1 A and M1 B).

Figure 34:
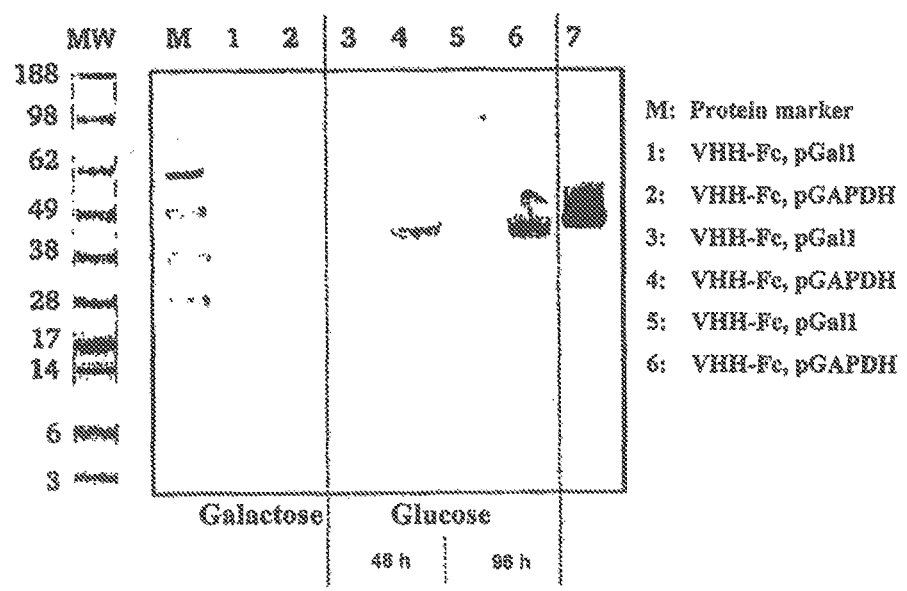

FIG. 34: Analysis of the switchable secretion of VHH-Fc fusion proteins.

Western blot analysis of the protein fractions precipitated by means of TCA in the supernatant of VHH-Fc expression cultures. The behaviour of the Gal1 promoter and of the GAPDH promoter in galactose- and glucose-containing medium was investigated. Detection of the VHH-Fc fusion proteins on the PVDF membrane was carried out via an Fc fragment-specific primary antibody (rabbit) and a rabbit-specific POD-conjugated secondary antibody (goat).

Figure 35:
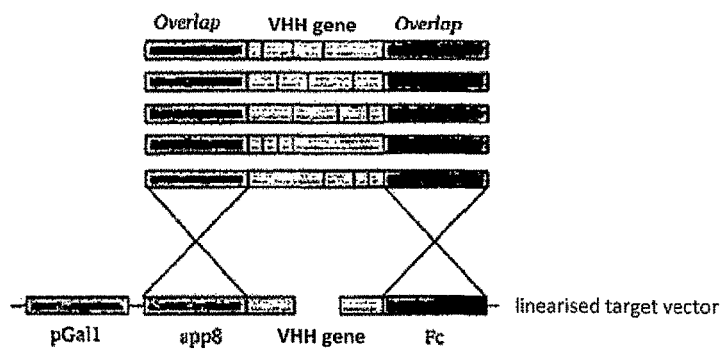

FIG. 35: Cloning strategy of the VHH libraries.

Diagram of the cloning strategy for the production of the VHH libraries. The mutated variants of the VHH sequence (red) are incorporated into the linearised target vector via homologous regions (overlap) at the ends of the PCR products. Use is made here of the mechanism of homologous recombination in yeast cells.

Figure 36A:
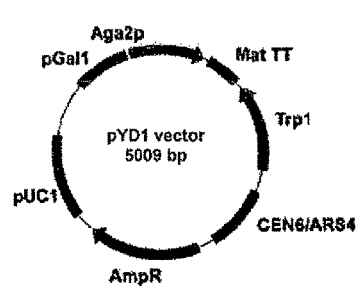
Figure 36B:
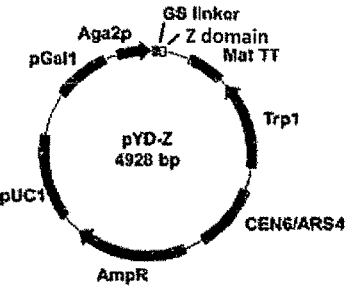
Figure 36C:
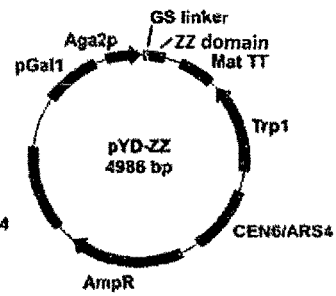
Figure 37A:
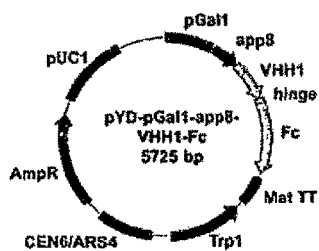
Figure 37B:
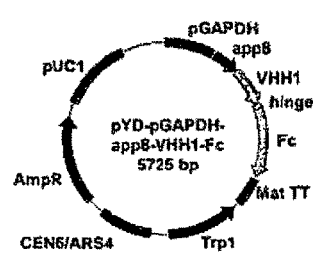
Figure 37C:
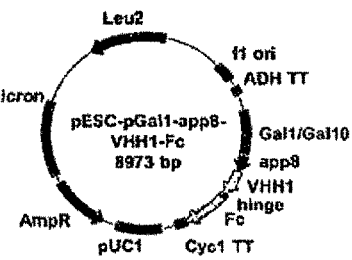
Figure 37D:
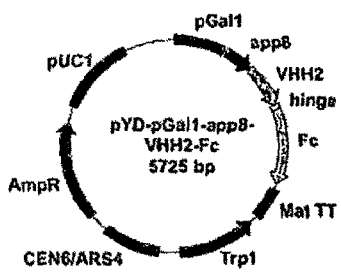
Figure 37E:
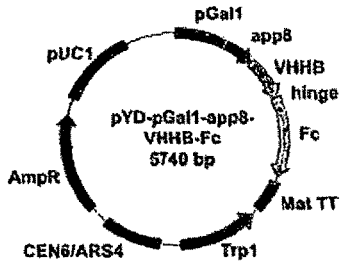
Figure 37F:
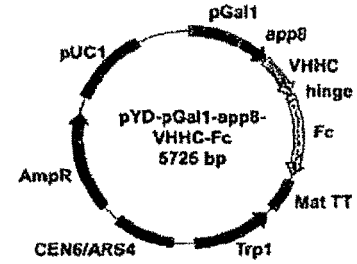

FIG. 36A, FIG. 36B and FIG. 36C: Plasmids for surface display of he Fc binding domain.

(FIG. 36A) Diagram of the plasmid pYD1 for surface display of Aga2p fusion proteins on the surface of EBY100 cells (Invitrogen) and the plasmids for surface display of the Z domain pYD-Z (FIG. 36B) and the ZZ domain pYD-ZZ (FIG. 36C) as an Aga2p fusion. pYD-ZZ additionally also existed with a G418 resistance cassette instead of the auxotrophic marker Trp1 and is called pYD-ZZ-G418 (plasmid map not shown).

FIG. 37A, FIG. 37B, FIG. 37C, FIG. 37D, FIG. 37E and FIG. 37F: Plasmids for soluble secretion.

Diagram of the plasmids for soluble secretion. All the plasmids code for the signal peptide app8 for soluble secretion. (FIG. 37A, FIG. 37B and FIG. 37C) Secretion plasmids for the hsEGFR-specific VHH domain; expressed as an Fc fusion protein. (FIG. 37D) Secretion plasmid for the Trx-specific VHH domain, expressed as an Fc fusion protein. (FIG. 37E) Secretion plasmid for the VHH domain B. (FIG. 37F) Secretion plasmid for the VHH domain C.

Figure 38A:
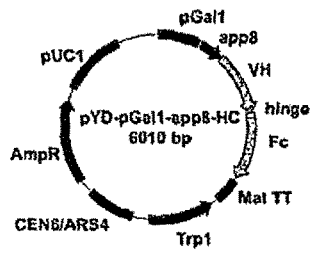
Figure 38B:
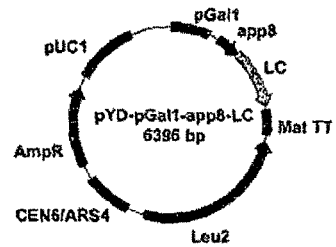
Figure 38C:
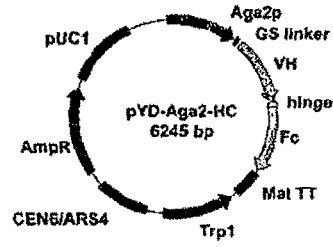

FIG. 38A, FIG. 38B and FIG. 38C: Plasmids for soluble secretion of IgG molecules. Plasmids for soluble secretion of (FIG. 38A) the heavy and (FIG. 38B) the light chain of the IgG molecule matuzumab mediated by the signal peptide app8. (FIG. 38C) Plasmid for expression of the heavy chain of matuzumab as an Aga2p fusion.

FIG. 39A, FIG. 39B, FIG. 39C and FIG. 39D: Plasmids for chromosomal PDI integration.

Figure 39A:
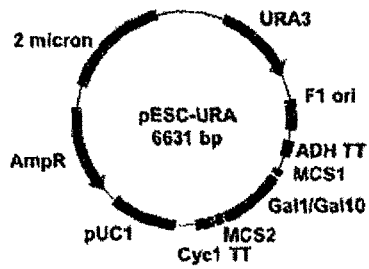
Figure 39B:
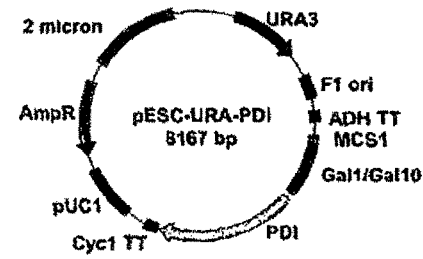
Figure 39C:
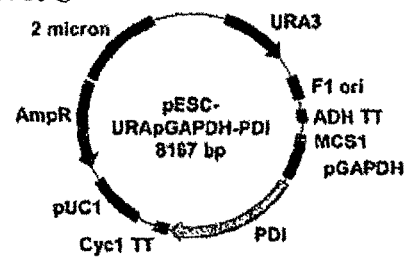
Figure 39D:
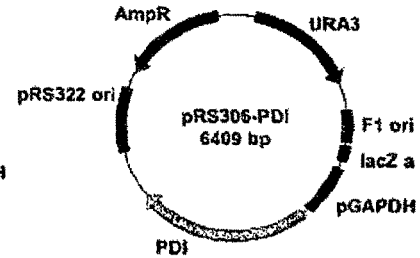

(FIG. 39A) pESC-URA vector from Agilent Technologies Inc. FIG. 39B) pESC-URA vector with the PDI sequence. (FIG. 39C) pESC-URA vector with the PDI sequence and GAPDH promoter (PDI expression cassette). (FIG. 39D) pRS306 integration vector for chromosomal integration of the PDI expression cassette and overexpression of the oxidoreductase PDI.

The following examples illustrate the invention without limiting it. In particular, individual particular embodiments, physical, biological or chemical parameters or materials can be generalised if this is readily possible to the person skilled in the art.

EXAMPLES (A) Materials, Cells and Media Used
  (i) Yeast Strains Used:
    EBY100: MATa URA3-52 trp1 leu2Δ1 his3Δ200pep4::HIS3prb1Δ1.6R can1 GAL (pIU211:URA3). Part of the "Yeast Display Vector Kit", Invitrogen, Germany
    BJ5464: MATa URA3-52 trp1 leu2Δ1 his3Δ200 pep4::HIS3 prb1Δ1.6R can1 GAL (ATCC No. 208288)
    EBY100 URA$^-$: Generated by 5-FOA selection. Biochemie, AK Prof. Kolmar, TU Darmstadt, Germany
    BJ5464-URA$^-$: Generated by 5-FOA selection, Merck Serono, Merck KGaA, Germany
    APO-E: EBY100-URA$^-$ and integration of the vector pRS306-PDI
    APO-B: BJ5464-URA$^-$ and integration of the vector pRS306-PDI
  (ii) Nutrient Media for Cultivation of Yeast Cells
    YPD medium: 20 g dextrose
      20 g peptone
      10 g yeast extract
    The components were dissolved in sterile water, 10 ml of PenStrep Mix were added and the mixture was topped up to 1 l with sterile water. After sterile filtration the medium was stored at 4° C. for a maximum of two months. For agar plates 1.5% agar was added to the medium and the medium was autoclaved at 121° C. for 20 minutes.

(iii) Glucose-Containing SD Medium+PEG8000:

26.7 g of base mix (Minimal SD Base) were dissolved in 490 ml of sterile water and the solution was autoclaved at 121° C. for 15 minutes. The desired DO mix was dissolved separately in 100 ml of sterile water with 5.4 g of $Na_2HPO_4$ and 8.56 g of $NaH_2PO_4 \times H_2O$ and the solution was likewise autoclaved at 121° C. for 15 minutes. In a further batch, 110 g of PEG8000 were dissolved in 400 ml of sterile water, while stirring. All the components were mixed, 10 ml of PenStrep Mix were added and the mixture was sterile-filtered. It was stored at room temperature for a maximum of four weeks.

(iv) Galactose-Containing SD Medium:

For induction of the Gal1 promoter, instead of 26.7 g/l of base mix (Minimal SD Base) 37 g of galactose-containing base mix (Minimal SD Base Gal/Raf) (Clontech laboratories Inc.) was used. The base mix was dissolved in 890 ml of sterile water and the solution was autoclaved at 121° C. for 15 minutes. The desired DO mix was dissolved separately in 100 ml of sterile water with 5.4 g of $Na_2HPO_4$ and 8.56 g of $NaH_2PO_4 \times H_2O$ and the solution was likewise autoclaved at 121° C. for 15 minutes. After the two solution had been cooled, the base and DO mix were combined and 10 ml of PenStrep Mix were added. The medium was stored at room temperature for a maximum of four weeks.

(v) Galactose-Containing SD Media +PEG8000:

37 g of base mix (Minimal SD Base Gal/Raf) were dissolved in 490 ml of sterile water and the solution was autoclaved at 121° C. for 15 minutes. The desired DO mix was dissolved separately in 100 ml of sterile water with 5.4 g of $Na_2HPO_4$ and 8.56 g of $NaH_2PO_4 \times H_2O$ and the solution was likewise autoclaved at 121° C. for 15 minutes. In a further batch, 110 g of PEG8000 were dissolved in 400 ml of sterile water, while stirring, and the solution was added to the autoclaved medium. After complete mixing of all the components the batch was sterile-filtered and 10 ml of PenStrep Mix were added. The medium was stored at room temperature for a maximum of four weeks.

For selection of transformant with episomally coded G418 resistance 150 mg/l of genetecin were added to the galactose-containing SD medium +PEG8000.

Example 1: Preparation of a Method for Non-Covalent Surface Display on Yeast Cells and Soluble Production The aim of the present work was the development of a method for non-covalent surface display of IgG molecules and Fc fusion proteins on yeast cells, the associated selection and the subsequent switchable secretion of the selected protein into the medium of an expression culture for biochemical characterisation thereof. The method for non-covalent surface display on yeast cells was realised by the interaction of the Fc binding domain derived from protein A and covalently anchored on the cell surface and the co-expression of a VHH-Fc fusion protein or an IgG molecule. The soluble secretion of the VHH-Fc fusion proteins into the culture supernatant was achieved by modification of the expression conditions. As a result time-consuming reformatting steps of the expression plasmid which are necessary for soluble production of the selected clone e.g. in comparable selection methods, such as surface display on phages[136] or surface display as a covalent Aga2p fusion[92], are dispensable. For validation of the method VHH-Fc fusion proteins were used in order to reduce the complexity of the experiments compared with the use of whole IgG molecules, since the VHH-Fc fusion is a protein which, in contrast to an IgG molecule, is built up not from four but merely from two chains (FIG. 4). In the first section of the results shown here the generation of a yeast strain which overexpresses PDI (protein disulphide isomerase), and of which an improved soluble secretion of VHH-Fc fusion proteins was expected and could be shown, is demonstrated. The secretion of VHH-Fc fusion proteins, the optimisation of the secretion and the characterisation of the VHH-Fc fusion proteins secreted by the yeast is then demonstrated in order to check their functionality. The surface display of an Fc binding domain derived from protein A on yeast cells and the co-expression with solubly secreted VHH-Fc fusion proteins and surface display thereof is demonstrated in the following. In this case the Fc binding domain served as the mediator molecule of the non-covalent surface display of the VHH-Fc fusion proteins by the interaction with the Fc part. In addition the presentation behaviour of the Fc binding domain on the surface of yeast cells and the functionality thereof with respect to binding of human IgG molecules was analysed. In order to render possible the isolation of clones having the desired property from generated variant libraries using the non-covalent method by means of a high throughput method, the stability of the genotype-phenotype coupling was validated in advance with the aid of mixing experiments. For experimental testing and for investigation of the genotype-phenotype coupling of this non-covalent surface display of VHH-Fc fusion proteins, the results of two mixing experiments and the production and characterisation of three generated VHH-based libraries and the screening of one of these libraries for VHH variants having a new property are then demonstrated.

Example 2: Generation of a Yeast Strain which Overexpresses PDI

The oxidoreductase PDI (protein disulphide isomerase) is an ER-located enzyme which catalyses the oxidation and reduction of disulphide bridges in substrate proteins[137]. It has been demonstrated in an already published study that overexpression of this enzyme leads to an increased secretion of scFv fragments from the yeast[118]. Rakestraw and colleagues showed in 2009 that the overexpression of PDI led to a significant increase in the amount of IgG secreted from yeast cells and that the integration of a PDI expression cassette into the yeast genome is preferable to an episomal expression of the PDI for increasing the secretion of heterologous proteins[111]. The results of the generation of the *S. cerevisiae* strain APO-E are presented in the following. It was presumed in advance that PDI overexpression increases the secretion output of the yeast strain for VHH-Fc fusion proteins. This yeast strain was generated by chromosomal integration of a PDI expression cassette into the genome of EBY100. The production of the *S. cerevisiae* strain APO-B was carried in a comparable manner (data not shown). In this case the PDI expression cassette was integrated chromosomally into the strain BJ5464 in the same manner. For amplification of the oxidoreductase PDI intrinsic to the yeast chromosomal DNA was extracted from an EBY100 culture growing under stationary conditions. By means of gap repair PCR and using the oligodeoxyribonucleotides PDI-GR-up and PDI-GR-rp, the sequence of the PDI with homologous regions to the target vector pESC-URA was amplified. 1 µl of the chromosomal DNA preparation served as the matrix for the PCR. The gene sequence was then cloned into the target vector by means of homologous recombination. To initiate the homologous recombination the target vector was linearised beforehand with the restriction endonuclease XhoI. Electrocompetent EBY100 URA⁻ cells were transformed with the target vector and the PCR product of the PDI gene sequence. The yeast strain EBY100 URA⁻ was kindly made available by Stefan Zielonka (Biochemistry, TU Darmstadt, AK Prof. Kolmar). For this strain the auxotrophic marker URA3 was mutated beforehand by 5-fluoro-orotic acid selection[138]. After checking the cloning by means of sequencing, in a second cloning step the inducible promoter Gal1/10 of the generated vector pESC-URA-PDI was substituted for the constitutively expressing promoter GAPDH in order to produce the vector pESC-pGAPDH-PDI. For this purpose the DNA sequence of the GAPDH promoter from the plasmid pGAPZA (Life Technologies Corp.) was amplified using the oligodeoxyribonucleotides GAPDH-up and GAPDH-rp and the vector pESC-URA-PDI was linearised using the restriction endonuclease BstAPI and purified. Thereafter the transformation of electrocompetent EBY100 URA⁻ cells with the linearised target vector and the GAPDH PCR product was carried out for cloning by means of homologous recombination in yeast cells. After selection had taken place and renewed sequencing, electrocompetent EBY100 URA⁻ cells were transformed with the plasmid pESC-URA-pGAPDH-PDI. The episomal expression of the PDI was checked by means of western blot analysis (FIG. 4). For this purpose a 50 ml culture was grown in suitable glucose-containing SD medium. The initial cell density was $3 \times 10^6$ cells/ml. Starting from this culture, a further culture (50 ml) was then prepared in galactose-containing medium in order to check the gene expression additionally in galactose-containing medium. Both cultures were cultivated to a cell density of $3 \times 10^7$ cells/ml at 30° C. and thereafter $2 \times 10^7$ cells were removed at defined points in time and processed for western blot analysis. The illustration of the western blot analysis is shown in FIG. 5 and represents the intracellular content of the oxidoreductase PDI. The specific detection was carried out with a PDI-specific antibody from the mouse. Detection on the PVDF membrane was then carried out with a mouse-specific antibody (POD conjugate) from the goat. The western blot analysis shown in FIG. 5 illustrated that the episomally coded PDI was expressed both in glucose- (FIG. 5 lane 2) and in galactose-containing medium (FIG. 5 lane 3 to 7) and it was possible to detect it in the cell lysate via the PDI-specific detection antibody. This finding is to be attributed to the regulation of PDI expression by the constitutively expressing GAPDH promoter. Compared with the negative control (EBY100 URA⁻ cells, FIG. 5 lane 1), a significantly stronger signal was to be recorded in the western blot. The generation of the strain APO-E which overexpresses PDI is demonstrated in the next step. For production of APO-E the PDI expression cassette comprising the sequence for the GAPDH promoter and the sequence for PDI was integrated into the yeast genome of EBY 100. For this purpose the sequence of the PDI expression cassette was cloned into the integration vector pRS306 (ATCC). In addition the recognition sites of the restriction endonucleases XhoI and XbaI were attached to the expression cassette by means of PCR. The oligodeoxyribonucleotides XbaI-PDI-up and XhoI-PDI-rp were used. After the purification of the PCR product, the endonucleolytic restriction of the PCR product and of the target vector pRS306 was carried out. Ligation of the target vector pRS306 with the cleaved expression cassette (pGAPDH-PDI) using T4-DNA ligase and the transformation of chemically competent *E. coli* TOP10 cells followed. By growing five clones, their plasmid isolation and sequencing, it was possible to identify a clone with the correct sequence (pRS306-PDI). This was used for the integration of the PDI expression cassette into the genome of EBY100. For preparation for the chromosomal integration a preparative plasmid isolation of the vector pRS306-PDI was carried out as described. Thereafter linearisation of the plasmid was carried out using the restriction endonuclease BstBI 2.5 µg of the linearised vector were then used for transformation of EBY100 URA⁻ cells and as a result the specific integration of the PDI expression cassette into the yeast genome was rendered possible. After selection on SD-URA agar plates had taken place, the chromosomal integration of the vector pRS306-PDI was investigated experimentally by means of western blot analysis. For this purpose six clones were cultivated in YPD medium and then transferred into suitable galactose-containing SD medium. After four days in each case $2 \times 10^7$ cells were removed and prepared under the conventional conditions for analysis of the PDI expression by means of western blot. The results of this are shown in FIG. 6. By the specific detection of the oxidoreductase PDI in the cell lysates of the six yeast cultures (FIG. 6) it was possible to confirm successful overexpression of the PDI (FIG. 6 lane 2-4). Compared with the APO-E clones, the sample of the EBY100 strain showed a significantly weaker signal in the western blot (FIG. 6 lane 1). This finding indicated the successful integration of the vector pRS306-PDI into the genome of the strain EBY100 URA⁻ and demonstrated that the oxidoreductase PDI was expressed in this strain to a greater extent than in the strain EBY100. In conclusion, for stable chromosomal integration of the PDI expression cassette the URA3 marker used for the selection was mutated by means of 5-fluoro-orotic acid. The direct applicability of the strain APO-E with reference to the secretion of the VHH-Fc fusion protein is demonstrated in the following.

Example 3: Secretion of VHH-Fc Fusion Proteins

In this section the results of the soluble secretion of VHH-Fc fusion proteins from yeast cells are presented in order to check the secretion output of the *S. cerevisiae* strains EBY100 and APO-E for VHH-Fc fusion proteins. Since VHH is a single-chain domain, the complexity of the experimental set-up was therefore reduced compared with the use of whole, multichain IgG molecules. In addition to the secretion output of the individual strains, the influence of the gene dose on the secreted amount of protein was also investigated. For this purpose expression plasmids which had different replication origins (oris) and were generated beforehand via homologous recombination in yeast cells were used. For this purpose the DNA sequence of the VHH-Fc construct was amplified with specific oligodeoxyribonucleotides from the plasmid pYD-pGal1-app8-VHH1-Fc and cloned into the linearised vector pESC-Leu. As a result the vector pESC-pGal1-app8-VHH1-Fc with the 2 micron on was generated. A plasmid with the on CEN6/ARS4 is distinguished by a low and a plasmid with the ori 2 micron by a high number of copies within a cell[139]. At the start electrocompetent APO-E and EBY100 cells were transformed with the plasmids pYD-pGal1-app8-VHH1-Fc and pESC-pGal1-app8-VHH1-Fc for soluble secretion of the hsEGFR-specific VHH-Fc fusion protein. Both plasmids also coded for the signal peptide app8 for soluble secretion in addition to the VHH gene sequence. For the expression suitable galactose-containing SD media with addition of 11% (w/v) PEG8000 and without addition of PEG8000 were used in order additionally to determine the influence of PEG8000 on the secreted amount of the VHH-Fc fusion protein in the culture supernatant. It was presumed in advance that the addition of PEG8000 can have an advantageous effect on the secretion of heterologous proteins, since it was already pointed out in the literature that PEG can have a positive influence on the secretion of heterologous proteins[140]. At given points in time (24, 48, 96 h) samples of the culture supernatant were taken and the proteins contained in the supernatant were precipitated by means of trichloroacetic acid. Sample processing of the cell lysates was carried out in a corresponding manner. Marking of the VHH-Fc fusion proteins was carried out on the on the PVDF membrane via an Fc-specific primary antibody from the rabbit and a POD-conjugated rabbit-specific secondary antibody from the goat. The results are shown in FIG. 7. In both constructs the glycosylation site in the Fc part at position 297 was mutated beforehand by means of site-specific mutagenesis in order to prevent the hypermannosylation known from yeast during the N-glycosylation. For this purpose the mutagenesis of this position was carried out by means of PCR and using the oligodeoxyribonucleotide N-Q-HC-mut. A facilitated and improved secretion of the protein by the yeast was hoped for from this. FIG. 7 A shows the successful expression of the VHH-Fc construct and soluble secretion thereof by cultivation of EBY100 transformants without addition of PEG8000. The proteins were detected specifically in the cell lysate (lane 1) after 24 hours and in the culture supernatant (lane 2) after 96 hours. The volume of supernatant analysed (lane 2) corresponded to the equivalent volume of $5 \times 10^7$ cells. The VHH-Fc protein was found (non-reduced) in this in monomeric (~40 kD) and also in dimerised form (~90 kD) only after an expression time of 96 hours. Two VHH-Fc-specific bands were likewise detected in the cell lysate (FIG. 7 lane 1). It was possible for the bands with the lower molecular weight to be assigned to the monomeric VHH-Fc protein (~40 kD), since they had a size of between 38 kD and 49 kD. With the aid of the sequence analysis program Lasergene® (DNASTAR Inc.) a molecular weight of 39.6 kD was determined in advance for the monomeric VHH-Fc fusion protein. The second band had a slightly higher molecular weight (FIG. 7 lane 1). This larger protein form was to be expected in the case where processing of the VHH-Fc fusion protein had not taken place since the signal peptide app8 has a size of 8.7 kD and in the case of non-processing by the cellular signal peptidase the molecule size of the VHH-Fc fusion protein is visibly increased in the western blot. The following FIG. 8 shows the diagram of the non-processed (FIG. 8A) and the processed (FIG. 8 B) form of the protein. The results of the western blot analysis of the culture supernatants of APO-E transformants after 24 and 48 hours are shown in FIG. 7 B. The culture volumes plotted were volumes which were equivalent to $1 \times 10^7$ cells. In this case the supernatant of a five times lower amount of cells compared with FIG. 7 A lane 2 was analysed. FIG. 7 B additionally shows the comparison between the secretion of the VHH-Fc fusion protein into the culture supernatant of a CEN6/ARS4 plasmid (lane 3 and 5) and of a 2 micron plasmid (lane 4 and 6). The gene expression of the two plasmids was carried out under identical conditions. In contrast to FIG. 7 A, cultivation of the cells during the gene expression was carried out in the presence of 11% (w/v) PEG8000. In FIG. 7 C the cell lysates correlating to 7 B have been analysed by means of western blot. As can be seen it was possible to detect both the CEN6/ARS4 plasmid-coded (FIG. 7 B, lane 3) and the 2 micron plasmid-coded VHH-Fc fusion protein (FIG. 7 B, lane 4) successfully in the culture supernatant. A clear signal was already detectable after 24 hours, in contrast to cultivation without PEG8000 (data not shown). This indicated a greater secretion of the protein in the presence of PEG8000. In addition a significantly lower amount of protein was found in the culture with the 2 micron plasmid in an equivalent culture volume, since weaker band signals were detected (cf. FIG. 7 B lane 3 and 5 with lane 4 and 6). In the analysis of the cell lysates (FIG. 7 C) it became clear that it was possible to detect a VHH-Fc-specific signal only in the cell lysate of the 2 micron culture (lane 8). This finding indicated a less efficient secretion of the protein using a 2 micron plasmid, in spite of the higher gene dose, than when a CEN6/ARS4 plasmid was used. The band signal had a molecular weight which corresponded to the size of the non-processed form (FIG. 8 A). The sample of the cell lysate from the CEN6/ARS4 culture investigated showed a VHH-Fc-specific signal neither at 24 hours nor at 48 hours. It was no longer possible to detect the VHH-Fc protein intracellularly here, which indicates an effective secretion of the protein. It was possible to confirm that the expression and soluble secretion of VHH-Fc fusion proteins delivered significantly higher protein yields in the presence of 11% (w/v) PEG8000 than in the PEG-free medium. Using a CEN6/ARS4 plasmid it was likewise possible for a significantly larger amount of protein to be secreted and detected than when the 2 micron plasmid was used. In the case of expression without PEG8000, it was possible to detect two forms of the protein of different size intracellularly; a larger non-processed and a smaller processed form. On analysis of the cell lysate from the PEG8000-containing expression culture with CEN6/ARS4 plasmid, none of the two intracellular protein forms was to be detected, whereas in the cell lysate of the PEG8000-containing expression culture with the 2 micron plasmid the occurrence of the non-processed protein form was observed. For further analysis of the influence of polyethylene glycol (specifically PEG8000) on the soluble secretion of VHH-Fc fusion proteins, starting from pYD-pGal1-app8-VHH1-Fc APO-E and EBY100 transformants in each case three different expression cultures were prepared, which differed exclusively in their PEG content (without PEG, 11% (w/v) PEG8000 and 11% (w/v) PEG1500). The aim was to investigate experimentally whether the molecular weight of the PEG used had an influence on the amount of protein secreted. After conclusion of the expression in galactose-containing SD medium a culture volume corresponding $1 \times 10^7$ cells was removed and after centrifugation the cell-free supernatant was prepared for western blot analysis. This was carried out under reducing conditions. Detection of VHH-Fc proteins on the membrane was carried out as described above via an Fc-specific detection antibody. The result of the western blot analysis is shown in FIG. 9. FIG. 9 illustrates that the addition of polyethylene glycol was decisive for a successful secretion of the VHH-Fc fusion protein in the culture supernatant. This applied both to EBY100 and to APO-E expression cultures. Without the addition of PEG, no protein was to be detected in the culture supernatant for the two strains (lane 1 and 4). In this experiment successful secretion of the protein in the volume of culture supernatant analysed was possible within 48 hours only in the presence of PEG8000. Furthermore, the molecular weight of the PEG used had a significant influence on the amounts of protein located in the supernatant. On the other hand, the used of a yeast strain which overexpresses PDI was less decisive. The results from FIG. 9 led to the conclusion that high molecular weight PEG8000 was more suitable for soluble secretion of the VHH-Fc fusion protein into the culture supernatant than the addition of PEG having a molecular weight of 1,500 kD. On the basis of the results described above, in all further experiments the addition of PEG8000 to the culture medium was used for the secretion of VHH-Fc fusion proteins. A more precise quantification of the amount of protein secreted from APO-E and EBY100 expression cultures and accordingly the influence of the PDI overexpression on the soluble protein yield in the culture supernatant is presented in the following.

Example 4: Quantification of VHH-Fc Fusion Proteins in the Culture Supernatants

The results presented here demonstrate the experimental analysis of the secretion output of the yeast strains APO-E and EBY100. As already mentioned, it was presumed that the overexpression of the oxidoreductase PDI has a positive influence on the soluble secretion of VHH-Fc fusion proteins. For this purpose electrocompetent EBY100 and APO-E cells were transformed with the plasmid pYD-pGal1-app8-VHH1-Fc and selected on selective agar plates. 50 ml expression cultures were prepared in galactose-containing medium +PEG8000. The initial cell density was $1 \times 10^7$ cells/ml. The protein concentrations in the culture supernatant were determined over a period of 120 hours. Analysis of the supernatant was carried out by means of biolayer interferometry using protein A biosensors as described. The concentrations determined over this period are presented on a graph in FIG. 10. 2% BSA was added to galactose-containing SD medium +PEG8000 as a negative control, a VHH-Fc fusion protein of known concentration of an HEK293 expression was used as a positive control. For calculation of the protein concentrations a calibration series with this protein was compiled in advance. It was possible to detect the VHH-Fc fusion protein in both cultures over a period of 120 hours (FIG. 10). The tendency to be observed was that a higher protein concentration was measured in the supernatant of the APO-E expression culture over the period than in the supernatant of the EBY100 culture. The highest protein concentration was measured after 96 hours in the APO-E culture (1.9±0.2 mg/l). Up to this point in time the protein concentration rose continuously, and thereafter fell to 0.7±0.1 mg/l (120 h). In the EBY100 expression culture significantly lower measurement values were achieved over the period compared with the APO-E expression culture. The highest protein concentration was indeed already to be measured here after 72 hours, but with a significantly lower value (1.2±0.2 mg/l) compared with APO-E. This was nevertheless below the protein concentration of the APO-E culture at 72 hours (cf. 1.8±0.2 mg/l). The protein concentration already started to fall again after 72 hours. After 120 hours a concentration of 0.5±0.1 mg/l was measured. A comparison of the protein concentration of the EBY100 with that of the APO-E expression culture after 96 hours makes it clear that the VHH-Fc protein concentration in the supernatant of the APO-E expression culture was virtually twice as high as the VHH-Fc concentration in the supernatant of the EBY100 expression culture. It was furthermore to be observed that the protein concentration in the EBY100 supernatant had reached the maximum value after a cultivation time of 72 hours. A further experiment was carried out as a control for the quantification of the VHH-Fc protein concentrations in the supernatant of yeast cultures. It was to be verified whether the signals from FIG. 10 detected by means of biolayer interferometry (Octet RED) were VHH-Fc-specific signals, since during analysis of the raw values it was observed that PEG8000 had an interfering effect on the measurement. Two measurement profiles for quantification of IgG molecules in the presence of PEG8000 and without PEG8000 are shown by way of example in FIG. 11.

The lower layer thicknesses of the loading of the protein A biosensors achieved in the presence of PEG8000 (FIG. 11 A) in contrast to the use of IgG molecules which were present in PBS for the loading (FIG. 11 B) were striking. In addition, in the presence of PEG8000 a significant noise of the measurement values and a delayed increase in the signals was to be observed. FIG. 11 illustrates the influence of PEG8000 on the biolayer interferometry measurement. Due to the addition of PEG8000 the viscosity of the medium was greatly increased. Clear interferences were to be observed during the loading of the bio sensors with the IgG molecule, which manifests itself by the delayed and non-uniform increase in the sensor signals in FIG. 11 A compared with FIG. 11 B. For the purpose of checking the biolayer interferometry measurement values, three independent expression cultures with a volume of 20 ml were prepared and the protein concentrations in the culture supernatants were determined by means of biolayer interferometry( ). To check the specificity of the signals, on the basis of these values a culture volume which corresponded to a defined VHH-Fc protein concentration was calculated. This culture volume was then investigated, after TCA precipitation of the proteins in the supernatant, in western blot via the specific detection with an Fc-specific antibody. For the biolayer interferometry measurement cultivation was carried out again for 120 hours. The cell density at the start of the experiment was $5 \times 10^6$ cells/ml. This time the two S. cerevisiae strains APO-E and APO-B which overexpress PDI were used for soluble secretion of the VHH-Fc proteins and the protein concentrations in the culture supernatants were determined by means of biolayer interferometry at given points in time. By comparison with a calibration series compiled beforehand, the protein concentrations were calculated from the raw values. The measurements were performed after 48, 72, 96 and 120 hours. The concentrations determined are presented in a graph. shows that it was possible for the VHH-Fc fusion protein to be detected from an expression duration of 48 hours in all the expression cultures via the interaction with protein A biosensors, and for the protein concentration of each culture to be determined. To verify the measurements, the culture volume of each culture after 120 hours which contained a theoretical amount of protein of 2 µg was calculated. These samples were then analysed by means of western blot. If the signal of the Octet measurement should have arisen by measurement error, which could occur for example by using highly viscous PEG8000-containing medium, this circumstance should be reflected in the western blot analysis. The calculated amount of culture supernatant was separated off from the yeast cells by centrifugation, and the proteins were precipitated by means of TCA and then prepared for the analysis by means of LDS-PAGE and western blot. Marking of the VHH-Fc proteins on the PVDF membrane was carried out by the interaction with an Fc-specific primary antibody from the rabbit and a rabbit-specific secondary antibody (POD-conjugated) from the goat. The results of the LDS-PAGE and the western blot analysis are presented in 13. It can be seen from 13 that the VHH-Fc fusion protein was successfully detected in all the samples by means of LDS-PAGE and western blot analysis. In the case of the western blot analysis the detection was carried out by an Fc-specific detection antibody. Since the signal strengths of the bands on the membrane estimated visually were virtually uniform, it was assumed that an approximately identical amount of protein from each expression culture was used for the LDS-PAGE and the western blot analysis. Since the amount of protein employed for LDS-PAGE and western blot analysis was calculated from the biolayer interferometry measurement carried out beforehand, the signals of the biolayer interferometry measurement were therefore to be confirmed. It was assumed that the measurement values achieved by means of biolayer interferometry arose due to the specific interaction of the VHH-Fc fusion protein with protein A of the biosensor surface, and that PEG8000 had no interfering influence on the measurement results.

Example 5: Soluble VHH-Fc Secretion and Affinity Chromatography

In a further experiment the VHH-Fc fusion protein was produced on a larger scale and then purified from the culture supernatant by means of protein A affinity chromatography. A further comparison of the secretion outputs of the strains APO-E and APO-B was additionally carried out. Thereafter the functionality of the purified protein with respect to the interaction with the specific antigen (hsEGRF) was investigated, since it is known from the literature that proteins expressed by yeast are often hyperglycosylated[141]. For this purpose electrocompetent APO-E and APO-B cells were transformed with the plasmid for soluble secretion of the VHH-Fc fusion protein (pYD-pGal-app8-VHH1-Fc) and selected on selective agar plates. Starting from a preculture, an expression culture was inoculated with a volume of 200 ml. The secretion of the VHH-Fc fusion proteins was carried out in the presence of 11% (w/v) PEG8000 for 96 hours, since it had already been demonstrated that this cultivation time was favourable for the secretion of VHH-Fc fusion proteins. After conclusion of the expression a culture volume of approx. 185 ml remained. The yeast cells were separated from the culture supernatant by centrifugation. Protease inhibitor (PIC III) (1:1,000) was then added to the supernatant in order to reduce the degradation of the protein by proteases in the culture medium and the mixture was transferred into Snakeskin™ dialysis tubes (MW 10 kD) (Thermo Scientific GmbH). The dialysis of the culture supernatant was carried out as described above. After conclusion of the dialysis the contents of the individual dialysis tubes were combined and used for affinity chromatography purification of the VHH-Fc fusion protein by means of a protein A HiTrap 1 ml column (GE Healthcare Europe GmbH). The volume after conclusion of the dialysis was approx. 400 ml. Due to the large increase in volume a reduction in the viscosity of the culture supernatant was observed. Since a certain residual viscosity still existed, however, it was to be assumed that the PEG8000 had not been completely removed from the supernatant. The reduction in the viscosity was accordingly to be attributed rather to the dilution of the culture supernatant than to the exchange of the PEG8000-containing medium for PBS. After conclusion of the purification and screening of the chromatogram (FIG. 14 A) the particular relevant elution fractions were combined. The exchange of the buffer for PBS was carried out with the aid of PD-10 columns. Thereafter 20 μl portions were analysed by means of LDS-PAGE. The results are presented in (FIGS. 14 B and C). The results presented in FIG. 14 show the successful purification of the VHH-Fc fusion protein by means of protein A affinity chromatography from the supernatants of APO-E and APO-B expression cultures. Analysis of the purified protein by means of LDS-PAGE showed a sufficient purity (FIGS. 14 B and C). In the chromatogram (FIG. 14 A) an increase in the absorption during application of the sample was detectable in both samples. For APO-E a maximum absorption was detected at of 113.1 mAu and for APO-B of 42.2 mAu. The absorption rose in the case of the APO-E supernatant to a value almost twice as high as was achieved in the APO-B supernatant. During application of the sample VHH-Fc protein was detected in the breakthrough by means of western blot analysis neither with APO-E (FIG. 15 lane 4) nor with the APO-B sample (data not shown). It was therefore possible to assume a complete binding of the VHH-Fc protein to the column. During the elution of the protein from the column a clearly demarcated peak was detected in both samples, extending over 7 ml (APO-E) and 17 ml (APO-B) Analysis of the fractions of the buffer exchange was carried out by means of LDS-PAGE. By visual comparison of the signal strengths of APO-E and APO-B (cf. FIGS. 12 B and C) it was possible to confirm a significantly larger amount of protein in the fractions of APO-E compared with APO-B. The protein concentration at a wavelength of 280 nm incorporating the molecular weight and the extinction coefficient was determined in the combined fractions by means of NanoDrop. Finally, 0.34 mg of the VHH-Fc fusion protein were isolated from a 200 ml APO-E expression culture and 0.1 mg from a 200 ml APO-B expression culture by means of protein A affinity chromatography. The analysis of the functionality of the protein expressed by APO-E is presented in the following.

Example 6: Functionality Analysis of VHH-Fc Fusion Proteins Produced by Yeast

After the purification of the VHH-Fc fusion protein from the supernatant of the APO-E culture, the functionality of the protein was checked. Since it is known from the literature that *S. cerevisiae* hyperglycosylates certain peptide sequences[141] and this can have an influence on the stability, secretion and biochemical properties of the protein, the binding properties of the VHH-Fc protein to the antigen hsEGFR were investigated experimentally. For this purpose kinetic measurements of the hsEGFR interaction were performed by means of biolayer interferometry using protein A biosensors. In advance of the experiment it was known that the VHH domain had a high specificity and affinity for the antigen hsEGFR. For this purpose the purified VHH-Fc fusion protein was immobilised on the surface of protein A biosensors (FIG. 16 A, step 1). The protein purified beforehand by means of protein A affinity chromatography was used for this. In a further batch the culture supernatant of a VHH-Fc expression culture was used to load the protein A biosensors. After a washing step (FIG. 16 A, step 2) measurement of the base line in PBS was carried out (FIG. 16 A, step 3). If the culture supernatant was used two washing steps were carried out (FIG. 16 B, step 2 and 3) since this contained PEG8000. Association with the soluble antigen hsEGFR in PBS (250 nM, 125 nM, 62.5 nM and 15.6 nM) was then carried out (FIG. 16 A, step 4; FIG. 16 B step 5). The dissociation of VHH-Fc fusion protein and hsEGFR was carried out in PBS (FIG. 16 A, step 5; FIG. 16 B step 6). The binding of the hsEGFR-specific VHH domains to mmEGFR and hs-cMet, for which the VHH domain had no specificity, was analysed as a control. In this case no biomolecular interaction with the antigens mmEGFR and hs-cMet was expected. The results of the measurements are shown in FIG. 16. A successful loading of the protein A biosensors was possible both with the purified protein and with the protein-containing culture supernatant. The loading was to be detected by a continuous increase in the signal in the first 600 seconds (FIGS. 16 A and B, step 1). Since it was possible to employ the purified protein for loading the biosensors in a very much higher concentration than the protein present in the culture supernatant, the sensor signals rose in this case with a significantly greater increase and it was possible for the sensors to be loaded to a greater degree. A layer thickness of from 3.1 to 3.5 nm was achieved. Loading of the sensors with culture supernatant achieved a smaller layer thickness of on average 0.2 nm (FIG. 16 B). The horizontal course of the sensor signals during the subsequent washing steps indicates a stable loading (FIG. 16 A step 2 to 3 B step 2 to 4). A clear jump in the signals between loading and the first washing step is to be seen In FIG. 16 B. This finding is to be attributed to the change In buffer caused by immersing the sensors from the culture medium (+PEG8000) in PBS. This jump was not to be seen in FIG. 16 A since the protein for the loading was already present as a solution in PBS. The association of soluble hsEGFR on the sensors loaded with VHH-Fc is shown in step 4 (FIG. 16 A) and step 5 (FIG. 16 B). During the association a significant increase in the sensor signals occurred in both cases. This increase represented the specific binding of hsEGFR to the sensor surface loaded with VHH-Fc. For analysis of the kinetic constants of the interaction between VHH-Fc and hsEGFR, statistical fitting of the experimental data was performed (FIG. 17). The kinetic constants are given in Tab. 4.1.

TABLE 4.1

Kinetic constants of the binding between VHH-Fc and hsEGFR.

| | $k_a$ (1/Ms) | $k_a$ error | $k_d$ (1/s) | $k_d$ error | $K_D$ (M) |
|---|---|---|---|---|---|
| PBS | $1.06 \times 10^5$ | $8.13 \times 10^2$ | $9.47 \times 10^{-4}$ | $4.56 \times 10^{-6}$ | $8.91 \times 10^{-9}$ |
| Supernatant | $1.55 \times 10^5$ | $1.12 \times 10^3$ | $1.86 \times 10^{-3}$ | $8.03 \times 10^{-6}$ | $1.20 \times 10^{-8}$ |

FIG. 17 showed in both cases a specific, concentration-dependent interaction between immobilised VHH-Fc on the sensor surface and hsEGFR. No interaction occurred between VHH-Fc and the control proteins mmEGFR and cMet. Analysis of the binding of VHH-Fc and hsEGFR by means of biolayer interferometry clearly showed the affinity of the VHH domain for the antigen. The association between the VHH domain and hsEGFR is characterised in FIG. 17 by the characteristic rise in the coloured curves. The dissociation of hsEGFR took place thereafter in PBS and was demonstrated by the continuous slow drop in the coloured curves. The equilibrium dissociation constant ($K_D$) of the protein-protein interaction was calculated by the analysis of association and dissociation. Using purified protein a $K_D$ value of $0.9 \times 10^{-8}$ M was measured (FIG. 17 A). Using culture supernatant resulted in a $K_D$ value of $1.2 \times 10^{-8}$ M (FIG. 17 B). In a measurement of the VHH-Fc protein from the medium supernatant of an HEK293 expression culture carried out beforehand, a $K_D$ value of $8.4 \times 10^{-8}$ M was determined. The protein expressed by HEK293 was an N-terminal Fc fusion of the hsEGFR-specific VHH domain.

Example 7: Glycosylation of the VHH-Fc Protein

The analysis of the glycosylation of the protein secreted by yeast was carried out by means of LDS-PAGE and prior incubation of the protein with the enzyme endoglycosidase H (EndoH). EndoH cleaves specifically mannose-rich oligosaccharides of the N-glycosylation of proteins. It is known from the literature that heterologous expression in yeast cells leads to N-glycosylation with a high number of terminal mannose residues[141]. This so-called hypermannosylation can have an influence on secretion, solubility and folding of the protein[142]. 2 μg of the protein secreted from the yeast were incubated with EndoH and the molecular weight and the flow properties of the protein in polyacrylamide gel were analysed by means of LDS-PAGE. As a control 2 μg of the proteins hsEGFR and thioredoxin were additionally likewise incubated with EndoH and analysed. The results are shown in FIG. 18. By the incubation with EndoH and the subsequent analysis by means of LDS-PAGE it was not possible to confirm any difference in the flow properties of the treated VHH-Fc fusion protein (FIG. 18 lane 1 and 2). By incubation of hsEGFR with EndoH a reduction in the molecular weight was confirmed from different flow properties of the protein in polyacrylamide gel (lane 3 and 4). Due to the absence of glycosylation, thioredoxin showed no change in molecular weight (lane 5 and 6). This indicated that no detectable hypermannosylation of the secreted VHH-Fc protein was present. In the results presented so far, the soluble secretion of VHH-Fc fusion proteins was demonstrated. It was possible to demonstrate that chromosomal overexpression of the oxidoreductase PDI was achieved by genetic manipulation of the strain EBY100. By integration of the PDI expression cassette into the genome of EBY100 the S. cerevisiae strain APO-E was generated. Using this expression strain, it was possible to produce an amount of the VHH-Fc fusion protein sufficient for biochemical analyses. It was furthermore found that the VHH-Fc fusion protein produced by APO-E showed the expected specificity and affinity for the antigen hsEGFR. By comparison of the equilibrium dissociation constants of the protein produced by the yeast and the protein produced by HEK293 comparable values were determined, which indicated a reproducible functionality of the protein produced by the yeast. However, since the aspect of soluble VHH-Fc production represents only a part of the switchable non-covalent method for surface display presented here, the results of surface display of the Fc binding domain and of VHH-Fc fusion proteins and IgG molecules are demonstrated in the following examples.

Example 8: Surface Display of the Fc Binding Domain

The surface display of VHH-Fc fusion proteins was mediated by the co-expression of an Fc binding domain. For surface display on yeast cells this was expressed as a fusion protein with the cell wall protein Aga2p intrinsic to the yeast and in this way served as a direct mediator of the surface display of VHH-Fc fusion proteins. For this purpose the Fc binding domain was cloned into the vector for surface display of proteins on yeast cells pYD1 (Invitrogen) which was commercially obtainable at the start of the experimental work. Two different variants of the Fc binding domain were produced and were compared with one another with respect to their expression properties and their functionality. In this connection the functionality relates to the binding capacity of the domains for Fc parts of human IgG molecules. For this, the Z domain[67] was expressed in a monovalent and in a divalent form as an Aga2p fusion and exposed on the surface of EBY100 cells. The Z domain is derived from S. aureus protein A, binds the Fc part of diverse IgG subtypes[143] and consists of an α-helical structure[69]. The ZZ domain is a duplication of the sequence of the Z domain. In the literature the divalent ZZ domain is attributed a significantly higher affinity for Fc parts of human IgG molecules than the monovalent Z domain. This higher affinity is mostly realised by a significantly lower $K_{off}$[144]. For illustration the kinetic constants of the biomolecular interaction of Fc with the Z and ZZ domain determined in 1995 by Jendeberg and colleagues by means of plasmon resonance detection (BIAcore™) are listed in the following table (Tab. 4.2)[144].

TABLE 4.2

Kinetic constants of the interaction of the Fc binding domains with IgG-Fc.

| Fc binding domain | $k_{on}$ (M/s × $10^{-5}$) | $k_{off}$ (M/s × $10^3$) |
|---|---|---|
| Z domain (monovalent) | 1.9 ± 0.6 | 3.2 ± 1 |
| ZZ domain (divalent) | 3.5 ± 1.0 | 0.51 ± 0.2 |

Example 9: Cloning Strategy of the Fc Binding Domain

For construction of the plasmids for surface display of the two variants of the Fc binding domain the amino acid sequence of the Z domain was ascertained by means of a literature search[67] and the corresponding DNA sequence was cloned in the vector pYD1 in the reading frame of Aga2p. The flexible GS linker contained in the pYD1 vector was obtained between Aga2p and the Fc binding domain. For construction of the ZZ domain the sequence of the Z domain was cloned twice in succession C-terminally into the reading frame of Aga2p. In addition the sequence of the ZZ domain was synthesized (Geneart AG) and cloned into the vector pYD1 (Geneart AG). The Z domain was amplified from a pET13-based plasmid provided in-house and cloned into the vector pYD1 by means of conventional cloning techniques by restriction of DNA and ligation of DNA fragments via the BamHI and NheI cleavage sites. The two vectors (pYD-Z and pYD-ZZ) were generated without the affinity epitope contained in the pYD1 vector (FIG. 19), so that the Z and ZZ domain were anchored on the cell surface with the cell wall protein Aga2p without further modifications and only via a GS linker.

Example 10: Surface Display of the Fc Binding Domain

In order to check which variant of the Fc binding domain was most suitable for the non-covalent surface display of Fc fusion proteins EBY100 cells were transformed on the one hand the with plasmid pYD-Z and on the other hand with the plasmid pYD-ZZ. As a control EBY100 cells were transformed with the plasmid pYD1 (Invitrogen). The receptor α-agglutinin from *S. cerevisiae* was used as a membrane anchor for the surface display of the Fc binding domain. This surface receptor on yeast cells is divided into two proteins Aga1p and Aga2p which are linked via disulphide bridges, and in this way ensures covalent anchoring of the Fc binding domain on the cell surface. The method of surface display on yeast cells established by Boder and Wittrup was used here[92]. Aga1p is coded chromosomally in the genome of EBY100 for this purpose and, like the episomally coded Aga2p, is under the control of the galactose-inducible Gal1 promoter. The expression of AGA1 (Aga1p) and AGA2 (Aga2p) is initiated in the presence of galactose. In the present work the AGA2 expression took place as a fusion with the Z or ZZ domain (FIG. 20). The expression of the surface display was carried out at 20° C. for 72 hours. After determination of the cell density $1 \times 10^7$ cells were removed and the variants of the Fc binding domain on the cell surface were marked. Marking was carried out by binding an FITC-conjugated protein A-specific antibody from the goat. On the basis of its species origin, this antibody was not bound via its Fc part[145]. Instead, binding took place via epitopes on the Fc binding domains which were recognised by the antibody. The cells prepared in this way were then analysed by means of flow cytometry in a Guava easyCyte HT 2 L flow cytometer. The percentage content of cell which the Fc binding domain displayed was determined via the definition of a marker region M1. The marker region was chosen such that as few cells as possible of the negative control (FIG. 21, Aga2p) were located within this region. The negative control was EBY100 transformants which displayed only the anchor protein Aga2p. The histograms of the measurements are shown in FIG. 21. As can be seen in FIGS. 19 A and B, it was possible for both the Z and the ZZ domain to be marked with the protein A-specific antibody over a period of 72 hours and to be detected by flow cytometry. By the expression as Aga2p fusion proteins they were displayed on the cell surface via the interaction of Aga1p and Aga2p. After 24 hours both variants already showed a strong rel. fluorescence signal compared with the negative control (Aga2p). Cells which displayed the divalent ZZ domain showed a signal which was almost twice as strong as cells with the monovalent Z domain (cf. 370.7 and 636.3). This finding is to be explained by the presence of twice the number of specific epitopes due to the sequence duplication. This state of affairs still manifested itself even after 72 hours, the signal strengths of both variants having decreased by approx. 30% at this point in time (cf. 253.0 and 445.1). For both variants in each case two cell populations of different size with different relative signal intensities were detected. The smaller cell populations showed a signal intensity which corresponded to the negative control (Aga2p). The signals of the larger cell populations had significantly higher intensities. As a result it was possible to distinguish them clearly from the negative control. It was concluded from this that the cells located within M1 displayed the Fc binding domain on their surface and in this way were able to be marked specifically. To visualise the surface display of the ZZ domain fluorescence microscopy photographs were produced. For this purpose $1 \times 10^7$ EBY100 cells (pYD-ZZ transformants), after a cultivation period of 48 hours in galactose-containing SD medium, were marked with a protein A-specific antibody (FITC conjugate) from the goat. EBY100 cells which were transformed with the plasmid pYD1 (Invitrogen) and which were likewise incubated with the protein A-specific antibody (FITC conjugate) from the goat served as a control (FIG. 22 C). In the fluorescence microscopy analysis only cells which displayed the ZZ domain on their surface showed a positive fluorescence signal. The photographic presentation of the microscopy photographs is shown in FIG. 22.

The fluorescence microscopy photograph (FIG. 22 B) shows, in comparison with the negative control (FIG. 22 C), that the surface-displayed ZZ domain was marked specifically with the FITC-conjugated antibody. In comparison with the transmitted light photograph (FIG. 22) it was found that it was not possible for all of the cells of the sample to be marked. This finding confirmed again the FACS histograms shown in FIG. 21, which showed that in each expression culture a separate cell population was detected which had the relative fluorescence intensity of the negative control and which therefore for reasons unknown did not display the ZZ domain. In addition to the marking with the protein A-specific detection antibody, the surface display of both variants was investigated experimentally on a functional basis. This is understood as meaning binding of an IgG molecule. With this experiment the variant which was most suitable for the non-covalent surface display of VHH-Fc fusion proteins was identified, since within the non-covalent method the solubly secreted VHH-Fc fusion proteins should be captured by the Fc binding domain anchored on the cell wall. The two variants were marked with the antibody cetuximab (1 µM), which was bound via the Fc content of the Z or ZZ domain. The fluorescence marking was then carried out via the interaction of cetuximab with the biotinylated antigen hsEGFR (1 µM) and the conjugate SA-PE (streptavidin R-phycoerythrin. Detection of the fluorescence-marked cells was carried out by means of flow cytometry in a Guava easycCyte HT. The results of this are shown in FIG. 23. In principle both the Z and the ZZ domain were detectable via the binding of cetuximab (Erbitux). It was concluded from this that both the Z and the ZZ domain were displayed functionally on the surface of EBY100 cells. In the FACS histogram (FIG. 23) it was possible to make a distinction again between two cell populations of different fluorescence intensity. The smaller population (Aga2p-Z: 31.4%, Aga2p-ZZ: 39.3%) showed a weaker signal which corresponded to that of the negative control (FIG. 23, Aga2p). The larger population (Aga2p-Z: 68.6%, Aga2p-ZZ: 60.7%) showed a significantly stronger signal. This is presumably the cells which displayed Aga2p-Z and Aga2p-ZZ on the surface and which were marked specifically via the binding of cetuximab. It was not possible to increase the percentage content of cells in M1 by employing a larger amount of cetuximab (data not shown). In this respect complete saturation of the Fc binding domains with cetuximab existed. As already above, it was also made visible by the binding of an IgG molecule that the divalent ZZ domain showed a significantly stronger relative fluorescence signal than the monovalent Z domain under the same conditions.

In conclusion it can be said that the surface-displayed divalent ZZ domain was marked to a significantly greater extent with the protein A-specific antibody and with the antibody cetuximab than the monovalent Z domain. The ZZ domain accordingly was chosen as the Fc binding domain for all the further experiments. The next sections are concerned with the results of the experimental investigation into the non-covalent surface display of VHH-Fc fusion proteins and IgG molecules.

Example 11: Surface Display of VHH-Fc Fusion Proteins

The successful presentation of the ZZ domain on EBY100 cells was demonstrated in the preceding examples. This additionally showed an adequate functionality with respect to the binding of human IgG molecules. By using the strain APO-E it was shown that it was possible to produce VHH-Fc fusion proteins on a sufficient scale for purification and characterisation of the protein. By using the medium additive PEG8000 it was likewise shown that compared with secretion with the medium additive PEG8000 the secretion of VHH-Fc fusion proteins was increased significantly. The following examples present the results of the surface display of VHH-Fc fusion protein mediated by the ZZ domain on EBY100 cells and the experimental analysis of the genotype-phenotype coupling. These results show the successful bringing together of the soluble secretion of the VHH-Fc fusion protein and the display of the ZZ domain to give the non-covalent method of surface display of antibodies on yeast cells. For the surface display of VHH-Fc fusion proteins electrocompetent EBY100 cells were transformed with the plasmids pYD-ZZ (display of the Fc binding domain) and pYD-pGal1-app8-VHH1-Fc (secretion of the VHH-Fc fusion protein). Simultaneous expression of the two constructs was induced via the cultivation of the cells in galactose-containing medium. For analysis of the influence of PEG8000 on the surface display of the VHH-Fc protein various expression cultures were prepared which differed in their PEG8000 content (without PEG8000 (−PEG), 11% (w/v) (+PEG)). The cultivation of the cells was carried out as described above. Thereafter the cells were analysed by means of fluorescence marking and flow cytometry in a Guava easyCyte HT 2 L. Marking of the VHH domain on the cell was carried out via the specific interaction with the biotinylated antigen hsEGFR (1 µM) and SA-PE (FIGS. 24 A and B). Marking of the ZZ domain on the cell was carried out with a protein A-specific FITC-conjugated antibody from the goat (FIG. 24 C).

FIG. 24 shows that it was possible for the VHH-Fc fusion protein to be marked on the surface of EBY100 cells by the interaction with the biotinylated antigen hsEGFR. This finding applied both to cells which were cultivated in medium without PEG8000 (−PEG) and to cells which were cultivated in medium with PEG8000 (+PEG). One difference between the samples of the two cultures consisted of the intensity of the average relative fluorescence signal detected for the marked VHH domains. This difference was to be seen most clearly after 24 hours (FIG. 24, A: −PEG: 26.9; +PEG: 231.6). At this point in time it was possible to mark more than three times as many cells within the +PEG cells than within the −PEG cells analysed (FIG. 24 A). After a further 48 hours both the fluorescence intensities and the percentage content of VHH-Fc-displaying cells with +PEG and −PEG became closer. After 7 hours 60.8% of the −PEG cells and 66.8% of the +PEG cells displayed the VHH-Fc fusion protein on their surface FIG. 24 B). For closer investigation of the finding that after 24 hours only 20.3% of the −PEG cells displayed the VHH-Fc protein the cells from FIG. 24 A were also marked with the protein A-specific antibody-FITC conjugate from the goat in addition to the marking with hsEGFR. It was presumed that the surface display of the VHH-Fc fusion protein which is suboptimum compared with the +PEG cells is to be attributed to a similarly suboptimum surface display of the ZZ domain. This assumption was refuted by the marking with a protein A-specific antibody. After 24 hours the ZZ domain was displayed sufficiently both on the surface of +PEG cells and of −PEG cells (FIG. 24 C). The lower VHH-Fc signal in FIG. 24 A accordingly was not to be attributed to an inadequate surface display of the ZZ domain for capture of the VHH-Fc fusion proteins. This experiment showed the possibility of successful non-covalent surface display of VHH-Fc fusion proteins by the interaction with the ZZ domain and illustrated the positive effect of PEG8000 in the culture medium on the display of VHH-Fc fusion proteins. For this reason for all the following experiments exclusively PEG8000-containing medium was used for the non-covalent surface display of VHH-Fc fusion proteins. To visualise the surface display of the VHH-Fc fusion protein fluorescence microscopy photographs of the +PEG cells were produced. For this purpose EBY100 cells were transformed with the plasmids pYD-ZZ (surface display of the ZZ domain) and pYD-pGal1-app8-VHH1-Fc (soluble secretion of the VHH-Fc protein). The gene expression was carried out under the conventional conditions for 48 hours. Thereafter $1 \times 10^7$ cells were marked sequentially with 1 µM b-hsEGFR, SA-PE and an Fc-specific F(ab')$_2$ fragment (AlexaFluor™ 647 conjugate). As a control the cells were marked with biotinylated rFcRn (*Rattus norvegicus*) (b-rFcRn), for which the VHH domain showed no specificity. The marking of the surface-displayed VHH-Fc fusion proteins on the yeast cell mediated by the Aga2p-fused ZZ domain is visible by the interaction with b-hsEGFR and SA-PE. These cells appear yellowish in the photograph of the fluorescence microscopy analysis (FIG. 25, column PE). In addition the surface display was detected via the binding of an Fc-specific F(ab')$_2$ AlexaFluor™ 647 conjugate. These cells appear reddish in the photograph of the fluorescence microscopy analysis and represent the marking of the Fc part of the fusion protein (FIG. 25, column: Alexa 647). The overlapping of the two fluorescence signals demonstrated the presence of the VHH-Fc fusion protein and the functionality thereof mediated by the specific binding of the antigen. These cells are shown orange in the fluorescence microscopy photograph. (FIG. 25, column: PE+Alexa 647). A summary of the photographic presentation is shown in the following FIG. 25. From the results shown in FIG. 25 it becomes clear that the VHH-Fc fusion proteins, mediated by the ZZ domain, were successfully displayed on the surface of EBY100 cells. It was possible to detect the specificity of the VHH domains by the binding to b-hsEGFR. No fluorescence signal of the cells was detected for the binding to b-rFcRn. This supports the results of the FACS analyses shown in FIG. 24 and demonstrates that the displayed VHH domains as an Fc fusion on the surface of yeast cells retain their functionality. In order to demonstrate the diversity of the method for non-covalent surface display on yeast cells, in a further experiment the surface display of whole IgG molecules was investigated. The display of IgG molecules requires the functional assembling of four protein chains and the correct formation of disulphide bridges within the individual protein chains and with one another.

Example 12: Surface Display of IgG Molecules

Up to this point it was possible for VHH-Fc fusion proteins to be successfully displayed on the surface of EBY100 cells via the interaction with the ZZ domain. This resulted in the question of whether it was also possible to display more complex molecules, such as whole IgG molecules, via the ZZ domain. It was presumed in advance that the assembling of the light and heavy IgG chain could lead to a poorer surface display of the antibody compared with VHH-Fc fusion proteins, since the surface display of VHH-Fc fusion proteins requires only the assembling of two identical protein chains. For analysis of the surface display of IgG molecules electrocompetent EBY100 cells were transformed with the plasmids pYD-gGal1-app8-HC, pYD-gGal1-app8-LC and pYD-ZZ-G418 and selected on suitable selective agar plates. Since the S. cerevisiae strain EBY100 had only two free auxotrophic markers (Trp/Leu) for the transformation, selection of the plasmid pYD-ZZ-G418 took place via the resistance marker G418. For this purpose the auxotrophic marker of the plasmid was substituted by means of homologous recombination with the resistance cassette kanMX4. For this the kanMX4 cassette from the plasmid pFA6a-kanMX4 (Biochemie, TU Darmstadt, AK Prof. Kolmar) was amplified with the oligodeoxyribonucleotides GR-kanMX4-up and GR-kanMX4-rp and cloned into the vector pYD-ZZ linearised by means of Bsu361. The sequence regions of the Fab fragment coded for the hsEGFR-specific antibody matuzumab (Merck Serono); the sequence coding for the Fc part was adopted from the antibody cetuximab. In the Fc part the amino acid asparagine located at position 297 had been mutated to glutamine in order to avoid the hypermannosylation known for the yeast during the N-glycosylation. The heavy and light IgG chain were furthermore secreted via the signal peptide app8. The expression culture comprised a volume of 3 ml and was carried out in suitable galactose-containing SD medium +PEG8000. The expression was carried out for 48 hours in the well of a 6-well plate at 20° C. After 24 and 48 hours the cell density of the culture was determined and 1×10$^7$ cells were removed. Marking of the cells was carried out with biotinylated hsEGFR and SA-PE. Marking of the Fc part was carried out with an Fc-specific F(ab')$_2$ fragment (AlexaFluor™ 647 conjugate) from the goat. The cells prepared in this way were then analysed by flow cytometry in a Guava easyCyte HT 2 L. The results are shown in FIG. 26. As a control the marking was carried out without the specific antigen. The marker region (M1) was defined such that for the measurement of the control no signal were detected within M1 (FIG. 26 C). It can be seen from FIG. 26 that it was possible for the antibody matuzumab (IgG molecule) to be successfully displayed on the surface of EBY100 cells, mediated by the ZZ domain, since it was possible to detect the specificity of the antibody via the binding to the antigen (hsEGFR). Both after 24 hours (FIG. 26 A) and after 48 hours (FIG. 26 B) a significantly stronger relative fluorescence signal (M1) was detected compared with the negative control (FIG. 26 C). After 48 hours the percentage content of IgG-displaying cells had increased by seven percent compared with the 24 hour measurement. It was assumed that the binding of hsEGFR on the cell took place only in the presence of the heavy and light IgG chain, and for this reason a complete surface display of the IgG molecule was assumed. In a further experiment the surface display of the antibody matuzumab was analysed in another set-up. For this purpose electrocompetent cells were transformed with the plasmids pYD-Aga2p-HC and pYD-pGal1-app8-LC and selected on suitable selective agar plates. In this experiment the heavy IgG chain was expressed as an Aga2p fusion, whereas the light chain was secreted solubly with the aid of the app8 signal peptide. From a stationary preculture a 50 ml expression culture was then prepared with galactose-containing SD medium +PEG8000 and the cells were cultivated under the conventional conditions for 72 hours. After 24 and 72 hours 1×10$^7$ cells were marked with 1 µM b-hsEGFR and SA-PE and an Fc-specific F(ab')$_2$ fragment AlexaFluor™ 647 and investigated by flow cytometry in a Guava easyCyte HT 2 L flow cytometer. The results of this are shown in FIG. 27. The FACS analysis (FIG. 27) of the cells showed that it was indeed possible for the Fc part of the IgG molecule to be detected specifically (rel. fluorescence red), but not the binding of biotinylated antigen hsEGFR (rel. fluorescence yellow). It was to be concluded from this that the IgG molecule was displayed non-functionally on the surface. It was indeed possible to detect an approx. 28% larger cell population with the Fc-specific antibody after 72 hours compared with 24 hours, but in spite of everything it was not possible to detect specific antigen binding even by a prolonged expression period. Compared with the ZZ-mediated display, the surface display of matuzumab in this set-up as a covalent Aga2p fusion of the heavy chain was not successful.

Example 13: Stability Analysis of the VHH-Fc:ZZ Interaction

To analyse the stability of the non-covalent surface display of VHH-Fc fusion proteins by the interaction with the ZZ domain the surface display of VHH-Fc fusion proteins was investigated by flow cytometry over a period of 32 hours. For this purpose electrocompetent EBY100 cells were transformed with the plasmids pYD-ZZ and pYD-pGal1-app8-VHH1-Fc and selected on selective agar plates.

The expression of the surface display of the VHH-Fc fusion protein was carried out for 48 hours. After conclusion of the expression and determination of the cell density of the culture $2\times10^7$ cells were removed and resuspended in 200 µl of PBS and 100 µl of the cell suspension were transferred into a separate reaction vessel. The two samples were pelleted and resuspended in 20 µl of PBS. One sample was marked with b-hsEGFR (1 µM) and SA-PE. The other sample was not marked. The two samples were analysed by flow cytometry (FIG. 28 A) and then mixed in equal parts. The cell mixture was topped up to 1 ml with PBS and stored at 4° C. in the dark for 32 hours. Cells were taken from the mixture at defined points in time (FIG. 29) and investigated by flow cytometry and the average relative fluorescence was determined. Directly after the mixing of the cells a measurement was likewise carried out in order to determine the initial average relative fluorescence intensity of the mixture (FIG. 28 B). This average relative fluorescence intensity was defined hypothetically as the 100% value. The FACS histograms of the samples before mixing, mixed 1:1 and after 32 hours are shown in FIG. 28. The fluorescence signals of the fluorescence-marked EBY100 cells (red) and the non-marked (black) EBY100 cells are shown in FIG. 28 A. The two samples showed clearly different average relative fluorescence intensities (black: 23.9, red: 260,3). The marked sample (FIG. 28 A, red) showed a content of 30.1% of cells which corresponded to the relative fluorescence signal of the non-marked sample. These cells were not located within the marker region M1 and did not display the VHH-Fc protein. The percentage content of these cells was increased by mixing the two samples (FIG. 28 B). 56.4% of the cells here showed a relative fluorescence intensity corresponding to the non-marked sample (FIG. 28 A, black). After storage of the mixture for 32 hours at 4° C. and with exclusion of light the percentage ratios remained approximately the same, although the peak forms in the FACS histogram have changed. Compared with the initial measurement (FIG. 28 B) the peaks are less clearly demarcated from one another (FIG. 28 C). In FIG. 29 the average relative fluorescence intensities measured at the defined points in time are plotted against the time. It becomes clear from FIG. 29 that the average rel. fluorescence of the mixture decreases over the period analysed. At the initial point in time of the mixing the average relative fluorescence intensity was 152.2. After storage at 4° C. in the dark for 32 hours a value of 111.3 was determined. This corresponded to a decrease in the signal strength of 26.9%. This loss was caused either by the dissociation of the VHH-Fc fusion protein from the ZZ domain, the dissociation of the biotinylated antigen hsEGFR from the VHH domain or by the bleaching out of the fluorophore. Since the binding between avidin and biotin is one of the strongest non-covalent bonds[146], however, it was possible to rule this circumstance out, and since the samples were stored with exclusion of light, it was assumed that a bleaching out of the fluorophore was to be disregarded. The decrease in signal strength accordingly was determined chiefly by the dissociation of the VHH-Fc fusion proteins from the ZZ domain and the dissociation of the VHH:hsEGFR complex. It can be said that the stability of the binding between the ZZ domain and the VHH-Fc fusion protein was sufficient for the requirements of the method since it was possible to detect it as stable over a sufficient period of time. For further investigation of the stability of the genotype-phenotype coupling further mixing experiments were carried out.

Example 14: Surface Display of Various VHH-Fc Fusion Proteins

For further experimental investigation of the capacity of the method for non-covalent surface display of VHH-Fc fusion proteins, it was investigated in the following experiment whether it was possible to display three different for hsEGFR-specific VHH domains on yeast cells and whether the signal strengths determined for the antigen binding correlated with $K_D$ values determined beforehand for the biomolecular interaction between VHH and hsEGFR. The determination of equilibrium dissociation constants ($K_D$) of the individual VHH domains was carried out by means of biolayer interferometry. For this purpose the various VHH domains were produced solubly in yeast expression cultures and the particular supernatants of the expression cultures were used for the determination of the $K_D$. A $K_D$ value of 11 nM was measured for the VHH-Fc protein A (VHH-A), a $K_D$ value of 23 nM for VHH-Fc protein B (VHH-B) and a $K_D$ value of 5 nM for the VHH-Fc protein C (VHH-C) (FIG. 30). For production of the various expression vectors the sequence of the VHH domain A (pYD-pGal1-app8-VHH1-Fc) was substituted by means of homologous recombination in each case by the sequences of the VHH domains VHH-B and VHH-C. In addition the domains were amplified using specific oligodexy-ribonucleotides (pYD VHHB up/rp and pYD VHHC up/rp) from pTT5-based expression plasmids made available in-house and cloned into the plasmid pYD-pGal1-app8-VHH1-Fc linearised by means of EcoRI and SacII. The cloning was carried out as explained above. Electrocompetent EBY100 cells were then transformed with the plasmids for soluble secretion of the various VHH-Fc fusion proteins (pYD-pGal1-app8-VHH1-Fc, pYD-pGal1-app8-VHHB-Fc and pYD-pGal1-app8-VHHC-Fc) and the plasmid for the ZZ domain, and three separate expression cultures were prepared. The expression was carried out under the conventional conditions for 48 hours. Thereafter $1\times10^7$ cells of each culture were removed and marked with various concentrations of b-hsEGFR. For this b-hsEGFR was used for marking the cells in the concentrations 200 nM, 150 nM, 100 nM, 20 nM, 10 nM, 1 nM and 0.1 nM. In addition the cells were marked with SA-PE and an Fc-specific F(ab')$_2$ fragment (AlexaFluor™ 647 conjugate). As negative controls the samples without b-hsEGFR were marked. The samples were then analysed in a Guava easy-Cyte HT 2 L flow cytometer. The results of the measurements of the surface display of the various VHH-Fc fusion proteins which were marked with 100 nM b-hsEGFR and SA-PE are shown by way of example in FIG. 30. For standardisation of the surface display the maker region M1 was defined and the average relative fluorescence intensity of these populations were plotted against the hsEGFR concentrations used. These results are shown in FIG. 31. The biolayer interferometry measurements for determination of the $K_D$ value carried out beforehand are additionally shown in FIG. 30. Tab. 4.3 shows the kinetic constants determined for the VHH:hsEGFR interaction.

TABLE 4.3

Kinetic constants of the binding of the VHH-Fc fusion proteins (A, B, C) to hsEGFR.

| | $k_a$ (1/Ms) | $k_a$ error | $k_d$ (1/s) | $k_d$ error | $K_D$ (M) |
|---|---|---|---|---|---|
| VHH-A | $1.55 \times 10^5$ | $1.02 \times 10^3$ | $1.83 \times 10^{-3}$ | $7.29 \times 10^{-6}$ | $1.18 \times 10^{-8}$ |
| VHH-B | $6.51 \times 10^4$ | $4.62 \times 10^2$ | $1.50 \times 10^{-3}$ | $7.06 \times 10^{-6}$ | $2.31 \times 10^{-8}$ |
| VHH-C | $1.48 \times 10^5$ | $4.18 \times 10^2$ | $6.98 \times 10^{-4}$ | $2.73 \times 10^{-6}$ | $4.74 \times 10^{-9}$ |

The differences in the $K_D$ values of the various VHH domains for the antigen hsEGFR was also reflected in the case of the surface display of the VHH domains as an Fc fusion mediated by the ZZ domain (FIG. 31). In a concentration range of from 200 to 20 nM different average relative fluorescence intensities were to be detected in the surface-displayed proteins. VHH-C showed, marked with the same amount of antigen, a stronger relative fluorescence signal than VHH-A and VHH-B. This finding was to be confirmed by the comparison with the $K_D$ values determined beforehand. This experiment illustrated the capacity of the system since even small $K_D$ differences (5 nM and 11 nM) were reproducible in the FACS analysis.

Example 15: Phenotype-Phenotype Coupling

For experimental investigation of the stability of the genotype-phenotype coupling of the system of non-covalent surface display various mixing experiments were carried out[147]. For this purpose target cells were diluted in a high excess of control cells and these were then concentrated in successive cycles of magnetic (MACS) and fluorescence-activated cell sorting (FACS). The mechanism of concentration was based on the detection of biomolecular interactions. By the mixing of target and control cells a type of model library was generated which reflected a certain diversity due to the high dilution of a specific cell population. Two different mixing experiments were carried out, which are explained in the following. For preparation of the mixtures the cell counts were calculated under the assumption that the optical density ($\lambda_{600}$) of a yeast culture of 1 corresponded to $=1 \times 10^7$ cells[137]. It can be said that the results of the two mixing experiments delivered strong evidence that the interaction between the ZZ domain and VHH-Fc fusion protein was stable enough to concentrate and to isolate target cells from a large excess of control cells by means of the usual HTS methods, such as MACS and FACS, due to the specific binding property of the displayed VHH domain.

Example 16: Changing Between Surface Display and Soluble Secretion

With the aid of the method for non-covalent surface display selected proteins can be produced in a soluble form for further characterisation. This is possible with the method presented here without time-consuming intermediate steps, in contrast to the conventional methods. In comparable methods for surface display, such as e.g. using the covalent surface display on yeast cells as an Aga2p fusion, it was hitherto necessary to reclone the selected clones into a suitable vector for soluble production of the protein. The method presented here delivers a decisive innovation, in that the VHH-Fc fusion proteins are displayed in a non-covalent manner via the interaction with the ZZ domain. Nevertheless, the need to use two vectors is inherent to the method: one vector for expression and covalent surface anchoring of the ZZ domain via Aga2p, a second for soluble secretion of the VHH-Fc fusion protein. In order to bypass the isolation of the plasmid for the soluble secretion of the VHH-Fc fusion protein by means of plasmid isolation and renewed transformation of yeast cells. a further plasmid was produced for switchable expression and soluble secretion of the VHH-Fc fusion protein into the culture supernatant. For this purpose the inducible Gal1 promoter in the plasmid pYD-pGal-app8-VHH1-Fc was replaced by the constitutively expressing promoter GAPDH by means of homologous recombination in yeast cells. The DNA sequence of the GAPDH promoter was amplified with the oligodeoxyribonucleotides gapdh-pYD-up and gapdh-pYD-rp and the plasmid pGAPZ (Life Technologies Corp.) by means of PCR. By using the abovementioned oligodeoxribonucleotides a PCR product was generated which had on its ends sequence region homologous to the plasmid pYD-pGal-app8-VHH1-Fc. To initiate the homologous recombination in yeast cells the plasmid was linearised with the restriction endonuclease KpnI. The restriction was checked by means of agarose gel electrophoresis (data not shown) The recognition sequence for KpnI was inserted in advance in the region of the DNA sequence of the Gal1 promoter in the plasmid pYD-pGal-app8-VHH1-Fc by means of site-specific mutagenesis. For this the oligodeoxyribonucleotides pGal-KpnI-up and pGal-KpnI-rp were used. The mutagenesis was checked and confirmed by means of sequencing with flanking oligodeoxyribonucleotides (pYD pex up/rp). For the homologous recombination in yeast cells the plasmid linearised by means of KpnI and the PCR product for the sequence of the GAPDH promoter were used for transformation of EBY100 cells. After selection, E. coli transformation, plasmid isolation and subsequent sequencing the clone with the desired plasmid sequence was identified. The plasmid pYD-pGAPDH-app8-VHH1-Fc with successful promoter substitution was then used with the plasmid pYD-ZZ for transformation of electrocompetent EBY100 cells. The switchable expression is achieved in these double transformants via the transfer of the cells from galactose-containing SD medium into glucose-containing SD medium, as a result of which repression of the Gal1 promoter takes place and the ZZ domain is no longer expressed. For a control, the plasmid pYD-pGal-app8-VHH1-Fc was used with the plasmid pYD-ZZ likewise for transformation of EBY100 cells. The soluble VHH-Fc secretion is regulated by the Gal1 promoter, like the surface display of the ZZ domain, as a result of which soluble secretion of the VHH-Fc fusion proteins is not possible via the transfer of the cells into the glucose-containing medium. When selection had taken place on suitable selective agar plates, in each case one clone was used for the preparation of a glucose-containing SD culture +PEG8000. After the cultivation cultures were prepared with suitable galactose-containing SD medium +PEG8000. The behaviour of the two promoter pairs (pGal1/pGal1 and pGal1/pGAPDH) with respect to the surface display of the ZZ domains and the VHH-Fc fusion proteins is shown in FIG. 32. For this purpose the cells of the glucose-containing cultures and the cells of the galactose-containing cultures were marked with an Fc-specific F(ab')$_2$ fragment (AlexaFluor™ 647 conjugate) and a protein A-specific antibody (FITC conjugate) and analysed in a Guava easyCyte HT 2 L flow cytometer. By the two-colour marking of the cells with the Fc-specific antibody and the protein A-specific antibody it was possible to detect the surface display of the VHH-Fc fusion protein and of the ZZ domain simultaneously. As a result checking of the modes of functioning of the promoters in the flow cytometer was rendered possible. The uniform behaviour of the two promoter pairs with respect to the surface display of VHH-Fc fusion proteins under various cultivation conditions is illustrated by the FACS histograms shown in FIG. 32. By the cultivation in glucose-containing medium neither the ZZ domain (grey FIGS. 32 A and B), nor the VHH-Fc fusion protein (grey, FIGS. 32 C and D) was displayed on the cell surface. By the cultivation of the cells in galactose-containing medium, using both promoter pairs its was possible to mark both the ZZ domain (red, FIGS. 32 A and B) and the VHH-Fc protein (red, FIGS. 32 C and D) on the cell surface by interaction with the Fc-specific detection antibody and to detect them by flow cytometry.

In the next step the properties of the promoter pair pGAPDH/pGal1 were analysed in more detail. For this purpose the cells of the glucose-containing culture were transferred into galactose-containing medium +PEG8000 for induction of the surface display and cultivated at 20° C. and 250 rpm for 48 hours. The detection of the gene expression of the ZZ domain and VHH-Fc construct was carried out via fluorescence marking of the surface-displayed proteins and analysis of the cells in a flow cytometer. The ZZ domain was marked via a protein A-specific FITC-marked antibody from the goat (rel. fluorescence green), the VHH-Fc fusion protein via an Fc fragment specific $F(ab')_2$ fragment (AlexaFluor™ 647 conjugate) from the goat (rel. fluorescence red). The results of this measurement is shown in FIG. 33 A. Glucose-containing medium was then inoculated with cells from the galactose-containing culture. The cell density used for the preparation of this culture was $0.5 \times 10^7$ cells/ml. The cells were then cultivated at 30° C. and 250 rpm for 48 hours. A renewed transfer of the cells followed. For this purpose fresh glucose-containing medium +PEG8000 was inoculated with an extremely low cell density of the preceding culture. This culture was cultivated at 20° C. and 250 rpm for 48 hours for soluble production of the VHH-Fc fusion protein. The surface display of the ZZ domain and the VHH-Fc fusion protein was then analysed again by means of fluorescence marking (see above) and flow cytometry. The result of this measurement is shown in FIG. 33 B. FIG. 33 illustrates the successful repression of the surface display of the ZZ domain by the transfer of the cells into glucose-containing medium (FIG. 33 B). As a result the surface display of the VHH-Fc fusion proteins was likewise suppressed since it was no longer possible for these to be captured on the cell, but were continued to be secreted. For analysis of the behaviour of the two promoter pairs with respect to soluble secretion of the VHH-Fc fusion protein into the culture supernatant western blot analyses of the culture supernatants were prepared. After determination of the cell density of the glucose- and galactose-containing cultures described above samples of the culture supernatants of a volume corresponding to $1 \times 10^7$ cells were removed and precipitated by means of TCA and were worked up for the LDS-PAGE and western blot analysis. In each case one sample was taken after cultivation in galactose-containing medium (FIG. 34 lane 1 and 2) and in each case one sample after 48 hours of cultivation (FIG. 34 lane 3 and 4) in glucose-containing medium. In addition the glucose-containing cultures were cultivated for a further 48 hours ($\triangleq$ 96 h), since the optimum expression duration of the VHH-Fc fusion protein using the GAPDH promoter was not known and was checked experimentally in this way. A VHH-Fc fusion protein expressed by HEK293 was used as a positive control (FIG. 34 lane 7). The results of the western blot analysis are presented in the following. As can be seen from FIG. 34, it was not possible to detect the VHH-Fc fusion protein in the culture supernatant during the cultivation in galactose-containing medium in the case of both promoter pairs (lane 1 and 2). By the transfer into glucose-containing medium, using the Gal1/GAPDH promoter pair an Fc-specific signal was detectable in the western blot (lane 4) and accordingly the VHH-Fc protein was detectable in the culture supernatant. By the further cultivation it was possible to increase the strength of the signal, and to detect the continuing gene expression and the subsequent accumulation of the proteins in the culture medium (lane 6). It was possible to conclude from this that the longer duration of expression led to an increased VHH-Fc concentration in the culture supernatant. When the Gal1/Gal1 promoter pair was used neither after 48 hours nor after 96 hours was an Fc-specific signal detected in the culture supernatant (FIG. 34 lane 3 and 5) since the expression of the Gal1 promoter was repressed by the glucose present in the medium and the gene expression for the VHH-Fc fusion did not take place. On the basis of these results it was possible to draw the conclusion that by using the Gal1/GAPDH promoter pair it was possible to switch the location of the VHH-Fc fusion protein from surface display to soluble secretion into the culture supernatant by modification of the cultivation conditions.

Example 16: Production of Various VHH Libraries

The use of the non-covalent method for surface display of VHH-Fc fusion proteins was tried out by generation of various VHH libraries and surface display thereof on yeast cells. The VHH libraries were produced using various technologies known in the literature. Libraries having different sequence diversities were thereby generated.

LITERATURE CITED ABOVE AND NON-CITED LITERATURE RELEVANT TO THE INVENTION

1. Swinney, D. C. & Anthony, J. How were new medicines discovered? Nat. Rev. Drug Discov. 10, 507-519 (2011).
2. Venter, J. C. et al. The sequence of the human genome. Science 291, 1304-1351 (2001).
3. Futreal, P. A. et al. BRCA1 mutations in primary breast and ovarian carcinomas. Science 266, 120-122 (1994).
4. Miki, Y. et al. A strong candidate for the breast and ovarian cancer susceptibility gene BRCA1. Science 266, 66-71 (1994).
5. Munos, B. Lessons from 60 years of pharmaceutical innovation. Nat. Rev. Drug Discov. 8, 959-968 (2009).
6. DiMasi, J. A., Hansen, R. W., & Grabowski, H. G. The price of innovation: new estimates of drug development costs. J. Health Econ. 22, 151-185 (2003).
7. Scannell, J. W., Blanckley, A., Boldon, H., & Warrington, B. Diagnosing the decline in pharmaceutical R&D efficiency. Nat. Rev. Drug Discov. 11, 191-200 (2012).
8. Research and Development in the pharmaceutical industry, Study for the Congressional Budget Office, Congress of the United States of America. 2006. Reference type: Online source
9. Beckman, R. A., Weiner, L. M., & Davis, H. M. Antibody constructs in cancer therapy: protein engineering strategies to improve exposure in solid tumors. Cancer 109, 170-179 (2007).
10. Porro, D., Sauer, M., Branduardi, P., & Mattanovich, D. Recombinant protein production in yeasts. Mol. Biotechnol. 31, 245-259 (2005).
11. Sudbery, P. E. The expression of recombinant proteins in yeasts. Curr. Opin. Biotechnol. 7, 517-524 (1996).
12. Benson, J. D. et al. Validating cancer drug targets. Nature 441, 451-456 (2006).
13. Klapper, L. N., Kirschbaum, M. H., Sela, M., & Yarden, Y. Biochemical and clinical implications of the ErbB/HER signaling network of growth factor receptors. Adv. Cancer Res. 77, 25-79 (2000).
14. Huang, S. M. & Harari, P. M. Epidermal growth factor receptor inhibition in cancer therapy: biology, rationale and preliminary clinical results. Invest New Drugs 17, 259-269 (1999).
15. Huang, S. M., Bock, J. M., & Harari, P. M. Epidermal growth factor receptor blockade with C225 modulates proliferation, apoptosis, and radiosensitivity in squamous cell carcinomas of the head and neck. *Cancer Res.* 59, 1935-1940 (1999).
16. Sato, J. D. et al. Biological effects in vitro of monoclonal antibodies to human epidermal growth factor receptors. *Mol. Biol. Med.* 1, 511-529 (1983).
17. Salomon, D. S., Brandt, R., Ciardiello, F., & Normanno, N. Epidermal growth factor-related peptides and their receptors in human malignancies. *Crit Rev. Oncol. Hematol.* 19, 183-232 (1995).
18. Baselga, J. The EGFR as a target for anticancer therapy—focus on cetuximab. *Eur. J. Cancer* 37 Suppl 4, S16-S22 (2001).
19. PhRMA (Pharmaceutical Research and Manufacturers of America. 2012. Reference type: Online source
20. Imai, K. & Takaoka, A. Comparing antibody and small-molecule therapies for cancer. *Nat. Rev. Cancer* 6, 714-727 (2006).
21. Thurber, G. M., Schmidt, M. M., & Wittrup, K. D. Factors determining antibody distribution in tumors. *Trends Pharmacol. Sci.* 29, 57-61 (2008).
22. Roopenian, D. C. & Akilesh, S. FcRn: the neonatal Fc receptor comes of age. *Nat. Rev. Immunol.* 7, 715-725 (2007).
23. Carter, P. J. Potent antibody therapeutics by design. *Nat. Rev. Immunol.* 6, 343-357 (2006).
24. Goldberg, R. M. Cetuximab. *Nat. Rev. Drug Discov. Suppl*, S10-S11 (2005).
25. Baselga, J. Targeting tyrosine kinases in cancer: the second wave. *Science* 312, 1175-1178 (2006).
26. Huang, S., Armstrong, E. A., Benavente, S., Chinnaiyan, P., & Harari, P. M. Dualagent molecular targeting of the epidermal growth factor receptor (EGFR): combining anti-EGFR antibody with tyrosine kinase inhibitor. *Cancer Res.* 64, 5355-5362 (2004).
27. Iannello, A. & Ahmad, A. Role of antibody-dependent cell-mediated cytotoxicity in the efficacy of therapeutic anti-cancer monoclonal antibodies. *Cancer Metastasis Rev.* 24, 487-499 (2005).
28. Nakamura, A., Kubo, T., & Takai, T. Fc receptor targeting in the treatment of allergy, autoimmune diseases and cancer. *Adv. Exp. Med. Biol.* 640, 220-233 (2008).
29. YALOW, R. S. & BERSON, S. A. Assay of plasma insulin in human subjects by immunological methods. *Nature* 184 (Suppl 21), 1648-1649 (1959).
30. van Weemen, B. K. & Schuurs, A. H. Immunoassay using antigen-enzyme conjugates. *FEBS Lett.* 15, 232-236 (1971).
31. Engvall, E. & Perlmann, P. Enzyme-linked immunosorbent assay (ELISA). Quantitative assay of immunoglobulin G. *Immunochemistry.* 8, 871-874 (1971).
32. Murphy, K., Travers, P., & Walport, M. *Janeway's Immunobiology* (Garlan Science, Taylor & Francis Group, LLC, 2008).
33. Filpula, D. Antibody engineering and modification technologies. *Biomol. Eng* 24, 201-215 (2007).
34. Nimmerjahn, F. & Ravetch, J. V. Fcgamma receptors as regulators of immune responses. *Nat. Rev. Immunol.* 8, 34-47 (2008).
35. Idusogie, E. E. et al. Mapping of the C1q binding site on rituxan, a chimeric antibody with a human IgG1 Fc. *J. Immunol.* 164, 4178-4184 (2000).
36. Natsume, A., Niwa, R., & Satoh, M. Improving effector functions of antibodies for cancer treatment: Enhancing ADCC and CDC. *Drug Des Devel. Ther.* 3, 7-16 (2009).
37. Brambell, F. W. The transmission of immunity from mother to young and the catabolism of immunoglobulins. *Lancet* 2, 1087-1093 (1966).
38. Kohler, G. & Milstein, C. Continuous cultures of fused cells secreting antibody of predefined specificity. *Nature* 256, 495-497 (1975).
39. Yuan, F. F., Watt, J. M., & Geczy, A. F. Does hybridoma technology still have a place in transfusion medicine? *Transfus. Med. Rev.* 16, 230-238 (2002).
40. Worn, A. & Pluckthun, A. Stability engineering of antibody single-chain Fv fragments. *J. Mol. Biol.* 305, 989-1010 (2001).
41. Chames, P., Van, R. M., Weiss, E., & Baty, D. Therapeutic antibodies: successes, limitations and hopes for the future. *Br. J. Pharmacol.* 157, 220-233 (2009).
42. Holliger, P. & Hudson, P. J. Engineered antibody fragments and the rise of single domains. *Nat. Biotechnol.* 23, 1126-1136 (2005).
43. Bird, R. E. et al. Single-chain antigen-binding proteins. *Science* 242, 423-426 (1988).
44. Kontermann, R. E. Alternative antibody formats. *Curr. Opin. Mol. Ther.* 12, 176-183 (2010).
45. Wesolowski, J. et al. Single domain antibodies: promising experimental and therapeutic tools in infection and immunity. *Med. Microbiol. Immunol.* 198, 157-174 (2009).
46. Holliger, P., Prospero, T., & Winter, G. "Diabodies": small bivalent and bispecific antibody fragments. *Proc. Natl. Acad. Sci. U.S.A* 90, 6444-6448 (1993).
47. Todorovska, A. et al. Design and application of diabodies, triabodies and tetrabodies for cancer targeting. *J. Immunol. Methods* 248, 47-66 (2001).
48. Hamers-Casterman, C. et al. Naturally occurring antibodies devoid of light chains. *Nature* 363, 446-448 (1993).
49. Muyldermans, S. Single domain camel antibodies: current status. *J. Biotechnol.* 74, 277-302 (2001).
50. De, G. E., Saerens, D., Muyldermans, S., & Conrath, K. Antibody repertoire development in camelids. *Dev. Comp Immunol.* 30, 187-198 (2006).
51. Simmons, D. P. et al. Dimerisation strategies for shark IgNAR single domain antibody fragments. *J. Immunol. Methods* 315, 171-184 (2006).
52. Wu, T. T., Johnson, G., & Kabat, E. A. Length distribution of CDRH3 in antibodies. *Proteins* 16, 1-7 (1993).
53. Harmsen, M. M. & De Haard, H. J. Properties, production, and applications of camelid single-domain antibody fragments. *Appl. Microbiol. Biotechnol.* 77, 13-22 (2007).
54. Muyldermans, S., Atarhouch, T., Saldanha, J., Barbosa, J. A., & Hamers, R. Sequence and structure of VH domain from naturally occurring camel heavy chain immunoglobulins lacking light chains. *Protein Eng* 7, 1129-1135 (1994).
55. Desmyter, A., Decanniere, K., Muyldermans, S., & Wyns, L. Antigen specificity and high affinity binding provided by one single loop of a camel single-domain antibody. *J. Biol. Chem.* 276, 26285-26290 (2001).
56. Chothia, C., Novotny, J., Bruccoleri, R., & Karplus, M. Domain association in immunoglobulin molecules. The packing of variable domains. *J. Mol. Biol.* 186, 651-663 (1985).
57. Desmyter, A. et al. Crystal structure of a camel single-domain VH antibody fragment in complex with lysozyme. *Nat. Struct. Biol.* 3, 803-811 (1996).

58. Braden, B. C. et al. Three-dimensional structures of the free and the antigen-complexed Fab from monoclonal anti-lysozyme antibody D44.1. *J. Mol. Biol.* 243, 767-781 (1994).
59. van der Linden, R. H. et al. Comparison of physical chemical properties of llama VHH antibody fragments and mouse monoclonal antibodies. *Biochim. Biophys. Acta* 1431, 37-46 (1999).
60. Cortez-Retamozo, V. et al. Efficient tumor targeting by single-domain antibody fragments of camels. *Int. J. Cancer* 98, 456-462 (2002).
62. Foster, T. J. Immune evasion by staphylococci. *Nat. Rev. Microbiol.* 3, 948-958 (2005).
63. Moks, T. et al. Staphylococcal protein A consists of five IgG-binding domains. *Eur. J. Biochem.* 156, 637-643 (1986).
64. Jansson, B., Uhlen, M., & Nygren, P. A. All individual domains of staphylococcal protein A show Fab binding. *FEMS Immunol. Med. Microbiol.* 20, 69-78 (1998).
65. Uhlen, M. et al. Complete sequence of the staphylococcal gene encoding protein A. A gene evolved through multiple duplications. *J. Biol. Chem.* 259, 1695-1702 (1984).
66. Akerstrom, B. & Bjorck, L. A physicochemical study of protein G, a molecule with unique immunoglobulin G-binding properties. *J. Biol. Chem.* 261, 10240-10247 (1986).
67. Nilsson, B. et al. A synthetic IgG-binding domain based on staphylococcal protein A. *Protein Eng* 1, 107-113 (1987).
68. Ljungberg, U. K. et al. The interaction between different domains of staphylococcal protein a and human polyclonal IgG, IgA, IgM and F(ab')2: Separation of affinity from specificity. *Molecular Immunology* 30, 1279-1285 (1993).
69. Tashiro, M. et al. High-resolution solution NMR structure of the Z domain of staphylococcal protein A. *J. Mol. Biol.* 272, 573-590 (1997).
70. Jendeberg, L. et al. The mechanism of binding staphylococcal protein A to immunoglobin G does not involve helix unwinding. *Biochemistry* 35, 22-31 (1996).
71. Nilsson, J. et al. Competitive Elution of Protein A Fusion Proteins Allows Specific Recovery Under Mild Conditions. *European Journal of Biochemistry* 224, 103-108 (1994).
72. Kuypers, D. R. & Vanrenterghem, Y. F. Monoclonal antibodies in renal transplantation: old and new. *Nephrol. Dial. Transplant.* 19, 297-300 (2004).
73. Renders, L. & Valerius, T. Engineered CD3 antibodies for immunosuppression. *Clin. Exp. Immunol.* 133, 307-309 (2003).
74. Hansel, T. T., Kropshofer, H., Singer, T., Mitchell, J. A., & George, A. J. The safety and side effects of monoclonal antibodies. *Nat. Rev. Drug Discov.* 9, 325-338 (2010).
75. Riechmann, L., Clark, M., Waldmann, H., & Winter, G. Reshaping human antibodies for therapy. *Nature* 332, 323-327 (1988).
76. Lonberg, N. Human antibodies from transgenic animals. *Nat. Biotechnol.* 23, 1117-1125 (2005).
77. Lonberg, N. Fully human antibodies from transgenic mouse and phage display platforms. *Curr. Opin. Immunol.* 20, 450-459 (2008).
78. Riechmann, L., Clark, M., Waldmann, H., & Winter, G. Reshaping human antibodies for therapy. *Nature* 332, 323-327 (1988).
79. Hoogenboom, H. R. Selecting and screening recombinant antibody libraries. *Nat. Biotechnol.* 23, 1105-1116 (2005).
80. Jung, Y. S. et al. Generation of human monoclonal antibodies against Propioni-bacterium acnes by applying the phage display method to human peripheral blood mononuclear cells immunized in vitro. *Cytotechnology* 57, 169-175 (2008).
81. Kuroda, D., Shirai, H., Kobori, M., & Nakamura, H. Systematic classification of CDR-L3 in antibodies: implications of the light chain subtypes and the VL-VH interface. *Proteins* 75, 139-146 (2009).
82. Al-Lazikani, B., Lesk, A. M., & Chothia, C. Standard conformations for the canonical structures of immunoglobulins. *J. Mol. Biol.* 273, 927-948 (1997).
83. Riechmann, L., Clark, M., Waldmann, H., & Winter, G. Reshaping human antibodies for therapy. *Nature* 332, 323-327 (1988).
84. Arnold, F. H. & Moore, J. C. Optimizing industrial enzymes by directed evolution. *Adv. Biochem. Eng Biotechnol.* 58, 1-14 (1997).
85. Dougherty, M. J. & Arnold, F. H. Directed evolution: new parts and optimized function. *Curr. Opin. Biotechnol.* 20, 486-491 (2009).
86. Kaur, J. & Sharma, R. Directed evolution: an approach to engineer enzymes. *Crit Rev. Biotechnol.* 26, 165-199 (2006).
87. Stemmer, W. P. Rapid evolution of a protein in vitro by DNA shuffling. *Nature* 370, 389-391 (1994).
88. Blagodatski, A. & Katanaev, V. L. Technologies of directed protein evolution in vivo. *Cell Mol. Life Sci.* 68, 1207-1214 (2011).
89. Hanes, J. & Pluckthun, A. In vitro selection and evolution of functional proteins by using ribosome display. *Proc. Natl. Acad. Sci. U.S.A* 94, 4937-4942 (1997).
90. Smith, G. P. Filamentous fusion phage: novel expression vectors that display cloned antigens on the virion surface. *Science* 228, 1315-1317 (1985).
91. Jespers, L. S., Roberts, A., Mahler, S. M., Winter, G., & Hoogenboom, H. R. Guiding the selection of human antibodies from phage display repertoires to a single epitope of an antigen. *Biotechnology (N. Y.)* 12, 899-903 (1994).
92. Boder, E. T. & Wittrup, K. D. Yeast surface display for screening combinatorial polypeptide libraries. *Nat. Biotechnol.* 15, 553-557 (1997).
93. van der Vaart, J. M. et al. Comparison of cell wall proteins of *Saccharomyces cerevisiae* as anchors for cell surface expression of heterologous proteins. *Appl. Environ. Microbiol.* 63, 615-620 (1997).
94. Sato, N. et al. Long anchor using Flo1 protein enhances reactivity of cell surface-displayed glucoamylase to polymer substrates. *Appl. Microbiol. Biotechnol.* 60, 469-474 (2002).
95. Feldhaus, M. J. et al. Flow-cytometric isolation of human antibodies from a non-immune *Saccharomyces cerevisiae* surface display library. *Nat. Biotechnol.* 21, 163-170 (2003).
96. van den Beucken, T. et al. Affinity maturation of Fab antibody fragments by fluorescent-activated cell sorting of yeast-displayed libraries. *FEBS Lett.* 546, 288-294 (2003).
97. Kondo, A. & Ueda, M. Yeast cell-surface display—applications of molecular display. *Appl. Microbiol. Biotechnol.* 64, 28-40 (2004).

98. Huang, G., Zhang, M., & Erdman, S. E. Posttranslational modifications required for cell surface localization and function of the fungal adhesin Aga1p. *Eukaryot. Cell* 2, 1099-1114 (2003).

99. Pepper, L. R., Cho, Y. K., Boder, E. T., & Shusta, E. V. A decade of yeast surface display technology: where are we now? *Comb. Chem. High Throughput. Screen.* 11, 127-134 (2008).

100. Skerra, A. & Pluckthun, A. Assembly of a functional immunoglobulin Fv fragment in *Escherichia coli*. *Science* 240, 1038-1041 (1988).

101. Jost, C. R. et al. Mammalian expression and secretion of functional single-chain Fv molecules. *J. Biol. Chem.* 269, 26267-26273 (1994).

102. Goffeau, A. et al. Life with 6000 genes. *Science* 274, 546, 563-546, 567 (1996).

103. Mortimer, R. K., Contopoulou, C. R., & King, J. S. Genetic and physical maps of *Saccharomyces cerevisiae*, Edition 11. *Yeast* 8, 817-902 (1992).

104. Jeong, K. J., Jang, S. H., & Velmurugan, N. Recombinant antibodies: engineering and production in yeast and bacterial hosts. *Biotechnol. J.* 6, 16-27 (2011).

105. Strausberg, R. L. & Strausberg, S. L. Overview of protein expression in *Saccharomyces cerevisiae*. *Curr. Protoc. Protein Sci. Chapter* 5, Unit 5 (2001).

106. Muller, S., Sandal, T., Kamp-Hansen, P., & Dalboge, H. Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from *Yarrowia lipolytica*. *Yeast* 14, 1267-1283 (1998).

107. Freyre, F. M. et al. Very high expression of an anti-carcinoembryonic antigen single chain Fv antibody fragment in the yeast *Pichia pastoris*. *J. Biotechnol.* 76, 157-163 (2000).

108. Kretzschmar, T. et al. High-level expression in insect cells and purification of secreted monomeric single-chain Fv antibodies. *J. Immunol. Methods* 195, 93-101 (1996).

109. Sanchez, L. et al. High cytoplasmic expression in *E. coli*, purification, and in vitro refolding of a single chain Fv antibody fragment against the hepatitis B surface antigen. *J. Biotechnol.* 72, 13-20 (1999).

110. Horwitz, A. H., Chang, C. P., Better, M., Hellstrom, K. E., & Robinson, R. R. Secretion of functional antibody and Fab fragment from yeast cells. *Proc. Natl. Acad. Sci. U.S.A* 85, 8678-8682 (1988).

111. Rakestraw, J. A., Sazinsky, S. L., Piatesi, A., Antipov, E., & Wittrup, K. D. Directed evolution of a secretory leader for the improved expression of heterologous proteins and full-length antibodies in *Saccharomyces cerevisiae*. *Biotechnol. Bioeng.* 103, 1192-1201 (2009).

112. Machamer, C. E., Doms, R. W., Bole, D. G., Helenius, A., & Rose, J. K. Heavy chain binding protein recognizes incompletely disulfide-bonded forms of vesicular stomatitis virus G protein. *J. Biol. Chem.* 265, 6879-6883 (1990).

113. Nguyen, T. H., Law, D. T., & Williams, D. B. Binding protein BiP is required for translocation of secretory proteins into the endoplasmic reticulum in *Saccharomyces cerevisiae*. *Proc. Natl. Acad. Sci. U.S.A* 88, 1565-1569 (1991).

114. Xu, P. & Robinson, A. S. Decreased secretion and unfolded protein response upregulation are correlated with intracellular retention for single-chain antibody variants produced in yeast. *Biotechnol. Bioeng.* 104, 20-29 (2009).

115. Idiris, A., Tohda, H., Kumagai, H., & Takegawa, K. Engineering of protein secretion in yeast: strategies and impact on protein production. *Appl. Microbiol. Biotechnol.* 86, 403-417 (2010).

116. Knippers, R. *Molekulare Genetik*. 9. komplett überarbeitete Auflage (Thieme Verlag, 2006).

117. Mattanovich, D., Gasser, B., Hohenblum, H., & Sauer, M. Stress in recombinant protein producing yeasts. *J. Biotechnol.* 113, 121-135 (2004).

118. Shusta, E. V., Raines, R. T., Pluckthun, A., & Wittrup, K. D. Increasing the secretory capacity of *Saccharomyces cerevisiae* for production of single-chain antibody fragments. *Nat. Biotechnol.* 16, 773-777 (1998).

119. Cereghino, G. P. & Cregg, J. M. Applications of yeast in biotechnology: protein production and genetic analysis. *Curr. Opin. Biotechnol.* 10, 422-427 (1999).

120. Suga, M. & Hatakeyama, T. High-efficiency electroporation by freezing intact yeast cells with addition of calcium. *Curr. Genet.* 43, 206-211 (2003).

121. Benatuil, L., Perez, J. M., Belk, J., & Hsieh, C. M. An improved yeast transformation method for the generation of very large human antibody libraries. *Protein Eng Des Sel* 23, 155-159 (2010).

122. Orr-Weaver, T. L., Szostak, J. W., & Rothstein, R. J. Yeast transformation: a model system for the study of recombination. *Proc. Natl. Acad. Sci. U.S.A* 78, 6354-6358 (1981).

123. Orr-Weaver, T. L. & Szostak, J. W. Yeast recombination: the association between double-strand gap repair and crossing-over. *Proc. Natl. Acad. Sci. U.S.A* 80, 4417-4421 (1983).

124. Ma, H., Kunes, S., Schatz, P. J., & Botstein, D. Plasmid construction by homologous recombination in yeast. *Gene* 58, 201-216 (1987).

125. Chao, G. et al. Isolating and engineering human antibodies using yeast surface display. *Nat. Protoc.* 1, 755-768 (2006).

126. Rakestraw, J. A., Aird, D., Aha, P. M., Baynes, B. M., & Lipovsek, D. Secretion-and-capture cell-surface display for selection of target-binding proteins. *Protein Eng Des Sel* 24, 525-530 (2011).

127. Laemmli, U. K. Cleavage of structural proteins during the assembly of the head of bacteriophage T4. *Nature* 227, 680-685 (1970).

128. Meyer, T. S. & Lamberts, B. L. Use of coomassie brilliant blue R250 for the electrophoresis of microgram quantities of parotid saliva proteins on acrylamide-gel strips. *Biochim. Biophys. Acta* 107, 144-145 (1965).

129. Gultekin, H. & Heermann, K. H. The use of polyvinylidenedifluoride membranes as a general blotting matrix. *Anal. Biochem.* 172, 320-329 (1988).

130. Renart, J., Reiser, J., & Stark, G. R. Transfer of proteins from gels to diazobenzyloxymethyl-paper and detection with antisera: a method for studying antibody specificity and antigen structure. *Proc. Natl. Acad. Sci. U.S.A* 76, 3116-3120 (1979).

131. Mullis, K. et al. Specific enzymatic amplification of DNA in vitro: the polymerase chain reaction. *Cold Spring Harb. Symp. Quant. Biol.* 51 Pt 1, 263-273 (1986).

132. Saiki, R. K. et al. Primer-directed enzymatic amplification of DNA with a thermostable DNA polymerase. *Science* 239, 487-491 (1988).

133. Saiki, R. K. et al. Enzymatic amplification of beta-globin genomic sequences and restriction site analysis for diagnosis of sickle cell anemia. *Science* 230, 1350-1354 (1985).

134. Sanger, F., Nicklen, S., & Coulson, A. R. DNA sequencing with chain-terminating inhibitors. *Proc. Natl. Acad. Sci. U.S.A* 74, 5463-5467 (1977).
135. Murray, V. Improved double-stranded DNA sequencing using the linear polymerase chain reaction. *Nucleic Acids Res.* 17, 8889 (1989).
136. McCafferty, J., Griffiths, A. D., Winter, G., & Chiswell, D. J. Phage antibodies: filamentous phage displaying antibody variable domains. *Nature* 348, 552-554 (1990).
137. Wittrup, K. D. Disulfide bond formation and eukaryotic secretory productivity. *Curr. Opin. Biotechnol.* 6, 203-208 (1995).
138. Boeke, J. D., Trueheart, J., Natsoulis, G., & Fink, G. R. 5-Fluoroorotic acid as a selective agent in yeast molecular genetics. *Methods Enzymol.* 154, 164-175 (1987).
139. Veit, B. E. & Fangman, W. L. Copy number and partition of the *Saccharomyces* cerevisiae 2 micron plasmid controlled by transcription regulators. *Mol. Cell Biol.* 8, 4949-4957 (1988).
140. Uma Maheswar Rao, J. L. & Satyanarayana, T. Enhanced secretion and low temperature stabilization of a hyperthermostable and Ca2+-independent+|–amylase of *Geobacillus thermoleovorans* by surfactants. *Letters in Applied Microbiology* 36, 191-196 (2003).
141. Romanos, M. A., Scorer, C. A., & Clare, J. J. Foreign gene expression in yeast: a review. *Yeast* 8, 423-488 (1992).
142. Kuroda, K. et al. Efficient antibody production upon suppression of O mannosylation in the yeast *Ogataea minuta*. *Appl. Environ. Microbiol.* 74, 446-453 (2008).
143. Kronvall, G. & Williams, R. C., Jr. Differences in anti-protein A activity among IgG subgroups. *J. Immunol.* 103, 828-833 (1969).
144. Jendeberg, L. et al. Kinetic analysis of the interaction between protein A domain variants and human Fc using plasmon resonance detection. *J. Mol. Recognit.* 8, 270-278 (1995).
145. Boyle, M. D., Wallner, W. A., von Mering, G. O., Reis, K. J., & Lawman, M. J. Interaction of bacterial Fc receptors with goat immunoglobulins. *Mol. Immunol.* 22, 1115-1121 (1985).
146. Heitzmann, H. & Richards, F. M. Use of the avidin-biotin complex for specific staining of biological membranes in electron microscopy. *Proc. Natl. Acad. Sci. U.S.A* 71, 3537-3541 (1974).
147. Fukuda, N. et al. High-efficiency recovery of target cells using improved yeast display system for detection of protein-protein interactions. *Appl. Microbiol. Biotechnol.* 76, 151-158 (2007).
148. Wang, M., Yang, Z., Rada, C., & Neuberger, M. S. AID upmutants isolated using a high-throughput screen highlight the immunity/cancer balance limiting DNA deaminase activity. *Nat. Struct. Mol. Biol.* 16, 769-776 (2009).
149. Cedergren, L., Andersson, R., Jansson, B., Uhlen, M., & Nilsson, B. Mutational analysis of the interaction between staphylococcal protein A and human IgG1. *Protein Eng* 6, 441-448 (1993).
150. Eliasson, M., Andersson, R., Olsson, A., Wigzell, H., & Uhlen, M. Differential IgG-binding characteristics of staphylococcal protein A, streptococcal protein G, and a chimeric protein AG. *J. Immunol.* 142, 575-581 (1989).
151. Langone, J. J., Boyle, M. D., & Borsos, T. Studies on the interaction between protein A and immunoglobulin G. I. Effect of protein A on the functional activity of IgG. *J. Immunol.* 121, 327-332 (1978).
152. Langone, J. J., Boyle, M. D., & Borsos, T. Studies on the interaction between protein A and immunoglobulin G. II. Composition and activity of complexes formed between protein A and IgG. *J. Immunol.* 121, 333-338 (1978).
153. Sjoquist, J., Meloun, B., & Hjelm, H. Protein A isolated from *Staphylococcus aureus* after digestion with lysostaphin. *Eur. J. Biochem.* 29, 572-578 (1972).
154. Mazor, Y., Van, B. T., Mabry, R., Iverson, B. L., & Georgiou, G. Isolation of engineered, full-length antibodies from libraries expressed in *Escherichia coli*. *Nat. Biotechnol.* 25, 563-565 (2007).
155. Mazor, Y., Van, B. T., Iverson, B. L., & Georgiou, G. E-clonal antibodies: selection of full-length IgG antibodies using bacterial periplasmic display. *Nat. Protoc.* 3, 1766-1777 (2008).
156. Ojala, K. et al. Improved display of synthetic IgG-binding domains on the baculovirus surface. *Technol. Cancer Res. Treat.* 3, 77-84 (2004).
157. Mazor, Y., Van, B. T., Carroll, S., & Georgiou, G. Selection of full-length IgGs by tandem display on filamentous phage particles and *Escherichia coli* fluorescence-activated cell sorting screening. *FEBS J.* 277, 2291-2303 (2010).
158. Nakamura, Y. et al. Development of novel whole-cell immunoadsorbents by yeast surface display of the IgG-binding domain. *Appl. Microbiol. Biotechnol.* 57, 500-505 (2001).
159. Ito, J. et al. Regulation of the display ratio of enzymes on the *Saccharomyces cerevisiae* cell surface by the immunoglobulin G and cellulosomal enzyme binding domains. *Appl. Environ. Microbiol.* 75, 4149-4154 (2009).
160. Samuelsson, E., Moks, T., Nilsson, B., & Uhlen, M. Enhanced in vitro refolding of insulin-like growth factor I using a solubilizing fusion partner. *Biochemistry* 33, 4207-4211 (1994).
161. Samuelsson, E. & Uhlen, M. Chaperone-like effect during in vitro refolding of insulin-like growth factor I using a solubilizing fusion partner. *Ann. N. Y. Acad. Sci.* 782, 486-494 (1996).
162. Robinson, A. S., Hines, V., & Wittrup, K. D. Protein disulfide isomerase overexpression increases secretion of foreign proteins in *Saccharomyces cerevisiae*. *Biotechnology (N. Y.)* 12, 381-384 (1994).
163. Hiniker, A. & Bardwell, J. C. Disulfide relays between and within proteins: the Ero1p structure. *Trends Biochem. Sci.* 29, 516-519 (2004).
164. Gühlich, S., Uhlén, M., & Hober, S. Protein engineering of an IgG-binding domain allows milder elution conditions during affinity chromatography. *Journal of Biotechnology* 76, 233-243 (2000).
165. Schekman, R. The secretory pathway in yeast. *Trends in Biochemical Sciences* 7, 243-246 (1982).
166. Arnold, K., Herrmann, A., Pratsch, L., & Gawrisch, K. The dielectric properties of aqueous solutions of poly(ethylene glycol) and their influence on membrane structure. *Biochimica et Biophysica Acta (BBA)—Biomembranes* 815, 515-518 (1985).
167. Kuhl, T. et al. Direct Measurement of Polyethylene Glycol Induced Depletion Attraction between Lipid Bilayers. *Langmuir* 12, 3003-3014 (1996).
168. Boni, L. T., Stewart, T. P., Alderfer, J. L., & Hui, S. W. Lipid-polyethylene glycol interactions: I. Induction of fusion between liposomes. *J. Membr. Biol.* 62, 65-70 (1981).

169. KRAMER, W., ELMECKER, G., WEIK, R., Mattanovich, D., & BAYER, K. Kinetic Studies for the Optimization of Recombinant Protein Formation. *Annals of the New York Academy of Sciences* 782, 323-333 (1996).
170. Sanden, A. M. et al. Limiting factors in *Escherichia coli* fed-batch production of recombinant proteins. *Biotechnol. Bioeng.* 81, 158-166 (2003).
171. Barthelemy, P. A. et al. Comprehensive analysis of the factors contributing to the stability and solubility of autonomous human VH domains. *J. Biol. Chem.* 283, 3639-3654 (2008).
172. Ueda, M. & Tanaka, A. Genetic immobilization of proteins on the yeast cell surface. *Biotechnol. Adv.* 18, 121-140 (2000).
173. Schmiedl, A. D. S. Rekombinante Antikörper and Phagen Display. Wiley-VCH from "Molekulare Biotechnologie". 2004. M. Wink, Wiley-VCH. Reference type: Magazine article
174. Saerens, D., Ghassabeh, G. H., & Muyldermans, S. Single-domain antibodies as building blocks for novel therapeutics. *Curr. Opin. Pharmacol.* 8, 600-608 (2008).
175. Yamane-Ohnuki, N. & Satoh, M. Production of therapeutic antibodies with controlled fucosylation. *MAbs.* 1, 230-236 (2009).
176. Deisenhofer, J. Crystallographic refinement and atomic models of a human Fc fragment and its complex with fragment B of protein A from *Staphylococcus aureus* at 2.9- and 2.8-A resolution. *Biochemistry* 20, 2361-2370 (1981).
177. Vajdos, F. F. et al. Comprehensive functional maps of the antigen-binding site of an anti-ErbB2 antibody obtained with shotgun scanning mutagenesis. *J. Mol. Biol.* 320, 415-428 (2002).
178. Hashimoto, Y., Koyabu, N., & Imoto, T. Effects of signal sequences on the secretion of hen lysozyme by yeast: construction of four secretion cassette vectors. *Protein Eng* 11, 75-77 (1998).
179. Sazinsky, S. L. et al. Aglycosylated immunoglobulin G1 variants productively engage activating Fc receptors. *Proc. Natl. Acad. Sci. U.S.A* 105, 20167-20172 (2008).
180. Ewert, S., Cambillau, C., Conrath, K., & Pluckthun, A. Biophysical properties of camelid V(HH) domains compared to those of human V(H)3 domains. *Biochemistry* 41, 3628-3636 (2002).
181. Ewert, S., Huber, T., Honegger, A., & Pluckthun, A. Biophysical properties of human antibody variable domains. *J. Mol. Biol.* 325, 531-553 (2003).
182. De, G. E. et al. Molecular basis for the preferential cleft recognition by dromedary heavy-chain antibodies. *Proc. Natl. Acad. Sci. U.S.A* 103, 4586-4591 (2006).
183. Wang, M., Yang, Z., Rada, C., & Neuberger, M. S. AID upmutants isolated using a high-throughput screen highlight the immunity/cancer balance limiting DNA deaminase activity. *Nat. Struct. Mol. Biol.* 16, 769-776 (2009).
184. Neuberger, M. S. et al. Somatic hypermutation at A.T pairs: polymerase error versus dUTP incorporation. *Nat. Rev. Immunol.* 5, 171-178 (2005).
185. Ablynx N. V. Nanobodies and Polypetides against EGFR and IGF-IF. WO 2007/042289 A2. 2007.
186. Bostrom, J. et al. Variants of the antibody herceptin that interact with HER2 and VEGF at the antigen binding site. *Science* 323, 1610-1614 (2009).
187. Baeuerle, P. A. & Reinhardt, C. Bispecific T-cell engaging antibodies for cancer therapy. *Cancer Res.* 69, 4941-4944 (2009).
188. Mack, M., Riethmuller, G., & Kufer, P. A small bispecific antibody construct expressed as a functional single-chain molecule with high tumor cell cytotoxicity. *Proc. Natl. Acad. Sci. U.S.A* 92, 7021-7025 (1995).
189. Brennan, F. R. et al. Safety and immunotoxicity assessment of immunomodulatory monoclonal antibodies. *MAbs.* 2, 233-255 (2010).
190. DeLano, W. L., Ultsch, M. H., de Vos, A. M., & Wells, J. A. Convergent solutions to binding at a protein-protein interface. *Science* 287, 1279-1283 (2000).
191. Li, S. et al. Structural basis for inhibition of the epidermal growth factor receptor by cetuximab. *Cancer Cell* 7, 301-311 (2005).
192. Loisel, S. et al. Relevance, advantages and limitations of animal models used in the development of monoclonal antibodies for cancer treatment. *Crit Rev. Oncol. Hematol.* 62, 34-42 (2007).
193. Muyldermans, S., Cambillau, C., & Wyns, L. Recognition of antigens by single-domain antibody fragments: the superfluous luxury of paired domains. *Trends Biochem. Sci.* 26, 230-235 (2001).
194. Shusta, E. V., Kieke, M. C., Parke, E., Kranz, D. M., & Wittrup, K. D. Yeast polypeptide fusion surface display levels predict thermal stability and soluble secretion efficiency. *J. Mol. Biol.* 292, 949-956 (1999).
195. Kieke, M. C. et al. Selection of functional T cell receptor mutants from a yeast surface-display library. *Proc. Natl. Acad. Sci. U.S.A* 96, 5651-5656 (1999).

The invention claimed is:
1. A method for producing a selected population of antibodies, by expression, secretion, and presentation of a mixed population of antibodies on the surface of yeast cells, the method comprising the following steps:
(a) providing host cells of the yeast species *Saccharomyces cerevisiae* that have been transfected with a first and a second nucleic acid molecule on expression plasmids, wherein the first nucleic acid molecule comprises a yeast GAL1 promoter and encodes a fusion protein, wherein the GAL1 promoter is capable of controlling the expression of said fusion protein as a function of cultivation conditions, and wherein said fusion protein comprises an alpha-agglutinin cell surface anchor protein and an Fc binding domain, and wherein the second nucleic acid molecule encodes an antibody of said mixed population of antibodies and is under the control of a permanently active promoter;
(b) cultivating said host cells of (a) in the presence of >10% w/v polyethylene glycol (PEG) having a molecular weight of >5,000 in the cultivation medium, under conditions whereby said mixed population of antibodies is simultaneously co-expressed in soluble form with said fusion protein, whereby said fusion protein is anchored to the surface of the host cell upon secretion, and whereby each host cell expresses an individual antibody of said mixed population of antibodies, and whereby said antibodies of said mixed population of antibodies are secreted from the host cells and bound in non-covalent form to said Fc binding domain of said fusion protein on the surface of each host cell,
(c) selecting and isolating a population of said host cells of (b) according to the affinity of individual antibodies in said mixed population of antibodies by binding a detection marker to said individual antibodies, wherein the detection marker is selective for said individual antibodies, and isolating the yeast cells which are bound to the detection marker,

(d) culturing said isolated host cells of (c) and expressing said individual antibodies selected in (c) under cultivation conditions wherein little or no expression of said fusion protein occurs and wherein the expressed antibodies from said second expression step are secreted from the yeast cell without binding to the surface of said isolated host cells of (c), and (e) isolating the secreted antibodies expressed in (d) selected binding affinity.

2. The method according to claim 1, wherein said fusion protein encoded by said first nucleic acid molecule comprises aga2p.

3. The method according to claim 2, wherein said Fc binding domain is the protein A ZZ domain.

4. The method according to claim 3, wherein said cell surface-anchored fusion protein is bound to a cell surface-displayed aga1p subunit.

5. The method according to claim 4, wherein said permanently active promoter is the GAPDH promoter.

6. The method according to claim 1, wherein said PEG comprises PEG8000 or a PEG with a molecular weight higher than 8000.

7. The method according to claim 1, wherein said *Saccharomyces cerevisiae* is *Saccharomyces cerevisiae* strain EBY100.

8. The method according to claim 1, wherein said first nucleic acid molecule and said second nucleic acid molecule are located on separate plasmids.

9. The method according to claim 8, wherein at least one of said separate plasmids use pYDI as the starting plasmid.

* * * * *

UNITED STATES PATENT AND TRADEMARK OFFICE
CERTIFICATE OF CORRECTION

| | |
|---|---|
| PATENT NO. | : 10,138,477 B2 |
| APPLICATION NO. | : 14/758856 |
| DATED | : November 27, 2018 |
| INVENTOR(S) | : Ralph Guenther et al. |

It is certified that error appears in the above-identified patent and that said Letters Patent is hereby corrected as shown below:

In the Claims

At Column 61, Claim 1, Line 9, the text "selected binding affinity." should be changed to -- having the selected binding affinity. --

Signed and Sealed this
Twenty-first Day of June, 2022

Katherine Kelly Vidal
*Director of the United States Patent and Trademark Office*